US011324708B1

(12) United States Patent
Sommer et al.

(10) Patent No.: US 11,324,708 B1
(45) Date of Patent: *May 10, 2022

(54) NICLOSAMIDE FORMULATIONS FOR TREATING DISEASE

(71) Applicant: UNION therapeutics A/S, Hellerup (DK)

(72) Inventors: Morten Otto Alexander Sommer, Hellerup (DK); Rasmus Toft-Kehler, Hellerup (DK); Anne Katrine Toft-Kehler, Hellerup (DK); Günter Ditzinger, Hellerup (DK); Mads Jellingsoe, Hellerup (DK); Philippe Andres, Hellerup (DK); Matthias Manne Knopp, Hellerup (DK)

(73) Assignee: UNION therapeutics A/S, Hellerup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/330,067

(22) Filed: May 25, 2021

Related U.S. Application Data

(63) Continuation of application No. 17/097,898, filed on Nov. 13, 2020, now Pat. No. 11,045,434.

(30) Foreign Application Priority Data

| Apr. 1, 2020 | (GB) | 2004844 |
| Apr. 9, 2020 | (GB) | 2005340 |
| Jul. 9, 2020 | (GB) | 2010573 |
| Oct. 14, 2020 | (GB) | 2016274 |

(51) Int. Cl.
| *A61K 31/167* | (2006.01) |
| *A61K 9/08* | (2006.01) |
| *A61K 9/10* | (2006.01) |
| *A61K 47/32* | (2006.01) |
| *A61K 47/40* | (2006.01) |
| *A61K 9/00* | (2006.01) |
| *A61K 9/12* | (2006.01) |

(52) U.S. Cl.
CPC .......... *A61K 31/167* (2013.01); *A61K 9/0043* (2013.01); *A61K 9/0073* (2013.01); *A61K 9/08* (2013.01); *A61K 9/12* (2013.01); *A61K 47/32* (2013.01); *A61K 47/40* (2013.01)

(58) Field of Classification Search
None
See application file for complete search history.

(56) References Cited

U.S. PATENT DOCUMENTS

| 4,742,083 | A | 5/1988 | Ritchey |
| 6,207,179 | B1 * | 3/2001 | Mihalik .............. A61K 9/0056 424/405 |
| 8,148,328 | B2 | 4/2012 | Fogelman et al. |
| 9,023,368 | B2 | 5/2015 | Basit et al. |
| 9,308,213 | B2 | 4/2016 | Bannister |
| 9,669,036 | B2 | 6/2017 | Roizman et al. |
| 9,949,988 | B2 | 4/2018 | Delavenne et al. |
| 10,189,797 | B2 | 1/2019 | Chen et al. |
| 10,463,680 | B2 | 11/2019 | Sommer et al. |
| 10,562,864 | B2 | 2/2020 | Chen et al. |
| 10,744,103 | B2 | 8/2020 | Glick et al. |
| 10,758,553 | B2 | 9/2020 | Delavenne et al. |
| 10,772,854 | B2 | 9/2020 | Glick et al. |
| 10,857,164 | B2 | 12/2020 | Sommer et al. |
| 10,980,756 | B1 | 4/2021 | Glick |
| 11,045,434 | B1 | 6/2021 | Sommer et al. |
| 11,147,779 | B2 | 10/2021 | Deshpande et al. |
| 2004/0071757 | A1 | 4/2004 | Rolf |
| 2009/0149545 | A1 | 6/2009 | Hsu et al. |
| 2009/0163408 | A1 | 6/2009 | Fogelman et al. |
| 2017/0056347 | A1 * | 3/2017 | Glick .................. A61K 31/167 |
| 2018/0015153 | A1 | 1/2018 | Tang et al. |
| 2019/0151231 | A1 | 5/2019 | Sommer et al. |
| 2019/0160028 | A1 | 5/2019 | Li et al. |
| 2019/0201422 | A1 | 7/2019 | Sommer et al. |
| 2019/0269826 | A1 | 9/2019 | Peyman |
| 2019/0298670 | A1 | 10/2019 | Glick et al. |
| 2020/0022931 | A1 | 1/2020 | Deshpande et al. |
| 2020/0046659 | A1 | 2/2020 | Melnyk |
| 2020/0147012 | A1 | 5/2020 | Glick et al. |
| 2020/0147013 | A1 | 5/2020 | Glick et al. |
| 2020/0197339 | A1 | 6/2020 | Glick et al. |

(Continued)

FOREIGN PATENT DOCUMENTS

| CN | 1232248 C | 12/2005 |
| CN | 1232253 C | 12/2005 |

(Continued)

OTHER PUBLICATIONS

Ashland, PVP K-30 polymer, Oct. 5, 2016, printed from https://www.brenntag.com/media/documents/bsi/product-data-sheets/material-science/ashland-polymers/pvp_k-30_polymer_pds.pdf, 5 pages.*

Gatica et al., Cyclodextrine-nanoencapsulation of niclosamide: Water solubility and meaningful enhancement of visible-light—Mediated sensitized photodegradation of the drug, Journal of Photochemistry and Photobiology A: Chemistry, vol. 348, 2017, 295-304.*

Alonso et al., Journal of Medical Virology, Aug. 21, 2020, 93(2):655-656, Recurrence of SARS-CoV-2 infection with a more severe case after mild COVID-19, reversion of RT-qPCR for positive and late antibody response: Case report.

Pindiprolu et al., Medical Hypotheses, Jul. 2020, 140. Plausible mechanisms of Niclosamide as an antiviral agent against COVID-19.

(Continued)

*Primary Examiner* — Gigi G Huang
(74) *Attorney, Agent, or Firm* — Mintz Levin Cohn Ferris Glovsky and Popeo, P.C.

(57) ABSTRACT

The invention relates to a method of treating a viral infection caused by or associated with SARS-CoV-2 in a subject, the method comprising administering to the subject by inhalation intraorally and/or intranasally a therapeutically effective amount of a formulation comprising niclosamide, or a pharmaceutically acceptable salt thereof, and a cyclodextrin.

6 Claims, 3 Drawing Sheets

(56) References Cited

U.S. PATENT DOCUMENTS

Figure 1A:
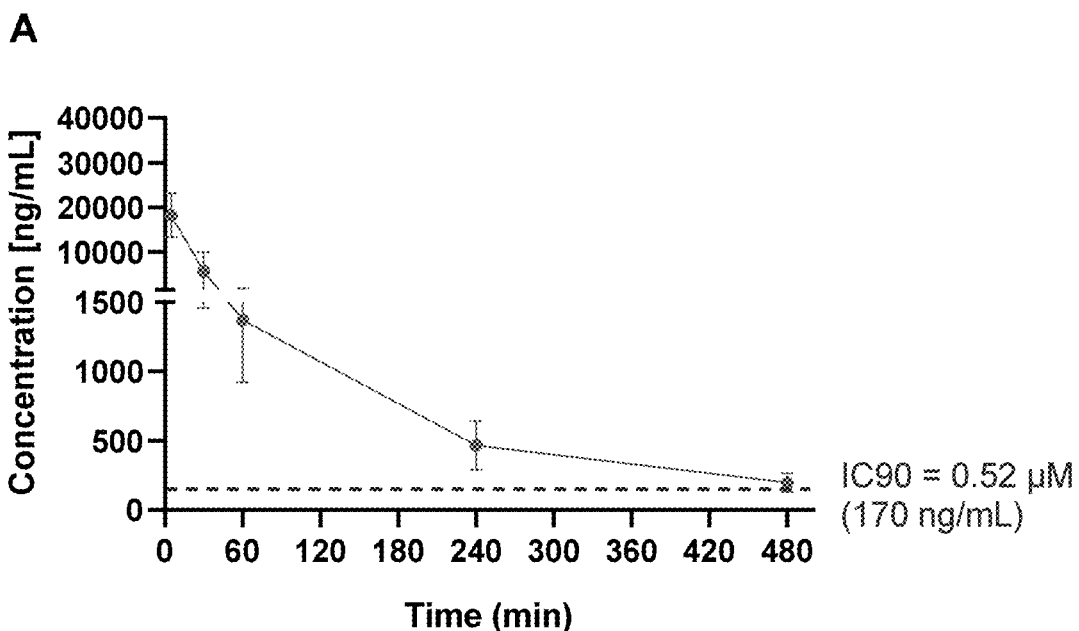

| | | |
|---|---|---|
| 2020/0197340 A1 | 6/2020 | Glick et al. |
| 2020/0268693 A1 | 8/2020 | Mylonakis et al. |
| 2020/0268694 A1 | 8/2020 | Glick et al. |
| 2020/0276140 A1 | 9/2020 | Glick et al. |
| 2020/0306269 A1 | 10/2020 | Delavenne et al. |
| 2020/0306270 A1 | 10/2020 | Delavenne et al. |
| 2020/0306271 A1 | 10/2020 | Delavenne et al. |
| 2021/0137948 A1 | 5/2021 | Sommer |
| 2021/0308079 A1 | 10/2021 | Holmes et al. |
| 2021/0308153 A1 | 10/2021 | Sommer et al. |
| 2021/0369650 A1 | 12/2021 | Guttman-Yassky et al. |

FOREIGN PATENT DOCUMENTS

| | | |
|---|---|---|
| CN | 106360011 A | 1/2017 |
| CN | 109380226 A * | 2/2019 |
| CN | 110279657 A | 9/2019 |
| CN | 110833623 A * | 2/2020 |
| EP | 1655034 | 5/2006 |
| EP | 3168211 A1 | 5/2017 |
| IL | 248106 A | 6/2020 |
| UY | 36062 | 10/2015 |
| WO | WO-01/34232 | 5/2001 |
| WO | WO-2001032246 | 5/2001 |
| WO | WO-2001056639 | 8/2001 |
| WO | WO-2001085241 | 11/2001 |
| WO | WO-2002013896 | 2/2002 |
| WO | WO-2002064265 | 8/2002 |
| WO | WO-2003035152 | 5/2003 |
| WO | WO-2003035153 | 5/2003 |
| WO | WO-2004004813 | 1/2004 |
| WO | WO-2004014569 | 2/2004 |
| WO | WO-2004020029 | 3/2004 |
| WO | WO-2004028606 | 4/2004 |
| WO | WO-2004039442 | 5/2004 |
| WO | WO-2004041335 | 5/2004 |
| WO | WO-2004041336 | 5/2004 |
| WO | WO-2004052436 | 6/2004 |
| WO | WO-2004098689 | 11/2004 |
| WO | WO-2005032630 | 4/2005 |
| WO | WO-2005037246 | 4/2005 |
| WO | WO-2005042075 | 5/2005 |
| WO | WO-2006084543 | 8/2006 |
| WO | WO-2006084546 | 8/2006 |
| WO | WO-2006108556 | 10/2006 |
| WO | WO-2006128567 | 12/2006 |
| WO | WO-2007020073 | 2/2007 |
| WO | WO-2007118557 | 10/2007 |
| WO | WO-2008021088 | 2/2008 |
| WO | WO-2008113651 | 9/2008 |
| WO | WO-2009135871 | 11/2009 |
| WO | WO-2010066714 | 6/2010 |
| WO | WO-2010094767 | 8/2010 |
| WO | WO-2010097119 | 9/2010 |
| WO | WO-2010139730 | 12/2010 |
| WO | 2011035321 A1 | 3/2011 |
| WO | WO-2011134940 | 11/2011 |
| WO | WO-2012069531 | 5/2012 |
| WO | WO-2012168181 | 12/2012 |
| WO | WO-2013013852 | 1/2013 |
| WO | WO-2014040947 | 3/2014 |
| WO | WO-2014082818 | 6/2014 |
| WO | 2014185973 A2 | 11/2014 |
| WO | WO-2015091356 | 6/2015 |
| WO | WO-2015128375 | 9/2015 |
| WO | WO-2015193432 | 12/2015 |
| WO | WO-2016015889 | 2/2016 |
| WO | WO-2016026802 | 2/2016 |
| WO | 2016038035 A1 | 3/2016 |
| WO | WO-2016102308 | 6/2016 |
| WO | WO-2016193136 | 12/2016 |
| WO | WO-2017021441 | 2/2017 |
| WO | 2017040864 A1 | 3/2017 |
| WO | WO-2017/157997 | 9/2017 |
| WO | WO-2017223491 | 12/2017 |
| WO | 2018017426 A1 | 1/2018 |
| WO | WO-2018051102 | 3/2018 |
| WO | 2018136559 A1 | 7/2018 |
| WO | WO-2018167278 | 9/2018 |
| WO | 2018205016 A1 | 11/2018 |
| WO | 2019038443 A1 | 2/2019 |
| WO | WO-2019115771 | 6/2019 |
| WO | 2019147626 A1 | 8/2019 |
| WO | WO-2019192968 | 10/2019 |
| WO | WO-2019202085 | 10/2019 |
| WO | WO-2020/039073 | 2/2020 |
| WO | 2020091804 A1 | 5/2020 |
| WO | WO-2020176067 | 9/2020 |
| WO | 2021040337 A1 | 3/2021 |
| WO | WO-2021/076922 | 4/2021 |
| WO | 2021142240 A1 | 7/2021 |
| WO | 2021155443 A1 | 8/2021 |
| WO | 2021168295 A1 | 8/2021 |
| WO | 2021168328 A1 | 8/2021 |
| WO | 2021187842 A1 | 9/2021 |
| WO | 2021188564 A1 | 9/2021 |
| WO | 2021198116 A1 | 10/2021 |
| WO | 2021198415 A1 | 10/2021 |
| WO | 2021201796 A1 | 10/2021 |
| WO | 2021201805 A1 | 10/2021 |
| WO | 2021202928 A1 | 10/2021 |

OTHER PUBLICATIONS

Backer et al., "A randomized, double-blind, placebo-controlled phase 1 trial of inhaled and intranasal niclosamide: A broad spectrum antiviral candidate for treatment of COVID-19," The Lancet Regional Health—Europe, 13 pages (Available Apr. 6, 2021).

Barr et al., "American Translation, Modification, and Validation of the St. George's Respiratory Questionnaire," Clin. Ther., 22(9), pp. 1121-1145 (2000).

Cabrita et al., "Niclosamide repurposed for the treatment of inflammatory airway disease," JCI Insight., 4(15):e128414, 15 pages (2019).

Chen et al., "Clinical progression of patients with COVID-19 in Shanghai, China," J. Infect., 80(5), pp. e1-e6 (2020).

Corman et al., "Hosts and Sources of Endemic Human Coronaviruses," Adv. Virus Res., 100, pp. 163-188 (2018).

Costabile et al., "Toward Repositioning Niclosamide for Antivirulence Therapy of *Pseudomonas aeruginosa* Lung Infections: Development of Inhalable Formulations through Nanosuspension Technology," Mol. Pharm., 12(8), pp. 2604-2617 (2015).

Devarakonda et al., "Comparison of the aqueous solubilization of practically insoluble niclosamide by polyamidoamine (PAMAM) dendrimers and cyclodextrins," International Journal of Pharmaceutics, 304(1-2), pp. 193-209 (2005).

Fehr and Perlman, "Coronaviruses: An Overview of Their Replication and Pathogenesis," *Coronaviruses: Methods and Protocols*, Maier et al. eds., Springer New York, NY, Methods in Molecular Biology, vol. 1282, pp. 1-23 (2015).

Garcia et al., "A phenotypic small-molecule screen identifies halogenated salicylanilides as inhibitors of fungal morphogenesis, biofilm formation and host cell invasion," Sci. Rep., 8:11559, 15 pages (2018).

Genbank accession No. MN908947.3, "Severe acute respiratory syndrome coronavirus 2 isolate Wuhan-Hu-1, complete genome," 11 pages (Mar. 18, 2020).

Hemida and Abduallah, "The SARS-CoV-2 outbreak from a one health perspective," One Health (Journal pre-proof) 24 pages (2019).

Hessen et al., "Dry Eye: an Inflammatory Ocular Disease," J. Ophthalmic Vis. Res., 9(2), pp. 240-250 (2014).

Hou et al., "SARS-CoV-2 Reverse Genetics Reveals a Variable Infection Gradient in the Respiratory Tract," Cell, 182, pp. 429-446 (2020).

Huang et al., "Clinical features of patients infected with 2019 novel coronavirus in Wuhan, China", The Lancet, 395(102223), pp. 497-506 (Jan. 24, 2020).

(56) References Cited

OTHER PUBLICATIONS

Jabs et al., "Guidelines for the Use of Immunosuppressive Drugs in Patients with Ocular Inflammatory Disorders: Recommendations of an Expert Panel," Am. J. Ophthalmol., 130(4), pp. 492-513 (2000).

Jeon et al., "Identification of antiviral drug candidates against SARS-CoV-2 from FDA-approved drugs," Antimicrobial Agents and Chemotherapy, 64(7), 21 pages (2020).

Jones et al., "A Self-complete Measure of Health Status for Chronic Airflow Limitation: The St. George's Respiratory Questionnaire," Am. Rev. Respir. Dis., 145, pp. 1321-1327 (1992).

Jurgeit et al., "Niclosamide Is a Proton Carrier and Targets Acidic Endosomes with Broad Antiviral Effects," PLoS Pathog., 8(10), e1002976, 14 pages (2012).

Lodagekar et al., "Formulation and evaluation of cyclodextrin complexes for improved anticancer activity of repurposed drug: Niclosamide," Carbohydrate Polymers, 212, pp. 252-259 (2019).

Marrugal-Lorenzo et al., "Repositioning salicylanilide anthelmintic drugs to treat adenovirus infections," Sci. Rep., 9(17), 10 pages (2019).

Rajamuthiah et al., "Repurposing Salicylanilide Anthelmintic Drugs to Combat Drug Resistant *Staphylococcus aureus*," PLOS One, 10(4), 19 pages (2015).

Wang et al., "Remdesivir and chloroquine effectively inhibit the recently emerged novel coronavirus (2019-nCoV) in vitro," Cell Res., 30, pp. 269-271 (2020).

Wen et al., "Specific Plant Terpenoids and Lignoids Possess Potent Antiviral Activities against Severe Acute Respiratory Syndrome Coronavirus," J. Med. Chem., 50, pp. 4087-4095 (2007).

Wu et al., "A new coronavirus associated with human respiratory disease in China," Nature, 579, pp. 265-269 (2020).

Wu et al., "Characteristics of Ocular Findings of Patients With Coronavirus Disease 2019 (COVID-19) in Hubei Province, China," JAMA Ophthalmol., pp. E1-E4 (2020).

Wu et al., "Inhibition of Severe Acute Respiratory Syndrome Coronavirus Replication by Niclosamide," Antimicrob. Agents Chemother., 48, pp. 2693-2696 (2004).

Xu et al., "Broad Spectrum Antiviral Agent Niclosamide and Its Therapeutic Potential," ACS Infect. Dis., pp. 909-915 (2020).

Yang and de Villiers, "Effect of 4-Sulphonato-Calix[n]Arenes and Cyclodextrins on the Solubilization of Niclosamide, a Poorly Water Soluble Anthelmintic," The AAPS Journal, 7(1), Article 23, pp. E241-E248 (2005).

Zhang et al., "Cytokine release syndrome in severe COVID-19: interleukin-6 receptor antagonist tocilizumab may be the key to reduce mortality," International Journal of Antimicrobial Agents, 55, 6 pages (2020).

Fang et al. (Nov. 2013) "Identification of Three Antiviral Inhibitors Against Japanese Encephalitis Virus from Library of Pharmacologically Active Compounds 1280", PLoS One, Article No. e78425, 8(11):8 pages.

Gassen et al. (2019) "SKP2 Attenuates Autophagy Through Beclin1-ubiquitination and its Inhibition Reduces MERS-Coronavirus Infection", Nature Communications, Article No. 5770, 10(1):16 pages.

Huang et al. (2017) "Niclosamide Inhibits Lytic Replication of Epstein-Barr Virus by Disrupting mTOR Activation", Antiviral Research, 138:68-78.

Jung et al. (2019) "Neutralization of Acidic Intracellular Vesicles by Niclosamide Inhibits Multiple Steps of the Dengue Virus Life Cycle In Vitro", Scientific Reports, Article No. 8682, 9:12 pages.

Madrid et al. (2015) "Evaluation of Ebola Virus Inhibitors for Drug Repurposing", ACS Infectious Diseases, 1(7):317-326.

Mazzon et al. (2019) "Identification of Broad-Spectrum Antiviral Compounds by Targeting Viral Entry", Viruses, 11 (2):176(26 pages).

Stachulski et al. (2011) "Thiazolides as Novel Antiviral Agents. 2. Inhibition of Hepatitis C Virus Replication", Journal of Medicinal Chemistry, 54(24):8670-8680.

Wang et al. (2016) "Antiviral Activities of Niclosamide and Nitazoxanide Against Chikungunya Virus Entry and Transmission", Antiviral Research, 135:81-90.

Xu et al. (Oct. 2016) "Identification of Small-molecule Inhibitors of Zika Virus Infection and Induced Neural Cell Death Via a Drug Repurposing Screen", Nature Medicine, 22(10):110-1107.

Niclosamide In Moderate COVID-19 (Clinicaltials.gov Identifier NCT04436458), First Wave Bio, Inc. (First Posted Jun. 18, 2020); Retrieved from https://clinicaltrials.gov/ct2/show/NCT04436458=term=niclosamide&cond=Covid19&draw=2&rank=2., 5 pages.

Niclosamide In Moderate COVID-19 (Clinicaltials.gov Identifier NCT04542434), First Wave Bio, Inc. (First Posted Sep. 9, 2020); retrieved from https://clinicaltrials.gov/ct2/show/NCT04542434=term=niclosamide&cond=Covid19&draw=2&rank=2., 6 pages.

South Korea's Daewoong Pharmaceutical says anti-parasitic drug effective against coronavirus in animal tests, (Jun. 9, 2020) Healthcare & Pharma, 2 pages.

TFF Pharmaceuticals' Inventor Dr. Robert O. Williams III Presents Session on Repurposing Niclosamide for COVID-19 Treatment at AAPS Meeting, (Apr. 30.2020) Ir.tffpharma.com i [online]; [retrieved on May 19, 2020], retrieved from URL<https:/ir.tffpharma.com/news-releases/news-release-detalls/tff-pharmaceuticals-inventor-dr-robert-o-williams-iii-presents>, 2 pages.

UNION therapeutics launches COVID-19 program in collaboration with Institut Pasteur Korea, (Apr. 2, 2020) Uniontherapeutics.com [online]; [retrieved on May 19, 2020], retrieved from: URL<https://www.uniontherapeutics.com/news-events/news/union-therapeutics-launches-covid-19-program-in-collaboration-with-institut-pasteur-korea>, 3 pages.

Anonymous, "New Delivery Method Could Make Niclosamide an Effective Antiviral to Treat COVID-19", UTexas PressRelease, Apr. 6, 2020, [retrieved on May 19, 2020], retrieved from URL<https://news.utexas.edu/2020/04/06/new-delivery-method-could-make-niclasamide-an-effective-antiviral-to-treat-covid-19/>, 1 pages.

Chang et al. (2006), "Pharmacokinetics of Anti-SARS-CoV Agent Niclosamide and Its Analogs in Rats", Journal of Food and Drug Analysis, 14(4)329-333.

Dubald et al. (Jan. 13, 2018), "Ophthalmic Drug Delivery Systems for Antibiotherapy—A Review", Pharmaceutics, 10(1):10 (31 pages).

Gassen et al. (Apr. 15, 2020), "Analysis of SARS-CoV-2-controlled autophagy reveals spermidine, MK-2206, and niclosamide as 1 putative antiviral therapeutics", bioRxiv, 13 pages.

Jeong Sae-Im (Apr. 24, 2020), "Parasiticide showed antiviral effect as potential COVID-19 drug", Koreabiomed.com [online]; [retrieved on May 19, 2020], retrieved from; URL<http://www.koreabiomed.com/news/articleView.html?idxno=8078>, 5 pages.

Kratky et al. (2011), "Antiviral Activity of Substituted Salicylanilides—A Review", Mini-Review in Medicinal Chemistry, 11:956-967.

Mook et al. (Sep. 1, 2015), "Structure-activity studies of Wnt/β-catenin inhibition in the Niclosamide chemotype: Identification of derivatives with improved drug exposure", Bioorg Med Chem, 23, (17):5829-5838.

Shim Hyun-Tai (Apr. 14, 2020), "Pasteur, Daewoong to co-develop COVID-19 drug from parasiticide". Koreabiomed.com [online]; [retrieved on May 19, 2020], retrieved from: URL<http://www.koreabiomed.com/news/articleView.htm/?idxnos8003>, 2 pages.

* cited by examiner

NICLOSAMIDE FORMULATIONS FOR TREATING DISEASE

CROSS-REFERENCES TO RELATED APPLICATIONS

This application is a continuation of U.S. patent application Ser. No. 17/097,898, filed on Nov. 13, 2020, which claims the benefit of priority to British Patent Application No. 2016274.9, filed on Oct. 14, 2020, British Patent Application No. 2010573.0, filed on Jul. 9, 2020, British Patent Application No. 2005340.1, filed on Apr. 9, 2020, and British Patent Application No. 2004844.3, filed on Apr. 1, 2020, the entire contents of which are herein incorporated by reference.

FORMULATION

This invention relates to pharmaceutical formulations comprising a halogenated salicylanilide, or a pharmaceutically acceptable salt thereof, and a cyclodextrin, and their use in the treatment of diseases including inflammatory disease, infectious disease and ocular disease.

BACKGROUND

Coronaviruses are a group of enveloped and non-segmented positive-sense RNA viruses with very large genome size ranging from approximately 27 to 34 kb. Infections with human strains HCoV-229E, HCoV-0C43, HCoV-NL63 and HCoV-HKU1 usually cause mild, self-limiting respiratory infections, such as the common cold (Fehr et al. Coronaviruses: Methods and Protocols, Maier, H. J.; Bickerton, E.; Britton, P., Eds. Springer New York: New York, N.Y., 2015; pp 1-23 2015 and Corman et al., Adv. Virus Res., J., Eds. Academic Press: 2018; Vol. 100, pp 163-188 2018). However certain highly pathogenic coronaviruses have emerged. SARS-CoV, MERS-CoV and SARS-CoV-2, have caused severe human disease pandemics associated with high morbidity and mortality.

The lack of effective treatment for coronavirus infections poses a great challenge to clinical management and highlights the urgent need to fine new treatments for viral infections such as coronavirus infections.

Wang et al. (Remdesivir and chloroquine effectively inhibit the recently emerged novel coronavirus (2019-nCoV) in vitro. Cell Res. 2020, https://doi.org/10.1038/s41422-020-0282-0) screened antiviral drugs and identified that nitazoxanide, remdesivir and chloroquine, inhibit the SARS-CoV-2 at low-micromolar concentrations in Vero E6 cells with EC50 values of 2.12 µm, 0.77 µm and 1.13 µm, respectively.

Wu et al. (Inhibition of severe acute respiratory syndrome coronavirus replication by niclosamide, Antimicrob. Agents Chemother. 2004, 48, 2693-2696) found that niclosamide inhibits SARS-CoV replication and totally abolished viral antigen synthesis at a concentration of 1.56 µm. Niclosamide suppressed cytopathic effect (CPE) of SARS-CoV at concentration as low as 1 µm and inhibited SARS-CoV replication with an EC50 value of less than 0.1 µm in Vero E6 cells (Wen et al., J. Med. Chem. 2007, 50, 4087-4095.). Niclosamide was later found be a very potent inhibitor of SARS-CoV2 with an IC50 of 280 nM (Joun et al. Clinical features of patients infected with 2019 novel coronavirus in Wuhan, China, The Lancet, https://www.thelancet.com/journals/lancet/article/PIIS0140-6736(20)30183-5/fulltext).

Xu et al. (ACS Infect. Dis. 2020, published on line 3 Mar. 2020 https://doi.org/10.1021/acsinfecdis.0c00052) discloses that niclosamide is effective against certain viral infections. However, this publication concludes that the, low aqueous solubility, poor absorption and low oral bioavailability would limit its clinical development as an antiviral agent.

Cabitra et al., JCI Insight. 2019; 4(15):e128414 discloses the treatment of mice using niclosamide dissolved in corn oil and administered by I.P. injection showed that niclosamide reduced mucus production and secretion, as well as bronchoconstriction, and showed additional anti-inflammatory effects in asthmatic mice.

Niclosamide (tradenames are for instance Yomesan®, Tredemine®) is currently approved and marketed for the oral treatment of tapeworm infections with administration of a single 2 g regimen or 2 g daily for 7 days in adults and children (>2 years of age). The PK analysis revealed that after oral administration, between 2-25% of the administered dose was detected in the urine, which can be considered as the minimum level of absorption. When treating human volunteers each with a single oral dose of 2,000 mg niclosamide, maximal serum concentration of niclosamide was equivalent to 0.25-6.0 µg/mL (0.76-18.3 µM). The wide concentration range was caused by the intraindividual absorption differences. Niclosamide is only partially absorbed from intestinal tract, and the absorbed part is rapidly eliminated by the kidneys. Niclosamide has several other weaknesses such as low absorption and oral bioavailability (F=10%) which may hamper its extensive clinical development as a systemic agent.

WO 2017/157997 discloses certain compositions comprising niclosamide for the topical treatment of conditions such as atopic dermatitis. WO 2020/039073 discloses data showing that niclosamide has anti-inflammatory effects when applied topically to the skin of patients with atopic dermatitis. Topical application of niclosamide modulated numerous inflammatory biomarkers.

There remains a need to identify effective treatments for viral infections.

In addition to viral infections, there are many inflammatory diseases which target the respiratory system, including chronic conditions such as asthma, COPD and cystic fibrosis. Not only do such conditions result in sufferers having a lower quality of life in many cases, but they also cause sufferers to be at a greater risk of becoming infected with, or suffering from complications arising from viral infections, such as those caused by coronaviruses, as well as secondary bacterial and fungal infections.

Asthma is the most common chronic disease among children and also affects millions of adults. It is estimated that some 235 million people worldwide suffer from this disease. COPD is a highly prevalent condition and a major cause of morbidity and mortality worldwide. As the disease progresses, patients with COPD may become prone to frequent exacerbations resulting in patient anxiety, worsening health status, lung function decline and increase in mortality rate. These episodes of worsening respiratory function lead to increases in health care utilization, hospital admissions and costs. Worse, frequent exacerbations are associated with a faster decline in lung function, thereby shortening life expectancy.

Current treatments for asthma and COPD include steroids and short- and long-acting beta antagonists. However, such treatments are associated with numerous side effects. Furthermore, they are not active against other conditions, such as secondary bacterial or viral infections.

Cystic fibrosis (CF) is a genetic disease that causes thick, adherent mucus to build up in the lungs, sinuses, digestive tract and pancreas. This mucus abnormality clogs airways and can cause life-threatening lung infections. Bacteria that do not adhere to normal mucus or tissues are removed by normal airway clearance mechanisms; however, the viscous mucus in CF patients limits mucociliary clearance and facilitates biofilm formation, initiating a cascade that includes dysregulated inflammation and ultimately end organ dysfunction.

Because of the reduced mucociliary clearance of CF patients, their lungs often succumb to bacterial infections. Topical, inhaled and systemic antibiotics are used to treat CF patient infections, but these drugs have often have limited effectiveness.

Thus, there remains a need to identify further treatments for inflammatory diseases, in particular diseases or the lungs and respiratory system.

There is also a need for new treatments for ocular conditions, including those associated with infection, such as a bacterial infection, an abnormal inflammatory response, and/or pre-corneal tear film dysfunction, such as dry eye disease (DED) (also called dry eye disorder or dry eye syndrome).

Dry eye disease (DED), also called keratoconjunctivitis sicca, is a common inflammatory ocular disease. Dry eye has been shown to be associated with abnormalities in the pre-corneal tear film and subsequent inflammatory changes in the entire ocular surface including the adnexa, conjunctiva and cornea (Hessen et al, J Ophthalmic Vis Res, 9(2): 240-250, 2014). Current medications include cyclosporine A, corticosteroids (e.g. dexamethasone), tacrolimus, tetracycline derivatives and autologous serum. A lot of these presently used anti-inflammatory agents such as cyclosporin can cause irritation in the patient's eye.

Infectious eye diseases, such as conjunctivitis, are often minor but in some cases can lead to very serious eye problems potentially causing permanent vision loss. Eye infections caused by a virus or bacteria can be treated with antibiotic or antiviral drops, ointment or oral medication. While such treatments may be effective in helping to fight the infection, they may not be effective in combating associated inflammation, discomfort or dryness.

Jabs et al, "Guidelines for the Use of Immunosuppressive Drugs in Patients with Ocular Inflammatory Disorders: Recommendations of an Expert Panel", Am J Ophthalmol, 130(4): 492-513, 2000, provide recommendations for the use of immunosuppressive drugs in the treatment of patients with ocular inflammatory disorders.

WO 2017/157997 A1 discloses non-aqueous topical compositions comprising a halogenated salicylanilide, such as niclosamide, and the use of such compositions in the topical treatment or prevention of an infection or disease caused by Gram-positive bacteria.

U.S. Pat. No. 4,742,083 suggests the use of certain substituted salicylamides as systemic analgesic agents and also for topical application as anti-inflammatory compositions.

BRIEF SUMMARY OF THE DISCLOSURE

According to a first aspect of the present invention there is provided a formulation comprising a halogenated salicylanilide, or a pharmaceutically acceptable salt thereof, and a cyclodextrin.

The halogenated salicylanilide may be selected from the group consisting of niclosamide, closantel, oxyclozanide and rafoxanide, or a pharmaceutically acceptable salt thereof. Preferably, the halogenated salicylanilide is niclosamide, or a pharmaceutically acceptable salt thereof.

In some embodiments, the niclosamide is present in the free-acid form. Alternatively, the formulation may comprise a pharmaceutically acceptable salt of niclosamide, preferably niclosamide ethanolamine.

The formulation may be in a form suitable for pulmonary administration. For example, it may be that the formulation is in the form of a solid (e.g. a powder).

In some embodiments the formulation is in the form of a suspension, a dispersion or a solution comprising the halogenated salicylanilide (e.g. niclosamide) or a pharmaceutically acceptable salt thereof, and a cyclodextrin in a pharmaceutically acceptable solvent. In other words, the formulation may be a liquid formulation. Solutions and suspensions comprising halogenated salicylanilide (e.g. niclosamide) or a pharmaceutically acceptable salt thereof, and a cyclodextrin, may be any of the solutions or suspensions as described herein.

The pharmaceutically acceptable solvent may comprise water, i.e. the solution or suspension may be an aqueous solution or an aqueous suspension. In some embodiments the solvent is water. In some embodiments, the solvent comprises a co-solvent. Certain co-solvents may be useful to aid solubilisation of the halogenated salicylanilide (e.g. niclosamide), or a pharmaceutically acceptable salt thereof, and/or the cyclodextrin, and/or to help stabilise the solution. In certain embodiments the co-solvent is selected from ethanol, propylene glycol, glycerol, polyethylene glycol (e.g. a polyethylene glycol (PEG) with an average molecular weight of less than 600, such as PEG 200, PEG 300 or PEG 400. In some embodiments the co-solvent is selected from propylene glycol and glycerol. In some embodiments the co-solvent is not a PEG. In some embodiments the co-solvent is not ethanol. In certain embodiments the co-solvents is DMSO. A co-solvent may be present in the formulation in an amount of from about 0% to about 20%, from about 0.1% to about 15%, from about 0.2% to about 12% by weight, from about 0.3% to about 10%, from about 0.4% to about 8%, from about 0.5% to about 6%, from about 0.6% to about 5%, from about 0.7% to about 4%, from about 0.8% to about 2%, from about 0.9% to about 1% by weight, based on the weight of the solution or suspension.

In certain embodiments the halogenated salicylanilide (e.g. niclosamide), or a pharmaceutically acceptable salt thereof, is present in the formulation an amount of about 0.01% to about 10% by weight of the formulation. For example, the halogenated salicylanilide (e.g. niclosamide) or a pharmaceutically acceptable salt thereof is present in an amount of 0.05% to 10%, 0.1% to 9%, 0.05% to 8%, 0.5% to 8%, 1% to 8%, 1.5% to 8%, 2% to 8%, 2.5% to 8%, 3% to 8%, 3.5% to 8%, 4% to 8%, 4.5% to 8%, 5% to 8%, 5.5% to 8%, 6% to 8%, 3% to 7%, 3.5% to 7.5%, 3.5% to 7%, 3.5% to 6.5%, 3.5% to 6%, 3.5% to 5.5%, 4% to 7%, 4% to 7%, 4% to 6.5%, 4% to 6%, 4% to 5.5%, 4.5% to 7%, 4.5% to 6.5%, 4.5% to 6.5% or 4.5% to 5.5% by weight of the formulation.

In some embodiments the halogenated salicylanilide (e.g. niclosamide) or a pharmaceutically acceptable salt thereof is present in the formulation in an amount of from about 0.05 to about 5%, from about 0.5 to about 4%, from about 0.1 to about 3%, from about 0.2 to about 2%, from about 0.5 to about 1.8%, from about 0.5 to about 1.5%, from about 0.8 to about 1.5%, from about 0.8 to about 1.2%, from about 0.9 to 1.1%, from about 1 to about 3% or from about 1.5 to about 2% by weight of a liquid formulation. Thus it may be that the halogenated salicylanilide (e.g. niclosamide) or a pharmaceutically acceptable salt is present in the liquid formulation in an amount of about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6% about 1.7%, about 1.8% about 1.9%, about 2%, about 2.1%, about 2.2%, about 2.3%, about 2.4%, about 2.5%, about 3%, about 4% or about 5% by weight of the liquid formulation. In a preferred embodiment the liquid formulation comprises about 1% by weight of the halogenated salicylanilide (e.g. niclosamide) or a pharmaceutically acceptable salt thereof. The amounts of the halogenated salicylanilide present in the liquid formulation is applicable to any of the formulations described herein, for example a solution comprising niclosamide or a pharmaceutically acceptable salt thereof; a suspension comprising niclosamide or a pharmaceutically acceptable salt thereof; an aerosol of a solution comprising niclosamide or a pharmaceutically acceptable salt thereof; or an aerosol of a suspension comprising niclosamide or a pharmaceutically acceptable salt thereof;

In certain embodiments the liquid formulations of the invention provide high concentrations of solubilised halogenated salicylanilide. In certain embodiments the halogenated salicylanilide (e.g. niclosamide), or a pharmaceutically acceptable salt thereof, is present in the liquid formulation at a concentration of from about 0.1 to about 100 mg/ml, from about 0.2 to about 90 mg/ml, from about 0.3 to about 80 mg/ml, from about 0.5 to about 75 mg/ml, from about 0.6 to about 70 mg/ml, from about 0.7 to about 65 mg/ml, from about 0.8 to about 60 mg/ml, from about 0.9 to about 60 mg/ml, or from about 1 to about 50 mg/ml. In some embodiments, the halogenated salicylanilide (e.g. niclosamide), or a pharmaceutically acceptable salt thereof, is present in the liquid formulation at a concentration of from about 2 to about 45 mg/ml, from about 3 to about 40 mg/ml, from about 4 to about 40 mg/ml, from about 4 to about 35 mg/ml, from about 5 to about 30 mg/ml, from about 5 to about 25 mg/ml, from about 5 to about 15 mg/ml, from about 7 to about 20 mg/ml, from about 7 to about 15 mg/ml, from about 8 to about 15 mg/ml, from about 9 to about 12 mg/ml, or from about 10 to about 11 mg/ml.

In some embodiments the halogenated salicylanilide (e.g. niclosamide) or a pharmaceutically acceptable salt thereof is present in the formulation in an amount of about 0.05 to 5% by weight of a solid formulation. Thus it may be that the halogenated salicylanilide (e.g. niclosamide) or a pharmaceutically acceptable salt is present in the solid formulation in an amount of about 0.05% to 10%, 0.05% to 8%, 0.5% to 8%, 1% to 8%, 1.5% to 8%, 2% to 8%, 2.5% to 8%, 3% to 8%, 3.5% to 8%, 4% to 8%, 4.5% to 8%, 5% to 8%, 5.5% to 8%, 6% to 8%, 3% to 7%, 3.5% to 7.5%, 3.5% to 7%, 3.5% to 6.5%, 3.5% to 6%, 3.5% to 5.5%, 4% to 7%, 4% to 7%, 4% to 6.5%, 4% to 6%, 4% to 5.5%, 4.5% to 7%, 4.5% to 6.5%, 4.5% to 6.5%, 4.5% to 6% or 5 to 5.5% by weight of the solid formulation. The amounts of the halogenated salicylanilide present in the solid formulation is applicable to any of the solid formulations described herein, for example a powder comprising niclosamide or a pharmaceutically acceptable salt thereof.

In some embodiments, the formulation is suitable for aerosol administration.

The cyclodextrin may be α-, β- or γ-cyclodextrin, or a derivative thereof. In some embodiments, the cyclodextrin is β-cyclodextrin, or a derivative thereof. In some embodiments, the cyclodextrin is 2-hydroxypropyl-β-cyclodextrin (HP-β-CD). In some embodiments the cyclodextrin is sulfobutylether-β-CD. In some embodiments the cyclodextrin is not sulfobutylether-β-CD.

In some embodiments the cyclodextrin is present in an amount of about 1% to about 90% by weight of the formulation. For example, the cyclodextrin may be present in an amount of from about 5% to about 85%, from about 10% to about 80% or from about 20 to about 70% by weight, based on the weight of the formulation.

In certain embodiments the cyclodextrin is present in an amount of about 1% to about 60% by weight of a liquid formulation. In certain embodiments the cyclodextrin is present in an amount of more than about 5%, more than about 6%, more than about 7%, more than about 8%, more than about 9%, more than about 10%, more than about 11%, more than about 12%, more than about 13%, more than about 14% or more than about 15% by weight of a liquid formulation. In certain embodiments the cyclodextrin is present in an amount of about 1% to about 25% by weight of a liquid formulation. For example, the cyclodextrin is present in an amount of 2% to 24%, 3% to 23%, 4% to 22%, 5% to 21%, 6% to 20%, 7% to 19.5%, 8% to 19%, 9% to 18.5%, 10% to 18%, 10.5% to 17.5%, 11% to 17%, 11.5% to 16.5%, 12% to 16%, 12.5% to 15.5%, 13% to 15% or 13.5 to 14.5%, by weight of the liquid formulation. In certain embodiments the cyclodextrin is present in an amount of about 10%, about 10.5%, about 11%, about 11.5%, about 12%, about 12.5%, about 13%, about 13.5%, about 14%, about 14.1%, about 14.2%, about 14.3%, about 14.4%, about 14.5%, about 14.6%, about 14.7%, about 14.8%, about 14.9%, about 15%, about 15.1%, about 15.2%, about 15.3%, about 15.4%, about 15.5%, about 15.6%, about 15.7%, about 15.8%, about 15.9%, about 16%, about 16.5% about 17%, about 17.5% or about 18%, by weight of the liquid formulation.

In a preferred embodiment the cyclodextrin is present in the liquid formulation in an amount of about 14.5% to 15.5% by weight of the liquid formulation.

In certain embodiments the cyclodextrin is present in an amount of about 50% to about 95% by weight of a solid formulation. For example, the cyclodextrin may be present in an amount of from about 55% to about 90%, from about 60% to about 85%, from about 65% to about 80% or from about 70% to about 75% by weight, based on the weight of the solid formulation.

In some embodiments the liquid formulation comprises from about 0.1% to about 1.5% by weight of niclosamide ethanolamine and from about 10% to about 20% by weight of cyclodextrin (e.g. HP-β-CD).

In some embodiments the liquid formulation comprises from about 0.1% to about 1.5% by weight of niclosamide ethanolamine and from about 12% to about 20% by weight of cyclodextrin (e.g. HP-β-CD). In a preferred embodiment the liquid formulation comprises about 1% by weight of niclosamide ethanolamine and about 15% by weight of cyclodextrin (preferably HP-β-CD).

At least a portion of the halogenated salicylanilide (e.g. niclosamide), or a pharmaceutically acceptable salt thereof may form a complex with the cyclodextrin. In some embodiments, from about 20 to about 100%, from about 30% to about 90%, from about 40% to about 80% or from about 50% to about 70% of the halogenated salicylanilide (e.g. niclosamide), or a pharmaceutically acceptable salt thereof, or the pharmaceutically acceptable salt thereof, is complexed with the cyclodextrin.

In some embodiments the ratio of halogenated salicylanilide (e.g. niclosamide), or a pharmaceutically acceptable salt thereof, to cyclodextrin is from 1:250 to 5:1, from 1:200 to 4:1, from 1:150 to 3:1, from 1:100 to 2:1, from 1:50 to 1:1, from 1:30 to 1:2, from 1:20 to 1:3, from 1:20 to 1:8, from 1:20 to 1:12, from 1:18 to 1:12, from 1:15 to 1:4 or from 1:10 to 1:5.

In some embodiments, the formulation comprises at least one stabilizer. Suitable stabilizers include polymers, emulsifiers, surfactants and combinations thereof. In some embodiments the stabilizer comprises a polymer. Suitably the polymer is a water soluble polymer, preferably a polymer that is soluble in water at the pH of the liquid formulations disclosed herein. Advantageously, the addition of a polymer may improve the stability of a solution comprising a halogenated salicylanilide (e.g. niclosamide), or a pharmaceutically acceptable salt thereof, and a cyclodextrin. Without being bound by theory, it is thought that the presence of the stabilizer (e.g. polymer) may aid complex formation between the halogenated salicylanilide and cyclodextrin, and thus may also assist in preparing the formulation. Additionally or alternatively, the stabilizer (e.g. polymer) may help to inhibit crystallisation and subsequent precipitation of the solubilised halogenated salicylanilide. Accordingly formulations comprising a stabilizer such as a polymer may provide high concentration of solubilised halogenated salicylanilide in the formulations of the invention. The polymer may be selected from the group consisting of polyvinylpyrrolidone (PVP), polyvinylalcohol (PVA), hydroxypropylcellulose (HPC), poloxamers, hydroxypropylmethylcellulose (HPMC), hydroxypropylmethylcellulose acetate succinate (HPMC-AS), polyvinylpyrrolidone/vinyl acetate copolymer (PVP/VA) and any combination thereof. Preferably, the polymer comprises PVP. As is known in the art, PVP is available in several viscosity grades, ranging from low to high molecular weight. Available PVP grades include K-12, K-15, K-17, K-30, K-60, K-80, K-85, K-90 and K-120. In some embodiments, the formulation comprises PVP K-12, K-15, K-17 or K-30. The K-value refers to the Fikentscher K value and may be determined by measuring the viscosity of a 1% wt./vol pf the PVP in water using Ostwald-Fenske or Cannon-Fenske capillary viscometer and calculating the K-value, for example using the method described in ISO 1628-1:2009. In some embodiments, the polymer is PVP/VA. As is known in the art, PVP/VA copolymers are available in different ratios of vinylpyrrolidone to vinyl acetate. The weight ratio of PVP:VA may be 70:30, 60:40, 50:50, 40:60 or 30:70. In some embodiments, the ratio is 60:40 (e.g. available as Kollidon® VA 64).

The polymer may be present in the formulation in an amount of from about 0.01% to about 20%, from about 0.05% to about 18%, from about 0.1% to about 15%, from about 0.5% to about 13%, from about 0.8% to about 12%, from about 1% to about 10%, from about 2% to about 8% or from about 3% to about 6% by weight based on the weight of the formulation.

For example, the polymer may be present in a liquid formulation in an amount of from about 0.01% to about 10%, from about 0.05% to about 8%, from about 0.1% to about 6%, from about 0.1% to about 5%, from about 0.1% to about 4%, from about 0.1% to about 3%, from about 0.5% to about 5%, from about 0.5% to about 4%, from about 0.5% to about 3%, from about 0.8% to about 3%, from about 1% to about 4%, from about 1% to about 3%, from about 1% to about 2.5%, or from about 1% to about 2% by weight based on the weight of the liquid formulation. Thus it may be that the polymer is present in a liquid formulation in an amount of about 0.5%, about 0.6%, about 0.7%, about 0.8%, about 0.9%, about 1% about 1.1%, about 1.2%, about 1.3%, about 1.4%, about 1.5%, about 1.6%, about 1.7%, about 1.8%, about 1.9%, about 2% about 2.1%, about 2.2%, about 2.3%, about 2.4%, about 2.5%, about 2.6%, about 2.7%, about 2.8%, about 2.9%, about 3%, about 3.5%, about 4%, about 4.5% or about 5% by weight based on the weight of the liquid formulation.

The polymer may be present in a solid formulation in an amount of from about 1% to about 20%, from about 2% to about 18%, from about 3% to about 16%, from about 5% to about 14%, from about 5% to about 12%, from about 6% to about 11%, from about 7% to about 10% or from about 8 to about 9% by weight, based on the weight of the solid formulation.

In some embodiments the formulation further comprises a preservative. Suitable preservatives include benzalkonium chloride.

The preservative may be present in an amount of from about 0 to about 0.2%, from about 0.002% to about 0.15%, from about 0.004 to about 0.1%, from about 0.006% to about 0.05%, or from about 0.008% to about 0.02% by weight (e.g. about 0.01 wt. %), based on the weight of the formulation.

In some embodiments the formulation further comprises a buffer and/or a stabilising agent. Suitable buffers and stabilising agents include disodium edetate, disodium phosphate, polysorbate 80, sodium dihydrogen phosphate, sodium citrate, sodium phosphate, sodium acetate, acetic acid, histidine lactic acid, aspartic acid, tartaric acid, glutamic acid, succinic acid, malic acid, trometamine, lactic acid, histidine, fumaric acid and citric acid. Preferably the stabilising agent comprises disodium edetate.

The stabilising agent may be present in an amount of from about 0 to about 2% by weight, for example from about 0.02% to about 1%, from about 0.04% to about 0.6%, from about 0.06% to about 0.4%, or from about 0.08% to about 0.2% by weight (e.g. 0.1 wt. %), based on the weight of the formulation.

In some embodiments the formulation further comprises an electrolyte. Suitable electrolytes include sodium chloride, potassium chloride, sodium dihydrogen phosphate or potassium dihydrogen phosphate. Preferably the electrolyte is sodium chloride.

The electrolyte may be present in an amount of from about 0% to about 10%, from about 0.1% to about 8%, from about 0.2% to about 5%, from about 0.3 to about 2%, from about 0.4 to about 1%, or from about 0.5 to about 0.8% by weight, based on the weight of the formulation.

In some embodiments the formulation has a viscosity of from 1 to 150 cP, from 1.5 to 100, from 2 to 50 cP or from 5 to 25 cP. In some embodiments, the formulation has a viscosity of no greater than 20, no greater than 15, or no greater than 10 cP. For example, the viscosity may be from 1 to 10, from 1.5 to 9.5, from 2 to 8, from 2.5 to 7.5, from 3 to 7, from 3.5 to 6.5, from 4 to 6 or from 5.5 to 6.5 cP In some embodiments the formulation has a pH of from 4 to 9, for example from 5 to 8.5, from 7 to 8.5, or from 6 to 8, e.g. from 4 to 8, from 7 to 8.2, from 7.5 to 8.2, from 7.5 to 7.8, or preferably from 7.6 to 8.

In some embodiments the formulation comprises a pH modifier. Suitable pH modifiers include acids (e.g. hydrochloric acid, acetic acid, lactic acid, citric acid, tartaric acid, malic acid, formic acid, uric acid) and bases (e.g. sodium hydroxide, potassium hydroxide, calcium hydroxide, sodium or potassium carbonate, sodium or potassium bicarbonate). In some embodiments, the formulation comprises at multiple (e.g. 2, 3 or 4) pH modifiers. For example, the formulation may comprise two different acids, or two different bases, or an acid and a base. In some embodiments, the formulation comprises sodium hydroxide and hydrochloric acid.

In some embodiments the formulation has an osmolarity of from 5 to 500 mOsmol/L, from 100 to 400 mOsmol/L, or from 150 to 350 mOsmol/L, for example from 180 to 320 mOsmol/L, from 250 to 350 mOsmol/L, from 280 to 330 mOsmol/L, from 290 to 320 mOsmol/L, or from 200 to 250 mOsmol/L.

In some embodiments the halogenated salicylanilide is niclosamide, or a pharmaceutically acceptable salt thereof. In some embodiments the halogenated salicylanilide is niclosamide. In some embodiments the halogenated salicylanilide is a pharmaceutically acceptable salt of niclosamide. In some embodiments the halogenated salicylanilide is niclosamide ethanolamine.

According to a second aspect of the present invention, there is provided a formulation comprising a halogenated salicylanilide (e.g. niclosamide), or a pharmaceutically acceptable salt thereof, and a cyclodextrin, for use as a medicament. The formulation may be any of the formulations described herein.

According to a third aspect of the present invention, there is provided a formulation comprising a halogenated salicylanilide (e.g. niclosamide), or a pharmaceutically acceptable salt thereof, and a cyclodextrin, for use in the treatment or prevention of an infectious disease or an inflammatory disease in a subject in need thereof. The formulation may be any of the formulations described herein.

According to a fourth aspect of the present invention, there is provided a formulation comprising a halogenated salicylanilide (e.g. niclosamide), or a pharmaceutically acceptable salt thereof, and a cyclodextrin, for use in the treatment or prevention of an ocular condition or disease in a subject. The formulation may be any of the formulations described herein.

Also provided is a method of treating or preventing an infectious disease, an inflammatory disease or an ocular disease or condition in a subject, the method comprising administering to the subject a therapeutically effective amount of a formulation comprising a halogenated salicylanilide (e.g. niclosamide), or a pharmaceutically acceptable salt thereof, and a cyclodextrin. The formulation may be any of the formulations described herein.

The formulation may be used for the topical treatment or prevention of the infectious disease, inflammatory disease or ocular disease or condition.

The formulation for use as a medicament, or for use in the treatment or prevention of an infectious, inflammatory or ocular disease may be any formulation as defined herein.

In some embodiments, the infectious disease is a viral, bacterial, or fungal infection.

In some embodiments, the infectious disease is a viral infection. The viral infection may be a pulmonary viral infection.

In certain embodiments the viral infection may be caused by or associated with a virus selected from respiratory syncytial virus, influenza virus, parainfluenza virus, human metapneumovirus, severe acute respiratory syndrome coronavirus (SARS-CoV), severe acute respiratory syndrome coronavirus (SARS-CoV-2), Middle East respiratory syndrome coronavirus (MERS-CoV), a human rhinovirus (HRVs) and human adenovirus (HAdV).

In certain embodiments the viral infection is caused by or associated with a Pneumoviridae virus, for example a Human respiratory syncytial virus (HRSV) (e.g. HRSV-A2, HRSV-B1 or HRSV-S2).

In certain embodiments the viral infection is caused by or associated with a Coronaviridae virus. In certain embodiments the viral infection is caused by or associated with a virus is selected from Alphacoronavirus, Betacoronavirus, Gammacoronavirus and Deltacoronavirus. Preferably the viral infection is caused by or associated with a Betacoronavirus. Thus is certain embodiments the viral infection is caused by or associated with a virus is selected from severe acute respiratory syndrome coronavirus (SARS-CoV), severe acute respiratory syndrome coronavirus 2 (SARS-CoV-2), Middle East respiratory syndrome coronavirus (MERS-CoV), HCoV-229E, HCoV-NL63, HCoV-0C43 and HCoV-HKU1.

In a particular embodiment the viral infection is caused by or associated with SARS-CoV-2. This it may be that the viral infection is COVID-19.

In some embodiments the viral infection is caused by or associated with an influenza virus.

The viral infection may also be caused by or associated with a virus selected from Flaviviridae (e.g. Zika virus (ZIKV), dengue (e.g. DENV 1-4), West Nile virus (WNV), yellow fever virus (YFV), and Japanese encephalitis virus (JEV), Hepatitis C virus (HCV), Filoviridae (e.g. Ebolavirus)), Togaviridae (e.g. Alphaviruses such as Chikungunya virus (CHIKV)), and Adenoviridae (e.g. Human adenoviruses (HAdVs)).

In some embodiments, the viral infection is associated with inflammation. In such embodiments, the treatment may result in a decrease in mucus production and/or secretion, a decrease in bronchoconstriction, repression of pro-inflammatory cytokines, modulation of the activity of dendritic cells, and/or inhibition of STAT3.

In some embodiments, the viral infection is associated with a secondary bacterial infection. A secondary bacterial infection may be caused by a bacterium selected from the group consisting of *S. aureus, S. pneumoniae, H. influenzae, M. catarrhalis, S. pyogenes* and *N. gonorrhoea*.

The inflammatory disease may be a pulmonary inflammatory disease.

In some embodiments, the pulmonary inflammatory disease is selected from the group consisting of: asthma, cystic fibrosis, chronic obstructive pulmonary disease (COPD), pulmonary fibrosis, pneumonia, interstitial lung disease, sarcoidosis, bronchiolitis obliterans, pneumonitis, and acute respiratory distress syndrome (ARDS).

The formulation may be administered by inhalation intraorally or intranasally. In some embodiments the formulation is administered by inhalation intraorally. In certain embodiments, the formulation is administered in the form of an aerosol.

In some embodiments the formulation is administered intranasally. It will be understood that "intranasal" administration means administration into the nasal cavity, i.e. through the nose. Intranasal administration encompasses both administration of the formulation to the nasal mucosa and the upper respiratory tract, and administration of the formulation to the lower respiratory tract (e.g. via inhalation).

Recent research has identified a gradient of expression levels of the human angiotensin-converting enzyme (ACE)-2, which is targeted by SARS-CoV-2, from the nasal tissues (high expression) and the distal intrapulmonary regions (low expression). This expression pattern was found to be mirrored by a gradient of SARS-CoV-2 infectivity which was high in the nasal epithelium and markedly reduced in the distal lung (bronchioles, alveoli). In light of these findings, it has been suggested that the nasal surfaces may be the dominant initial site of SARS-CoV-2 infection (Hou et al., "SARS-CoV-2 Reverse Genetics Reveals a Variable Infection Gradient in the Respiratory Tract", Cell, 2020). Intranasal administration may therefore be beneficial to subjects suffering from mild COVID-19, or those in the early stages of disease, prior to progression to the later stages of the disease which are characterised by pulmonary inflammation. In some embodiments, subjects whose symptoms include a loss of taste and/or smell, and/or ocular symptoms (e.g. one or more of conjunctival hyperemia, chemosis, epiphora, or increased secretions) may be treated via intranasal administration of the formulation of the invention. Intranasal administration may also be beneficial for treating asymptomatic subjects, for prophylactic treatment of high risk populations as identified herein (e.g. healthcare professionals, or those with underlying conditions), for treating subjects suspected of having contracted SARS-CoV-2, and/or for treating close contacts of a person with COVID-19.

In some embodiments, the formulation is administered both intranasally and intraorally (e.g. via inhalation). Thus it may be that a first formulation comprising a halogenated salicylanilide (e.g. niclosamide), or a pharmaceutically acceptable salt thereof, and a cyclodextrin described herein is administered by inhalation intraorally (e.g. as an aerosol) separately, sequentially or simultaneously with a second formulation comprising a halogenated salicylanilide (e.g. niclosamide), or a pharmaceutically acceptable salt thereof, and a cyclodextrin described herein, wherein the second formulation is administered intranasally (e.g. as spray). It may be that the first and second formulations are different. It may be that the first and second formulations are the same.

Subjects with pulmonary viral infections may be prone to coughing when drugs are administered by inhalation. This can make administration of the drug difficult and/or may reduce the dose of drug delivered to the airway and lungs. In certain embodiments the subject is treated with niclosamide is administered an antitussive agent prior to or concurrently with the inhaled niclosamide, or a pharmaceutically acceptable salt thereof. Thus it may be that the subject is treated with antitussive agent is selected from codeine, dextromethorphan, hydrocodone, methadone, butorphanol, benzonatate, ethylmorphine, oxeladin, pipazethate, pholcodine, noscapine, butamirate and a local anaesthetic (e.g. lidocaine) prior to or concurrently with the inhaled administration of the niclosamide or a pharmaceutically acceptable salt thereof. Preferably the subject is treated with the antitussive agent prior to administration of the niclosamide or pharmaceutically acceptable salt thereof to reduce or eliminate coughing associated with the inhaled administration of the niclosamide. Thus it may be that the subject is treated with a local anaesthetic prior to or concurrently with the inhaled administration of the niclosamide or a pharmaceutically acceptable salt thereof. Suitably the local anaesthetic is administered so halogenated salicylanilide as to provide a local anaesthetic effect in the oral cavity and/or airways. Thus it maybe that the local anaesthetic is administered by inhalation or as a gel or liquid to the oral and/or nasal cavity. Suitably the local anaesthetic is lidocaine.

The halogenated salicylanilide (e.g. niclosamide), or a pharmaceutically acceptable salt thereof, may be administered to the subject in a unit dosage of from about 10 mg to about 1000 mg based on the weight of the halogenated salicylanilide or salt thereof (for example from about 100 mg to about 600 mg, preferably about 150 mg to about 500 mg, based on the weight of the halogenated salicylanilide or salt thereof.

The halogenated salicylanilide (e.g. niclosamide), or a pharmaceutically acceptable salt thereof, may be administered to the subject one to five times per day, for example from 1 to 4 times per day, e.g. 2 or 3 times per day.

In some embodiments, the ocular disease or condition is selected from the group consisting of: an infectious ocular disease, dry eye disease (DED), allergic disease (such as allergic conjunctivitis), blepharitis or an inflammatory eye disease (such as ocular rosacea).

In some embodiments, the infectious ocular disease is selected from the group consisting of conjunctivitis (including bacterial, fungal and viral conjunctivitis), keratitis (including viral, bacterial, fungal, amoebic and parasitic keratitis), endophthalmitis, blepharitis, sty, uveitis, cellulitis (e.g. bacterial cellulitis) and ocular herpes.

In some embodiments the ocular condition or disease is bacterial conjunctivitis. The bacterial conjunctivitis may be caused by a bacteria selected from the group consisting of *S. aureus* (including MRSA), *S. pneumoniae, H. influenzae, P. aeruginosa, M. catarrhalis* and *N. gonorrhoeae*.

In some embodiments the ocular condition or disease is viral conjunctivitis. The viral conjunctivitis may be caused by adenovirus.

Wu et al. (Characteristics of Ocular Findings of Patients With Coronavirus Disease 2019 (COVID-19) in Hubei Province, China. JAMA Ophthalmol. 2020 May 1; 138(5)) has identified that some patients infected with SARS-CoV-2 exhibit ocular symptoms, and that these symptoms often appeared at the early stages of infection. Accordingly it may be that the liquid formulation is for use in a method of treatment or prevention of a viral infection in a subject (e.g. SARS-CoV-2, the method comprising ocular administration of the liquid formulation to the subject.

Treatment or prevention of an ocular disease or condition may comprise administering a liquid formulation comprising a halogenated salicylanilide (e.g. niclosamide), or a pharmaceutically acceptable salt thereof, and a cyclodextrin, for example a formulation as described herein, topically to one or both eyes. The liquid formulation may comprise an ophthamically acceptable carrier.

In some embodiments, the liquid formulation is administered to one or both eyes of the subject one to five times per day, for example from 1 to 3 times per day, e.g. 2 times per day.

Another aspect of the invention provides an aerosol of a solution comprising a halogenated salicylanilide (e.g. niclosamide), or a pharmaceutically acceptable salt thereof, and a cyclodextrin. Thus it may be that the aerosol is an aerosol of a solution comprising a halogenated salicylanilide (e.g. niclosamide), or a pharmaceutically acceptable salt thereof, and a cyclodextrin. The aerosol may be an aerosol of any of the liquid formulations or solutions as described herein. For example, an aerosol of any of the solutions comprising niclosamide (e.g. niclosamide ethanolamine) and a cyclodextrin (e.g. HP-β-CD) disclosed herein. Suitably the solution is an aqueous solution.

Also provided is a unit dosage comprising a solution of a halogenated salicylanilide (e.g. niclosamide), or a pharmaceutically acceptable salt thereof, and a cyclodextrin, wherein the halogenated salicylanilide (e.g. niclosamide) is present in an amount of from about 0.1 mg to about 200 mg, for example from about 0.5 mg to about 100 mg or from about 1 mg to about 50 mg, based on the weight of the halogenated salicylanilide (e.g. niclosamide). The solution may be any of the solutions comprising a halogenated salicylanilide (e.g. niclosamide), or a pharmaceutically acceptable salt thereof, and a cyclodextrin as described herein. For example, the solution may be any of the solutions comprising niclosamide ethanolamine and a cyclodextrin (e.g. HP-β-CD) as disclosed herein. Suitably the solution is an aqueous solution. The unit dosage is suitably present in a container, for example a vial, blister pack, bottle (e.g. a nasal spray), syringe (e.g. as part of an intranasal delivery device) or reservoir within an inhaler device (e.g. a nebulizer). In embodiments wherein the formulation is in the form of a solution, the unit dosage volume administered to the subject may be from 1 to 10 ml, from 2 to 9 ml, from 3 to 8 ml or from 4 to 6 ml. In some embodiments, the unit dosage volume administered to the subject is from 10 µl to 10 ml, from 20 µl to 8 ml, from 30 µl to 6 ml, from 40 µl to 5 ml, from 50 µl to 2 ml, from 100 µl to 1 ml, from 120 µl to 0.8 ml, from 130 µl to 0.7 ml, from 140 µl to 0.6 ml, from 150 µl to 0.5 ml or from 200 µl to 400 µl. In some embodiments, the unit dosage volume administered to the subject is from 100 to 200 µl, from 110 to 190 µl, from 120 to 180 µl, from 130 to 170 µl, from 140 to 160 µl or from 150 to 155 µl. It will be appreciated that the mass of the halogenated salicylanilide (e.g. niclosamide), or a pharmaceutically acceptable salt thereof, administered for a given volume will depend on the concentration of the solution. In some embodiments, the halogenated salicylanilide (e.g. niclosamide), or a pharmaceutically acceptable salt thereof, is present in the solution in an amount of from about 0.01% to about 10% by weight. Preferably the solution comprises about 1% by weight of niclosamide ethanolamine. The volume may be administered one or more times per day, for example once per day, twice per day, three times per day or four times per day. It may be that the volume is administered once or twice per day. It may be that the volume is administered once per day. It may be that the volume is administered twice per day.

In some embodiments wherein a solution of the invention is administered intranasally, the volume administered to the subject may be from 50 to 500 µl, from 100 to 400 µl, from 150 to 300 µl or from 200 to 250 µl. It will be appreciated that approximately half of the volume should be administered to each nostril. In some embodiments, from about 50 to about 150 µl is administered to each nostril (i.e. about 100 to about 300 µl in total). In some embodiments, a volume of about 130 µl-150 µl (e.g. 140 µl) is administered to each nostril (i.e. about 260-300 µl, e.g. 280 µl, in total). Preferably the solution administered intranasally comprises about 1% by weight of niclosamide ethanolamine. The volume may be administered intranasally one or more times per day, for example once per day, twice per day, three times per day or four times per day. It may be that the volume is administered intranasally once or twice per day. It may be that the volume is administered intranasally once per day. It may be that the volume is administered intranasally twice per day.

It will further be appreciated that in some embodiments wherein a solution of the invention is administered both intraorally (i.e. via inhalation) and intranasally, the total volume administered to the subject will be the sum of the volume administered intraorally and the volume administered intranasally. The total volume may be from 10 µl to 10 ml, from 20 µl to 8 ml, from 30 µl to 6 ml, from 40 µl to 5 ml, from 50 µl to 2 ml, from 100 µl to 1 ml, from 150 µl to 0.5 ml or from 200 µl to 400 µl. Preferably the solution administered intranasally comprises about 1% by weight of niclosamide ethanolamine. As will be appreciated, when the solution is administered both intraorally and intranasally the volume administered intranasally may be the same or different to the volume administered intranasally. Similarly the frequency of the intraoral and intranasal administration may be the same or different. For example, the intraoral and intranasal doses may be administered sequentially (e.g. the intraoral administration followed shortly (e.g. within 10 minutes) by the intranasal administration, or vice versa. In certain embodiments the intraoral and intranasal doses may be administered separately (e.g. where the intraoral dosing is separated from the intranasal dosing by more than 10 minutes (e.g. by more than one hour). Also contemplated is substantially simultaneous intraoral and intranasal administration. It may be that the volume administered intranasally is administered once or twice per day. It may be that the volume administered intraorally is administered once or twice per day.

As mentioned above, some subjects infected with SARS-CoV-2 present with ocular symptoms, for example conjunctival hyperemia, chemosis, epiphora, or increased ocular secretions. Thus ocular administration (e.g. topically) of a formulation of the invention may be effective in preventing or treating SARS-CoV-2. Also contemplated is ocular administration together with intraoral and/or intranasal administration of a formulation of the invention. Accordingly in certain embodiments a formulation of the invention is administered to the subject intraorally (e.g. as topically applied eye drops), intranasally and intraorally by inhalation.

Also provided is a system comprising a container comprising: a formulation comprising a halogenated salicylanilide (e.g. niclosamide), or a pharmaceutically acceptable salt thereof, and a cyclodextrin; and an inhaler device. The formulation may be a formulation as defined herein.

Also provided is a kit comprising a container comprising a formulation comprising a halogenated salicylanilide (e.g. niclosamide), or a pharmaceutically acceptable salt thereof, and a cyclodextrin; and an inhaler device.

In certain embodiments the formulation comprising a halogenated salicylanilide (e.g. niclosamide), or a pharmaceutically acceptable salt thereof and a cyclodextrin is present in the system or kit is in the form of a powder, a solution, a suspension, for example any of the formulations described herein. Suitably the formulation is in the form of an aqueous solution.

In certain embodiments the inhaler device of the system or kit is adapted to aerosolize a solution or suspension comprising a halogenated salicylanilide (e.g. niclosamide), or a pharmaceutically acceptable salt thereof and a cyclodextrin. Suitably the inhaler device is adapted to deliver the aerosolized solution or suspension intranasally or intraorally to a subject.

In certain embodiments the inhaler device of the system or kit is a nebulizer selected from a jet nebulizer, a vibrating mesh nebulizer, an ultrasonic nebulizer or a pressurised metered dose inhaler (pMDI).

Also provided is a system comprising a container comprising: a formulation comprising a halogenated salicylanilide (e.g. niclosamide), or a pharmaceutically acceptable salt thereof, and a cyclodextrin; and an intranasal delivery device. The formulation may be a formulation as defined herein.

Also provided is a kit comprising a container comprising a formulation comprising a halogenated salicylanilide (e.g. niclosamide), or a pharmaceutically acceptable salt thereof, and a cyclodextrin; and an intranasal delivery device.

Further provided is a container containing the formulation comprising a halogenated salicylanilide (e.g. niclosamide), or a pharmaceutically acceptable salt thereof and a cyclodextrin. The formulation may be as described herein. In some embodiments the formulation comprises an ophthamically acceptable carrier.

The formulation may be in the form of a liquid. Conveniently, the container may be configured to dispense droplets of the formulation to the eye.

In a further aspect, there is provided a method of preparing a formulation, the method comprising:
- adding cyclodextrin and/or a halogenated salicylanilide (e.g. niclosamide), or a pharmaceutically acceptable salt thereof, to a solvent to form a suspension;
- heating (or continuing to heat) the suspension to a temperature of less than 120° C. for a period of time sufficient for the cyclodextrin and/or a halogenated salicylanilide (e.g. niclosamide), or a pharmaceutically acceptable salt thereof, to dissolve in the solvent, thereby forming a solution; and
- cooling the solution.

In some embodiments, both the cyclodextrin and the halogenated salicylanilide (e.g. niclosamide), or a pharmaceutically acceptable salt thereof, are added to the solvent prior to heating.

In some embodiments, the solvent is heated prior to the addition of the cyclodextrin and the halogenated salicylanilide. In such embodiments, after addition of the cyclodextrin and/or halogenated salicylanilide to the solvent to form a suspension, heating may be continued such that the temperature of the suspension is maintained.

In some embodiments the method comprises:
- adding one of cyclodextrin and halogenated salicylanilide (e.g. niclosamide), or a pharmaceutically acceptable salt thereof, to the solvent to form a suspension;
- heating (or continuing to heat) the suspension to a temperature of less than 120° C. for a period of time sufficient for the cyclodextrin or halogenated salicylanilide (e.g. niclosamide), or a pharmaceutically acceptable salt thereof, to dissolve in the solvent, thereby forming a first solution;
- adding the other of cyclodextrin and halogenated salicylanilide (e.g. niclosamide), or a pharmaceutically acceptable salt thereof, to the first solution in the form of a solid;
- heating (or continuing to heat) the first solution to a temperature of less than 120° C. for a period of time sufficient for the solid to dissolve, thereby forming a second solution; and
- cooling the solution.

In some embodiments, the method comprises:
- adding cyclodextrin to a solvent to form a first suspension, and heating (or continuing to heat) the first suspension to a temperature of less than 120° C., such as 25 to 100° C., for a period of time sufficient for the cyclodextrin to dissolve in the solvent, thereby forming a first solution;
- adding halogenated salicylanilide (e.g. niclosamide), or a pharmaceutically acceptable salt thereof, to a solvent to form a second suspension, and heating (or continuing to heat) the second suspension to a temperature of less than 120° C., such as 25 to 100° C., for a period of time sufficient for the halogenated salicylanilide (e.g. niclosamide), or a pharmaceutically acceptable salt thereof, to dissolve in the solvent, thereby forming a second solution;
- adding the first solution to the second solution to form a mixture; and
- cooling the mixture.

In some embodiments in any of the methods described herein the pH of the solvent, solution or suspension is adjusted to a pH of 7 or greater (e.g. 8 to 12). A high pH has been found to aid formation of an inclusion complex between the cyclodextrin and the niclosamide or a pharmaceutically acceptable salt thereof. In certain embodiments the pH of the solvent, solution or suspension is adjusted to a pH of 8 or greater.

In some embodiments the pH is adjusted to a pH of 7 or greater (e.g. a pH of 8 or greater, such as a pH of 8 to 12) prior to the addition of the halogenated salicylanilide. The pH may be adjusted by adding a base (e.g. NaOH).

In some embodiments in any of the methods described herein the suspension further comprises a water-soluble polymer (e.g. PVP). The presence of a polymer such as PVP has been found to enhance the an inclusion complex between the cyclodextrin and the niclosamide or a pharmaceutically acceptable salt thereof and enables high concentration aqueous solutions of niclosamide, or a pharmaceutically acceptable salt thereof to be prepared. Thus, in some embodiments, the method comprises adding a water-soluble polymer (e.g. PVP) to the solution or suspension. In some embodiments, the water-soluble polymer is added to the second solution.

In some embodiments, the method comprises heating (or continuing to heat) the mixture at a temperature of less than 120° C., after adding the first solution to the second solution, prior to cooling. Heating may be carried out to a temperature of from 25 to around 120, e.g. 50 to 120° C.

In some embodiments, cooling is carried out to a temperature of from 10 to 40° C.

In some embodiments the solvent is an aqueous solvent. Suitably the solvent is substantially free from volatile organic solvents (e.g. ethanol). Preferably the solvent is water.

In preferred embodiments of the methods described herein the halogenated salicylanilide is niclosamide ethanolamine.

Figure 1B:
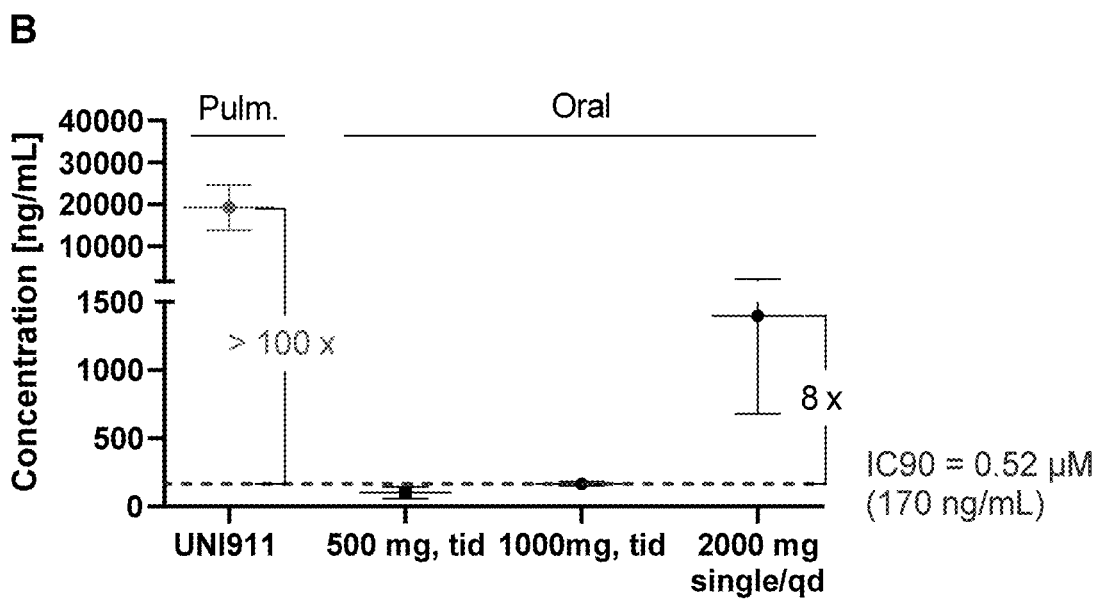
Figure 2A:
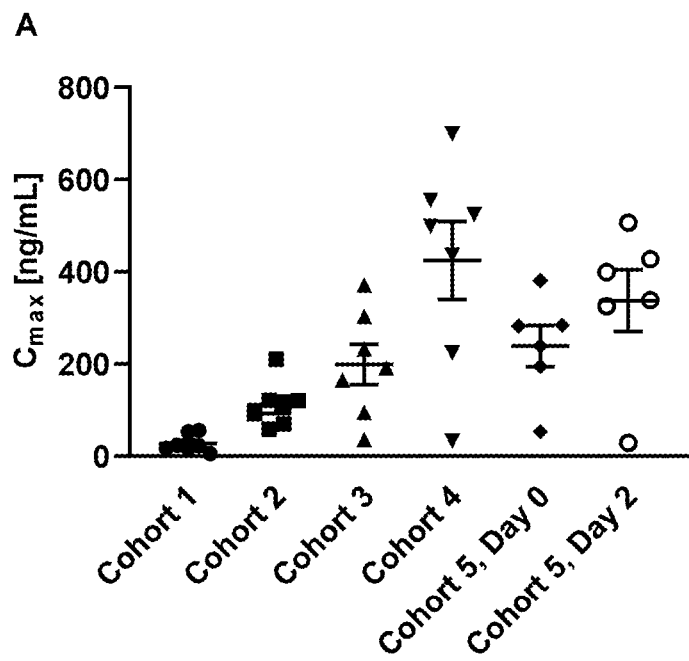
Figure 2B:
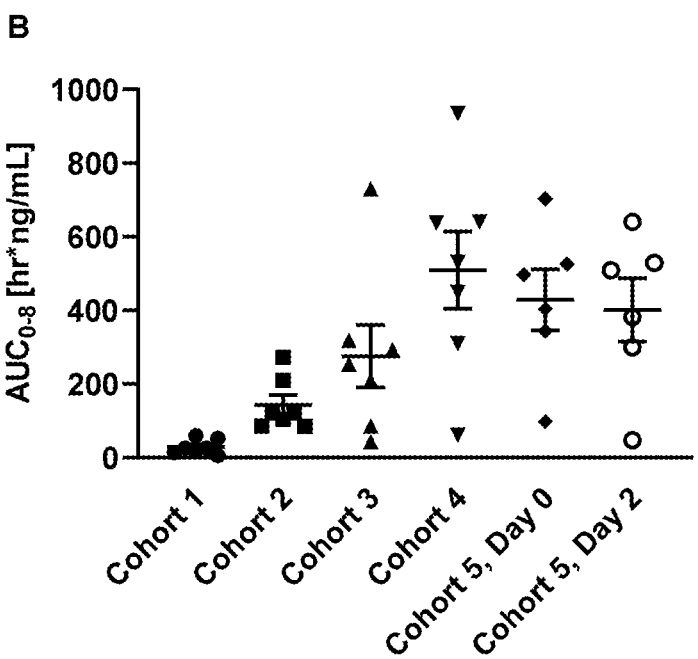
Figure 3:
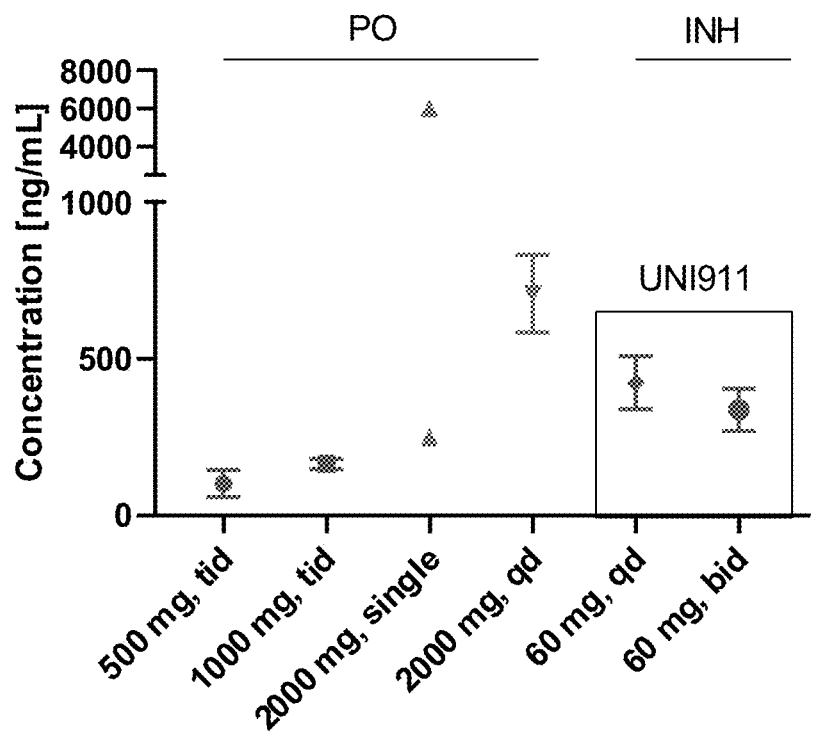
Figure 4:
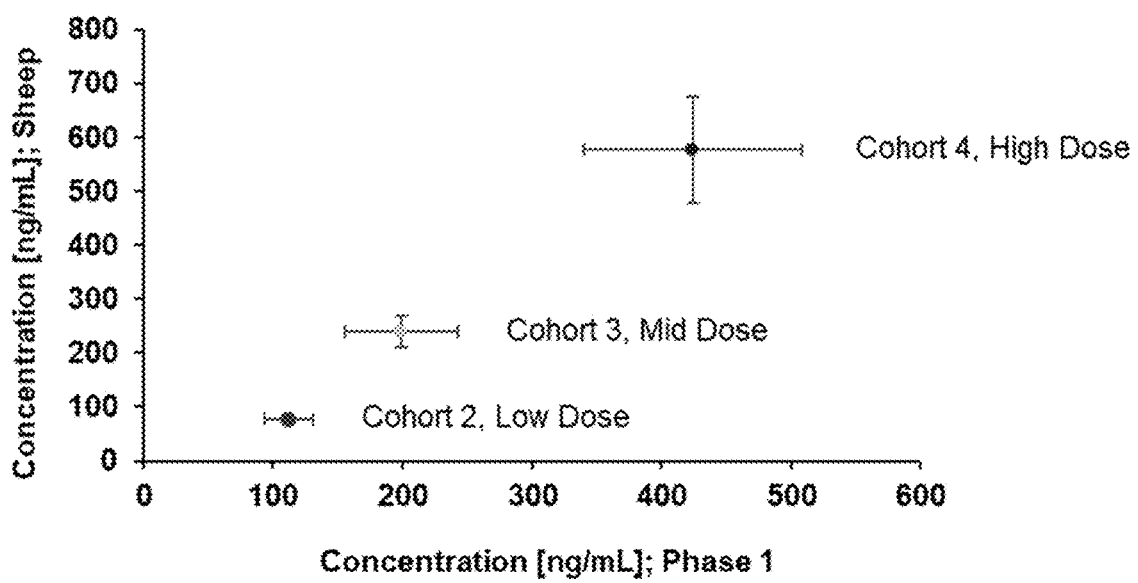

Embodiments of the invention will now be described by way of example and with reference to the accompanying Figures, in which:

FIGS. 1A-B are graphs showing the epithelial lining fluid (ELF) concentration of niclosamide free base following pulmonary administration in sheep compared to systemic exposure of highest human oral dose, relative to IC90 against SARS-CoV-2. FIG. 1A Mean ELF concentration of niclosamide over time following pulmonary administration (±SEM); FIG. 1B Comparison of mean Cmax levels of niclosamide ("UN1911") in ELF to systemic Cmax following a 2 g/day oral dose in humans (Data of Andrews et al. 1983, Pharmacology & therapeutics, 19(2), 245-295 (healthy volunteers) and Burock et al. 2018, BMC Cancer, 18(1): 297 (colorectal cancer patients) combined in "2000 mg single/qd" column);

FIGS. 2A-B are plots showing the pharmacokinetic profile of niclosamide ethanolamine per cohort in the phase 1 clinical trial described in Example 13; and FIG. 3 is a comparison of systemic exposure (Cmax; mean±SEM) of niclosamide administered orally versus inhalation in humans. No mean for "2000 mg, single" column generated as only range of Cmax reported in literature. Data for 500-1000 mg obtained from Schweizer et al., 2018, PLoS ONE.;13(6): e0198389. Data for 2000 mg obtained from Andrews et al. 1983 and Burock et al. 2018 (as above);

FIG. 4 shows a correlation plot of systemic exposure (Cmax–, mean±) of human versus sheep study.

DETAILED DESCRIPTION

Definitions

Unless otherwise stated, the following terms used in the specification and claims have the following meanings set out below.

Reference to "formulation of the invention", "formulations of the invention" "solution of the invention" refer to any of the formulations described herein comprising a halogenated salicylanilide, or a pharmaceutically acceptable salt thereof, and a cyclodextrin. A "solution of the invention" refers to a formulation of the invention wherein the halogenated salicylanilide or pharmaceutically acceptable salt thereof is dissolved in the formulation.

The terms "treating" or "treatment" refers to any indicia of success in the treatment or amelioration of a disease, pathology or condition, including any objective or subjective parameter such as abatement; remission; diminishing of symptoms or making the pathology or condition more tolerable to the subject; slowing in the rate of degeneration or decline; making the final point of degeneration less debilitating; improving the physical or mental well-being of the subject. For example, in relation to the treatment of the infectious, inflammatory and ocular diseases disclosed herein the treatment may include one or more of the following: Reduce or eliminate the virus; prevent or reduce viral replication; reduce or eliminate transmission of the infection; reduce or eliminate fever; reduce or eliminate flu-like symptoms, reduce or eliminate coughing, reduce or eliminate muscle and/or joint pain; improve respiratory status of the subject (e.g. increasing blood oxygen saturation; reducing or eliminating the requirement for oxygen therapy); an improvement in the NEWS2 score; the prevention or treatment of acute respiratory distress syndrome, e.g. associated with the viral infection; the treatment or prevention of pneumonia associated with the viral infection; the treatment or prevention of viral pneumonia; the treatment or prevention of bacterial pneumonia associated with a viral infection or an inflammatory pulmonary disease; reducing or eliminating pulmonary edema; reducing or eliminating pulmonary or ocular inflammation; preventing or reducing lung fibrosis (e.g. preventing or reducing interstitial fibroblasts); reducing one or more inflammatory biomarkers associated with the infection (e.g. reducing one or more of CRP, leukocytes, IL1B, IL-6, IL-10, IL-2, IFNγ, IP10, MCP1, GCSF, IP10, MCP1, MIP1A, and/or TNFα, particularly reducing serum CRP); preventing or reducing proteinaceous exudates associated with infection; preventing or reducing fibrin exudates associated with infection; preventing or ameliorating pulmonary bacterial or fungal infections associated with the viral infection; reduce or eliminate the bacteria or fungus; reduce or eliminate bacterial or fungal replication; reduce or eliminate biofilm formation; reducing or eliminating redness, soreness, itching or swelling of the eye(s); improving or restoring vision, or preventing loss or further loss of vision, reducing constriction and/or spasm of the bronchi, reducing or inhibiting mucus secretion. The terms "treating" or "treatment" also refers to prophylactic treatments, wherein a subject is treated with an formulation of the invention (e.g. an inhaled or intranasal formulation of the invention) to prevent or reduce the risk of a subject contracting a disease (e.g. viral infection) or to prevent a disease or condition from becoming symptomatic. The formulations and methods disclosed herein may also be used in the treatment of asymptomatic subjects. Both, inhalable, intranasal and ocular formulations of the invention are contemplated for use in therapeutic and prophylactic treatments.

The term "associated" or "associated with" in the context of a substance or substance activity or function associated with a disease (e.g. a viral infection such as SARS-CoV-2) means that the disease is caused by (in whole or in part), or a symptom of the disease is caused by (in whole or in part) the substance or substance activity or function.

When a compound or salt (e.g. niclosamide or a pharmaceutically acceptable salt thereof) described in this specification is administered to treat a disorder, a "therapeutically effective amount" is an amount sufficient to reduce or completely alleviate symptoms or other detrimental effects of the disorder; cure the disorder; reverse, completely stop, or slow the progress of the disorder; or reduce the risk of the disorder getting worse.

The term "pharmaceutically acceptable salt" refers to salts that retain the biological effectiveness and properties of the compounds described herein and, which are not biologically or otherwise undesirable. Pharmaceutically acceptable salts of niclosamide are well known to skilled persons in the art. Particular niclosamide salts include ethanolamine or piperazine salts. Accordingly, it may be that a reference to a salt of niclosamide herein may refer to a pharmaceutically acceptable salt of niclosamide, in particular an ethanolamine salt of niclosamide (also referred to herein as niclosamide ethanolamine) (e.g. the 1:1 salt of niclosamide with 2-aminoethanol).

References to "topical treatment" or "topical administration" refer to the application of the formulation to the skin, soft tissues or mucous membranes, including administration by inhalation.

Reference to "a halogenated salicylanilide, or a pharmaceutically acceptable salt thereof" includes hydrates and solvates of a halogenated salicylanilide (e.g. hydrates of niclosamide), and hydrates and solvates of a salt of a halogenated salicylanilide (e.g. hydrates of a salt of niclosamide). Non-solvated and non-hydrated forms of the halogenated salicylanilide, or salt thereof, are also contemplated.

Reference to the formulation being in the form of a "solution" means that the components of the formulation are sufficiently dissolved such that the formulation is clear to the naked eye (i.e. the formulation is free from visible particles).

Reference to an "aerosol" means the suspension of solid particles or liquid droplets comprising a halogenated salicylanilide (e.g. niclosamide) or a pharmaceutically acceptable salt thereof in a gas (e.g. air or a suitable propellant gas). An aerosol comprising liquid droplets comprising liquid droplets is suitably formed by aerosolizing a solution or suspension comprising the halogenated salicylanilide (e.g. niclosamide) or a pharmaceutically acceptable salt thereof, for example any of the solutions or suspensions described herein. The continuous gas phase of the aerosol may be selected from any gas or mixture of gases which is pharmaceutically acceptable. Preferably the gas may simply be air or compressed air. Alternatively, other gases and gas mixtures, such as air enriched with oxygen, carbon dioxide, or mixtures of nitrogen and oxygen may be used. Aerosolization may be achieved using a suitable inhalation device, for example a nebulizer described herein.

The particle/droplet size of an aerosol may be measured as the mass median diameter (MMD) of the aerosol droplet/particles. The MMD may be measured using well-known methods, for example a laser diffraction technique using a Malvern MasterSizer X™. Suitably, the MMD may be determined by nebulizing a suitable volume of the solution or suspension (e.g.) 2 mL using a suitable nebulizer device. The resulting aerosol is analysed by directing by directing the aerosol cloud through the laser beam of the MasterSizer X™ instrument using an aspiration flow of 20 L/min at a temperature of 23° C. (±2° C.) and a relative humidity of 50% (±5%).

The Geometric Standard Deviation (GSD) is a measure of the measure the particle or droplet size distribution in an aerosol. The GSD may be determined using known methods, for example using well-known laser diffraction methods, for example using a MasterSizer X™ under the same conditions described above for the measurement of MMD.

Reference to a "subject" herein means a human or animal subject. Preferably the subject is warm-blooded mammal. More preferably the subject is a human.

Unless stated otherwise, reference herein to a "% by weight of halogenated salicylanilide (e.g. niclosamide), or a pharmaceutically acceptable salt thereof" is intended to refer to the amount of the free acid (i.e. non-salt form) of the halogenated salicylanilide. For example, reference to a composition comprising "5% by weight of halogenated salicylanilide (e.g. niclosamide) or a pharmaceutically acceptable salt thereof" refers to a composition comprising 5% by weight of the halogenated salicylanilide as the free acid. Accordingly, where such a composition comprises a pharmaceutically acceptable salt of a halogenated salicylanilide, the absolute amount of the salt in the composition will be higher than 5% by weight in view of the salt counter ion that will be also be present in the composition.

Reference to a "non-aqueous" composition, means that the composition is anhydrous and therefore substantially water free. For example, the compositions disclosed herein (e.g. solutions or suspensions comprising halogenated salicylanilide (e.g. niclosamide) or a pharmaceutically acceptable salt thereof) contain less than 5%, less than 1% or suitably less than 0.01%, preferably less than 0.001% by weight water. Preferred non-aqueous compositions are those which are anhydrous and contain no detectable water.

As will be recognised by the skilled person, reference to administering by inhalation a solution or suspension comprising a halogenated salicylanilide (e.g. niclosamide), or a pharmaceutically acceptable salt thereof, and a cyclodextrin requires the solution or suspension to be delivered to the subject in a form that is suitable for inhalation. Typically the solution or suspension will be delivered in the form of a spray or, preferably in the form of an aerosol formed from the solution or suspension. Methods and devices for delivering a liquid or suspension in an inhalable form are well known and include nebulizers and pMDI inhalers.

Where reference is made herein to a formulation of the invention for use in the treatment or prevention of a condition (e.g. a viral infection) is to be understood as also encompassing a method for the treatment or prevention of that condition in a subject by administering an effective amount of the formulation to the subject; and use of the formulation for the manufacture of a medicament for the treatment or prevention of the condition.

Reference to "about" in the context of a numerical is intended to encompass the value+/−10%. For example, about 20% includes the range of from 18% to 22%.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The readers attention is directed to all papers and documents which are filed concurrently with or previous to this specification in connection with this application and which are open to public inspection with this specification, and the contents of all such papers and documents are incorporated herein by reference.

Halogenated Salicylanilides

Halogenated salicylanilides are also known as 2-hydroxy-N-phenylbenzamides or 2-hydroxybenzanilides. Salicylanilides are weakly acidic phenolic compounds. Halogenated salicylanilides are salicylanilides substituted by at least one halo group. A number of halogenated salicylanilide derivatives are known. For example, the halogenated salicylanilide may be any of the niclosamide analogues described in WO 2008/021088, which are incorporated herein by reference thereto.

The halogenated salicylanilide may be a halogenated salicylanilide of the formula (I):

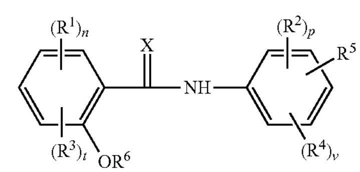

(I)

wherein

X is O or S;

$R^1$ and $R^2$ are at each occurrence independently selected from halo;

$R^3$ and $R^4$ are at each occurrence independently selected from H, $C_{1-6}$ alkyl, $C_{1-6}$ haloalkyl, $—OR^{A1}$, $—NO_2$ and —CN;

$R^5$ is H or $-L^1-R^7$;

$R^6$ is H or $—C(O)R^{A2}$;

$L^1$ is selected from a bond, O, S, or $—(CR^{A3}R^B)_o—$, wherein o is 1 or 2;

$R^7$ is phenyl, unsubstituted or substituted with 1, 2, or 3 groups selected from halo, $C_{1-4}$ alkyl, $C_{1-4}$ haloalkyl, $—OR^{A4}$, $—NO_2$ and —CN;

$R^{A1}$, $R^{A2}$, $R^{A3}$ and $R^{A4}$ are at each occurrence independently selected from H and $C_{1-4}$ alkyl;

$R^B$ is at each occurrence selected from H, $C_{1-4}$ alkyl and —CN;

n and p are each independently selected from 0, 1, 2, 3 or 4, with the proviso that n+p is at least 1;
t and v are independently selected from 0, 1 and 2;
or a pharmaceutically acceptable salt, or ester or hydrate thereof.

The following statements in the numbered paragraphs below apply to compounds of the formula (I). These statements are independent and interchangeable. In other words, any of the features described in any one of the following statements may (where chemically allowable) be combined with the features described in one or more other statements below. In particular, where a compound is exemplified or illustrated in this specification, any two or more of the statements below which describe a feature of that compound, expressed at any level of generality, may be combined so as to represent subject matter which is contemplated as forming part of the disclosure of this invention in this specification.

1. X is O.
2. $R^1$ and $R^2$ are at each occurrence independently selected from fluoro, chloro, bromo and iodo.
3. $R^1$ and $R^2$ are at each occurrence independently selected from chloro, bromo and iodo.
4. $R^1$ is chloro.
5. $R^1$ is bromo.
6. $R^1$ is iodo.
7. $R^2$ is chloro.
8. $R^2$ is bromo.
9. $R^2$ is iodo.
10. $R^3$ and $R^4$ are at each occurrence independently selected from H, $C_{1-4}$-alkyl, $C_{1-4}$-haloalkyl, —$OR^{41}$, —$NO_2$ and —CN.
11. $R^3$ and $R^4$ are at each occurrence independently selected from H, $C_{1-4}$-alkyl, —$OR^{41}$ and —$NO_2$.
12. $R^3$ and $R^4$ are at each occurrence independently selected from H, $C_{1-4}$-alkyl, —$CF_3$, —OH, —OMe, —$NO_2$ and —CN, for example H, $C_{1-4}$-alkyl, —OH or —$NO_2$.
13. $R^4$ is at each occurrence independently selected from —$CF_3$, —$NO_2$ and —CN.
14. $R^4$ is at each occurrence independently selected from $C_{1-4}$-haloalkyl, —$NO_2$ and —CN.
15. $R^5$ is H.
16. $R^5$ is $L^1$-$R^7$.
17. $L^1$ is selected from —O—, —$CH_2$— and —CH(CN)—, for example —O— or —CH(CN)—.
18. $R^7$ is phenyl, unsubstituted or substituted with 1, 2, or 3 groups selected from halo, $C_{1-4}$-alkyl, $C_{1-4}$-haloalkyl and —CN.
19. $R^7$ is phenyl unsubstituted or substituted with 1, 2, or 3 groups (for example 1 or 2 groups) selected from halo.
20. $R^7$ is unsubstituted phenyl.
21. $L^1$ is selected from —O— and —CH(CN)—; and $R^7$ is phenyl unsubstituted or substituted with 1, 2, or 3 groups selected from halo.
22. $R^6$ is H.
23. $R^6$ is —$C(O)R^{42}$, for example —$C(O)CH_3$.
24. t=0 or 1.
25. t=0.
26. v=0 or 1.
27. v=0.
28. o is 1.
29. v=1 and $R^4$ is selected from —OH, $C_{1-4}$ alkyl and —$NO_2$.
30. v=1 and $R^4$ is selected from —CN, $C_{1-4}$ haloalkyl (e.g. —$CF_3$) and —$NO_2$.
31. A compound of formula (I), or a pharmaceutically acceptable salt thereof.

Particular compounds are compounds of formula (I), or a pharmaceutically acceptable salt, hydrate or ester thereof wherein:
X is O;
$R^1$ and $R^2$ are at each occurrence independently selected from halo;
$R^3$ and $R^4$ are at each occurrence independently selected from H, $C_{1-4}$ alkyl, —$OR^{41}$, —$NO_2$ and CN;
$R^5$ is H or -$L^1$-$R^7$;
$R^6$ is H or —$C(O)R^{42}$;
$L^1$ is selected from 0 and —CH(CN)—;
$R^7$ is phenyl unsubstituted or substituted with 1, 2, or 3 groups selected from halo;
$R^{41}$ and $R^{42}$ are at each occurrence independently selected from H and $C_{1-4}$-alkyl;
n and p are each independently selected from 0, 1, 2, 3 or 4, with the proviso that n+p is at least 1;
t and v are independently selected from 0, 1 and 2;
or a pharmaceutically acceptable salt, or ester thereof.

It may be that the halogenated salicylanilide is selected from:

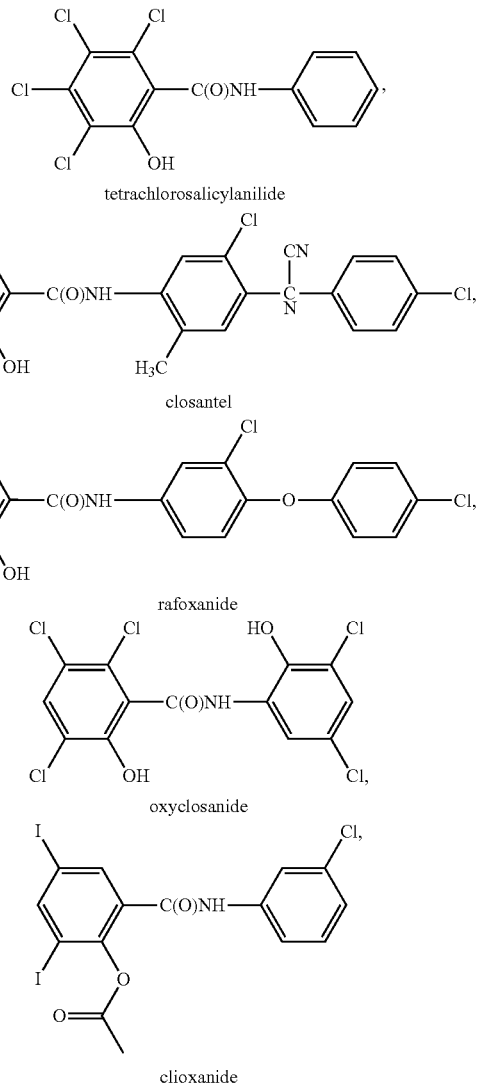

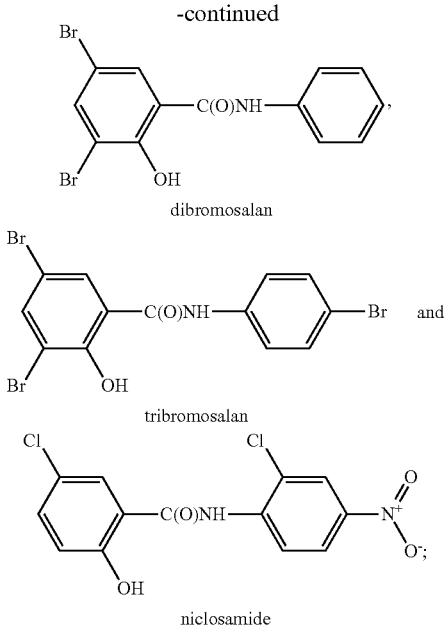

dibromosalan tribromosalan niclosamide or a pharmaceutically acceptable salt or solvate (e.g. hydrate) thereof.

The halogenated salicylanilide may be a thioamide derivative, for example brotianide:

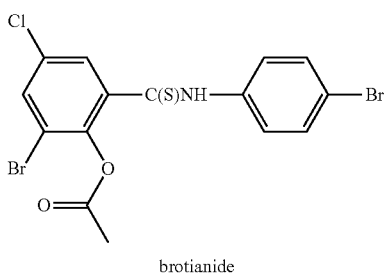

brotianide or a pharmaceutically acceptable salt, solvate (e.g. hydrate) thereof.

The halogenated salicylanilide may be selected from the group consisting of tetrachlorosalicylanilide, closantel, rafoxanide, oxyclozanide, resorantel, clioxanide, dibromosalan, tribromosalan, brotianide and niclosamide, or a pharmaceutically acceptable salt or prodrug or derivative thereof.

The halogenated salicylanilide may be selected from the group consisting of tetrachlorosalicylanilide, closantel, rafoxanide, oxyclozanide, resorantel, dibromosalan, tribromosalan and niclosamide, or a pharmaceutically acceptable salt or ester thereof.

The halogenated salicylanilide may be selected from the group consisting of clioxanide, closantel, oxyclozanide, rafoxanide, tribromosalan or a pharmaceutically acceptable salt or ester thereof.

The halogenated salicylanilide may be selected from the group consisting of tetrachlorosalicylanilide, closantel, rafoxanide, oxyclozanide, resorantel, clioxanide, dibromosalan, tribromosalan, brotianide and niclosamide, or a pharmaceutically acceptable salt or hydrate thereof.

The halogenated salicylanilide may be selected from the group consisting of tetrachlorosalicylanilide, closantel, rafoxanide, oxyclozanide, resorantel, clioxanide, dibromosalan, tribromosalan and niclosamide, or a pharmaceutically acceptable salt or hydrate thereof.

The halogenated salicylanilide may be selected from the group consisting of niclosamide, clioxanide, closantel, oxyclozanide, rafoxanide and tribromosalan, or a pharmaceutically acceptable salt or hydrate thereof.

The halogenated salicylanilide may be selected from the group consisting of clioxanide, closantel, oxyclozanide, rafoxanide and tribromosalan, or a pharmaceutically acceptable salt or hydrate thereof.

The halogenated salicylanilide may be selected from the group consisting of clioxanide, closantel, rafoxanide and tribromosalan, or a pharmaceutically acceptable salt or hydrate thereof.

The halogenated salicylanilide may be selected from the group consisting of tetrachlorosalicylanilide, closantel, rafoxanide, oxyclozanide, resorantel, clioxanide, dibromosalan, tribromosalan, brotianide and niclosamide.

The halogenated salicylanilide may be selected from the group consisting of niclosamide, closantel, oxyclozanide and rafoxanide, or a pharmaceutically acceptable salt thereof.

The halogenated salicylanilide may be selected from the group consisting of niclosamide and oxyclozanide, or a pharmaceutically acceptable salt or hydrate thereof.

The halogenated salicylanilide may be clioxanide, or a pharmaceutically acceptable salt or ester thereof, for example the halogenated salicylanilide is clioxanide or a pharmaceutically acceptable salt or hydrate thereof, suitably the halogenated salicylanilide is clioxanide.

The halogenated salicylanilide may be closantel, or a pharmaceutically acceptable salt or hydrate thereof, for example the halogenated salicylanilide is closantel or a pharmaceutically acceptable salt thereof, suitably the halogenated salicylanilide is closantel.

The halogenated salicylanilide may be oxyclozanide, or a pharmaceutically acceptable salt or ester thereof, for example the halogenated salicylanilide is oxyclozanide or a pharmaceutically acceptable salt or hydrate thereof, suitably the halogenated salicylanilide is oxyclozanide.

The halogenated salicylanilide may be rafoxanide, or a pharmaceutically acceptable salt or hydrate thereof, for example the halogenated salicylanilide is rafoxanide or a pharmaceutically acceptable salt thereof, suitably the halogenated salicylanilide is rafoxanide.

The halogenated salicylanilide may be tribromosalan, or a pharmaceutically acceptable salt or hydrate thereof, for example the halogenated salicylanilide is tribromosalan or a pharmaceutically acceptable salt thereof, suitably particularly the halogenated salicylanilide is tribromosalan.

The halogenated salicylanilide may be niclosamide, or a pharmaceutically acceptable salt or hydrate thereof, for example the halogenated salicylanilide is niclosamide or a pharmaceutically acceptable salt thereof.

In certain embodiments the halogenated salicylanilide is niclosamide in the free acid form.

In certain embodiments the halogenated salicylanilide is a pharmaceutically acceptable salt of niclosamide, for example an ethanolamine salt, or piperazine salt.

In preferred embodiments, the halogenated salicylanilide is niclosamide ethanolamine.

Cyclodextrins

Cyclodextrins are a family of cyclic oligosaccharides, consisting of a macrocyclic ring of five or more glucose subunits joined by α-1,4 glycosidic bonds. Common cyclodextrins having six to eight glucose units include: α-cyclodextrin (six glucose units), β-cyclodextrin (seven glucose units) and γ-cyclodextrin (eight glucose units). Derivatives of cyclodextrins may be prepared by chemical modification of some or all of the hydroxyl groups, for example by the addition of alkyl (e.g. methyl, hydroxypropyl or hydroxyethyl) or acetyl groups. Cyclodextrin may be chemically modified in order to improve its solubility.

In some embodiments, the cyclodextrin is water soluble. A water-soluble cyclodextrin derivative preferably used in the present invention refers to a derivative having water solubility of at least that of β-cyclodextrin. Examples of such water-soluble cyclodextrin derivatives are sulfobutylcyclodextrin, hydroxypropylcyclodextrin, maltosylcyclodextrin, and salts thereof. In particular, sulfobutyl-β-cyclodextrin, hydroxypropyl-β-cyclodextrin, maltosyl-β-cyclodextrin, and salts thereof.

Other preferred cyclodextrin derivatives according to the invention are methylcyclodextrins (products of the cyclodextrins methylation), dimethylcyclodextrins (DIMEB) (preferably substituted in 2 and in 6), trimethylcyclodextrins (preferably substituted in 2, 3 and 6), "random methylated" cyclodextrins (RAMEB) (preferably substituted at random in 2, 3 and 6, but with a number of 1,7 to 1,9 methyl by unit glucopyrannose), hydroxypropylcyclodextrins (HPCD, hydroxypropylated cyclodextrins preferably substituted randomly mainly in position 2 and 3 (e.g. HP-β-CD, HP-γ-CD)), sulfobutylethercyclodextrins (SBECD), hydroxyethyl-cyclodextrins, carboxymethylethylcyclodextrins, ethylcyclodextrins, cyclodextrins amphiphiles obtained by grafting hydrocarbonated chains in the hydroxyl groups and being able to form nanoparticles, cholesterol cyclodextrins and triglycerides-cyclodextrins obtained by grafting cyclodextrins monoaminated (with a spacer arm).

The cyclodextrin may be or a derivative thereof, such as methylated, acetylated or hydroxypropylated α-cyclodextrin. The cyclodextrin may be β-cyclodextrin or a derivative thereof, such as methylated, acetylated and/or hydroxypropylated β-cyclodextrin. The cyclodextrin may be or γ-cyclodextrin or a derivative thereof, such as such as methylated, acetylated and/or hydroxypropylated γ-cyclodextrin. In some embodiments, the cyclodextrin is selected from the group consisting of: beta-cyclodextrin and its synthetic derivatives such as HP-β-CD, SBE-β-CD, RM-β-CD, DIME-β-CD, TRIME-β-CD, hydroxybutyl-β-CD, glucosyl-β-CD, and maltosyl-β-CD. In some embodiments, the cyclodextrin is selected from the group consisting of: γ-cyclodextrin and its synthetic derivatives such as HP-γ-CD, SBE-γ-CD, RM-γ-CD, DIME-γ-CD, TRIME-γ-CD, hydroxybutyl-γ-CD, glucosyl-γ-CD, and maltosyl-γ-CD.

Preferably the cyclodextrin is HP-β-CD.

Inhalable Formulations Comprising a Halogenated Salicylanilide and a Cyclodextrin The halogenated salicylanilide (e.g. niclosamide) or pharmaceutically acceptable salt thereof and the cyclodextrin may be present in any pharmaceutical formulation. In particular the formulation may be suitable for administration by inhalation. Preferred inhalable formulations comprising a halogenated salicylanilide (e.g. niclosamide) or a pharmaceutically acceptable salt thereof include for example, compositions in the form of a solution, suspension, powder, an aerosol of a solution or an aerosol of a suspension as described in more detail herein.

Also contemplated are other inhalable formulations comprising a halogenated salicylanilide (e.g. niclosamide) or a pharmaceutically acceptable salt thereof and a cyclodextrin, for example: solid lipid particles comprising niclosamide or a pharmaceutically acceptable salt thereof and a cyclodextrin dissolved or dispersed therein; emulsions comprising niclosamide, or a pharmaceutically acceptable salt thereof, and a cyclodextrin (e.g. an oil-in water emulsion wherein the niclosamide, or a pharmaceutically acceptable salt thereof and the cyclodextrin, is dissolved or dispersed in the aqueous phase of the emulsion); or liposomes comprising niclosamide, or a pharmaceutically acceptable salt thereof, and a cyclodextrin.

Many patients have increased sensitivity to various chemical tastes, including bitter, salt, sweet, metallic sensations. To create well-tolerated drug products, by non-limiting example taste masking may be accomplished through the addition of taste-masking excipients, adjusted osmolality, and/or sweeteners to the formulation. By non-limiting example, formulations may further include flavouring agents, taste-masking agents, inorganic salts (e.g., sodium chloride), antimicrobial agents (e.g., benzalkonium chloride), sweeteners, antioxidants, antistatic agents, surfactants (e.g., polysorbates such as "TWEEN 20" and "TWEEN 80"), sorbitan esters, saccharin, lipids (e.g., phospholipids such as lecithin and other phosphatidylcholines, phosphatidylethanolamines), fatty acids and fatty esters, steroids (e.g., cholesterol), and chelating agents (e.g., EDTA, zinc and other such suitable cations). Other pharmaceutical excipients and/or additives suitable for use in the compositions according to the invention are listed in "Remington: The Science & Practice of Pharmacy", 19.sup.th ed., Williams & Williams, (1995), and in the "Physician's Desk Reference", 52.sup.nd ed., Medical Economics, Montvale, N.J. (1998).

Solutions and Suspensions Comprising a Halogenated Salicylanilide and a Cyclodextrin In certain embodiments the formulation comprising a halogenated salicylanilide (e.g. niclosamide), or a pharmaceutically acceptable salt thereof, and a cyclodextrin is a solution or suspension. Preferably the solution or suspension is a liquid, more preferably a liquid that is suitable for aerosolization using for example a nebulizer inhaler. Thus a reference herein to any of the solutions or suspensions comprising a halogenated salicylanilide (e.g. niclosamide), or a pharmaceutically acceptable salt thereof, and a cyclodextrin are preferably liquid solutions or liquid suspensions comprising the halogenated salicylanilide (e.g. niclosamide), or a pharmaceutically acceptable salt thereof, and a cyclodextrin.

In certain embodiments the halogenated salicylanilide (e.g. niclosamide), or a pharmaceutically acceptable salt thereof, and the cyclodextrin are dissolved or dispersed in a liquid medium to provide a solution or suspension suitable for inhalation. In certain embodiments the halogenated salicylanilide (e.g. niclosamide), or a pharmaceutically acceptable salt thereof, and a cyclodextrin are dissolved or dispersed in a solvent comprising or consisting of water, thereby forming an aqueous solution or suspension. In some embodiments, the halogenated salicylanilide (e.g. niclosamide), or a pharmaceutically acceptable salt thereof, and a cyclodextrin are dissolved or dispersed in a solvent comprising water and a co-solvent, such as DMSO.

It has been found that some formulations according to the invention are able to form a substantially clear solution, i.e. with no visible precipitate. Thus, in some embodiments a solution according to the invention is substantially clear. In some embodiments, the solution is physically stable (i.e. no visible precipitate forms) when stored (e.g. in a closed container) for at least 1 day, at least 2 days, at least 4 days, at least 7 days, at least 14 days, at least 21 days or at least 28 days. The solution may be physically stable when stored (e.g. in a closed container) at 5° C., 10° C., 15° C., 20° C., 25° C., 30° C., 35° C. or 40° C. In some embodiments, the solution is physically stable after storage (e.g. in a closed container) at 25° C. for at least 7, 14 or 28 days. In some embodiments, the solution is physically stable after storage (e.g. in a closed container) at 40° C. for at least 7, 14 or 28 days.

In embodiments where the halogenated salicylanilide (e.g. niclosamide), or a pharmaceutically acceptable salt thereof, and the cyclodextrin are present as a suspension in a liquid medium.

The halogenated salicylanilide (e.g. niclosamide), or a pharmaceutically acceptable salt thereof, may be present in the solution or suspension in the liquid medium in any of the amounts described herein. When the halogenated salicylanilide (e.g. niclosamide), or pharmaceutically acceptable salt thereof is present as a solution, the solution typically contains from about 0.1 to about 5% by weight (e.g. about 1%) of the halogenated salicylanilide (e.g. niclosamide) or pharmaceutically acceptable salt thereof.

The cyclodextrin may be present in the solution or suspension in the liquid medium in any of the amounts described herein. When the cyclodextrin is present as a solution, the solution typically contains from about 1 to about 60%, by weight, for example about 1 to about 25% by weight (e.g. about 15%) of the cyclodextrin.

Some halogenated salicylanilides such as niclosamide are known to be poorly soluble in water. Without being bound by theory, it is thought that at least a portion of the halogenated salicylanilide will form a complex with the cyclodextrin in the formulation of the invention, thereby improving its solubility. In particular, complexation with cyclodextrin is believed to be beneficial for the treatment of pulmonary disease, since the complex may help to prevent precipitation of the halogenated salicylanilide when the formulation contacts the lung tissue. It will be appreciated that in solution or suspension the halogenated salicylanilide and cyclodextrin may continuously fluctuate between a bound (i.e. complexed) and non-bounded (i.e. non-complexed) state. Thus, from about 20 to about 100% by weight of the halogenated salicylanilide may form a complex with the cyclodextrin, based on the weight of the halogenated salicylanilide. In liquid formulations, any non-complexed components (halogenated salicylanilide and/or cyclodextrin) may be present in solution and/or suspension.

Liquid formulations according to the invention may have an osmolality from about 100 mOsmol/kg to about 1000 mOsmol/kg. In some embodiments, the osmolality is from about 150 mOsmol/kg to about 750 mOsmol/kg, from about 200 mOsmol/kg and about 500 mOsmol/kg, preferably from about 230 to about 350 mOsmol/kg, more preferably from about 280 to about 330 mOsmol/kg (e.g. from about 290 to about 320 mOsmol/kg).

In some embodiments, a liquid formulation comprises from about 1% to about 25% by weight of cyclodextrin and from about 0.1% to about 5% by weight of niclosamide or a pharmaceutically acceptable salt thereof (e.g. niclosamide ethanolamine), based on the weight of the liquid formulation.

In some embodiments, a liquid formulation comprises:
0.1-5% of a halogenated salicylanilide or a pharmaceutically acceptable salt thereof, for example 0.5-2% or 1-1.5% of niclosamide ethanolamine;
1-25% of cyclodextrin, for example 3-15% or 5 to 10% of HP-β-CD;
0.1-10% of polymers, for example 0.5-5% or 1-2% of PVP;
0-0.2% of stabilizing agent, for example 0.05 to 0.1% of disodium edetate;
0-0.02% of preservative, for example 0.005-0.01% benzalkonium chloride.
0-0.9% of electrolyte, for example 0.1-0.5% of sodium chloride;
0-10% of a co-solvent, for example 0.5-5% or 1% of DMSO;
the balance being water,
wherein the percentages are by weight based on the weight of the liquid formulation.

Suitably the liquid formulation has a pH of from 7.0 to 8.5, for example from 7.5 to 7.8, or from 7.6 to 8.0, preferably about 7.8.

In some embodiments, a liquid formulation comprises:
0.1-5% of a halogenated salicylanilide or a pharmaceutically acceptable salt thereof, for example 0.5-2% or 1-1.5% of niclosamide ethanolamine;
1-25% of cyclodextrin, for example 3-15% or 5 to 10% of HP-β-CD;
0.1-10% of polymers, for example 0.5-5% or 1-2% of PVP;
0-3% of one or more pH modifiers (suitably the pH modifiers are present in an amount to provide a pH of from 7.0 to 8.5, for example from 7.5 to 7.8, or from 7.6 to 8.0, preferably about 7.8. For example 0.1-0.5% of NaOH (e.g. added as a solid or a 1 M solution), and 0.5-3.0% of 2N HCl);
the balance being water,
wherein the percentages are by weight based on the weight of the liquid formulation.

In some embodiments, a liquid formulation comprises:
0.5-1.5% niclosamide ethanolamine;
5-20% cyclodextrin, preferably a β-cyclodextrin, more preferably HP-β-CD;
0.5-5% PVP (e.g. PVP 30);
the balance being water,
wherein the percentages are by weight based on the weight of the liquid formulation; and
wherein the formulation has a pH of from 7.0 to 8.5, for example from 7.5 to 7.8, or from 7.6 to 8.0, preferably about 7.8.

In some embodiments, a liquid formulation comprises:
about 1% niclosamide ethanolamine;
about 15% cyclodextrin, preferably a β-cyclodextrin, more preferably HP-β-CD;
about 2% PVP (e.g. PVP 30);
the balance being water,
wherein the percentages are by weight based on the weight of the liquid formulation; and
wherein the formulation has a pH of from 7.0 to 8.5, for example from 7.5 to 7.8, or from 7.6 to 8.0, preferably about 7.8.

In some embodiments, a liquid formulation comprises:
about 1% niclosamide ethanolamine;
about 10% cyclodextrin, preferably a β-cyclodextrin, more preferably HP-β-CD;
about 2% PVP (e.g. PVP 30);
the balance being water,
wherein the percentages are by weight based on the weight of the liquid formulation; and
wherein the formulation has a pH of from 7.0 to 8.5, for example from 7.5 to 7.8, or from 7.6 to 8.0, preferably about 7.8.

Aerosols

A solution or suspension comprising the halogenated salicylanilide (e.g. niclosamide), or a pharmaceutically acceptable salt thereof, and the cyclodextrin may be administered to the subject in a form suitable for inhalation. For example the solution or suspension may be administered as a spray, preferably as an aerosol of the solution or suspension comprising niclosamide or a pharmaceutically acceptable salt thereof.

Aerosols of the solutions and dispersions comprising the halogenated salicylanilide (e.g. niclosamide), or a pharmaceutically acceptable salt thereof, and the cyclodextrin disclosed herein form a further aspect of the invention.

Inhalation of the inhalable composition of the invention (e.g. an aerosol of a solution or dispersion comprising the halogenated salicylanilide (e.g. niclosamide), or a pharmaceutically acceptable salt thereof, and the cyclodextrin) delivers the halogenated salicylanilide (e.g. niclosamide) or pharmaceutically acceptable salt thereof to the airways of the subject. In certain embodiments inhalation of the aerosol delivers the halogenated salicylanilide (e.g. niclosamide) to the upper respiratory tract for example one or more of the nose and nasal passages, paranasal sinuses, the pharynx, the portion of the larynx above the vocal cords. Preferably, inhalation of the aerosol delivers halogenated salicylanilide (e.g. niclosamide) to the lower respiratory tract, for example one or more of the trachea, lungs, bronchi, bronchioles, alveolar duct or alveoli.

In certain embodiments the aerosol of the solution or suspension comprising the halogenated salicylanilide (e.g. niclosamide), or a pharmaceutically acceptable salt thereof, and the cyclodextrin, has a mass median diameter of less than about 5 µm. It may be that the MMD is of less than about 2 µm. It may be that the MMD of the aerosol is from about 0.5 µm to about 5.5 µm. Preferably the MMD of the aerosol is from about 1 µm to about 5 µm. Suitably the aerosol has a geometric standard deviation (GSD) of less than about 2.2, for example less than 2.0, or less than 1.8. Preferably the GSD of the aerosol is less than 1.6.

In some embodiments the aerosol of the solution or suspension comprising the halogenated salicylanilide (e.g. niclosamide), or a pharmaceutically acceptable salt thereof, and the cyclodextrin, has a mass median diameter of less than about 100 µm, less than about 90 µm, less than about 80 µm, less than about 70 µm, less than about 60 µm or less than about 50 µm. In some embodiments the MMD of the aerosol is from about 5 to about 150 µm, from about 10 µm to about 120 µm, from about 20 to about 100 µm, from about 30 µm to about 90 µm, from about 40 µm to about 80 µm, or from about 50 µm to about 70 µm, e.g. about 65 µm.

As is known in the art, droplet or particle size distribution may also be defined by reference to D10 and D90 values. 10% of particles or droplets are smaller than the D10 value. 90% of particles or droplets are smaller than the D90 value. In some embodiments, an aerosol of a formulation of the invention has a D10 of from 1 to 100 µm, from 5 to 80 µm, from 10 to 60 µm, from 15 to 50 µm or from 20 to 40 µm (e.g. about 30 µm). In some embodiments, an aerosol of a formulation of the invention has a D90 of from 50 to 500 µm, from 80 to 400 µm, from 100 to 300 µm or from 150 to 250 µm. The particle size distribution may be measured using well-known methods, for example by laser diffraction such as Low-Angle Laser Light Scattering (LALLS) using a SprayTec apparatus from Malvern.

Aerosols of a solution or suspension comprising a halogenated salicylanilide (e.g. niclosamide), or a pharmaceutically acceptable salt thereof, and a cyclodextrin may be formed using known methods, for example via a suitable inhaler device, particularly nebulizers as described herein.

Powders Comprising Niclosamide

In certain embodiments the inhalable composition is a powder comprising a halogenated salicylanilide (e.g. niclosamide), or a pharmaceutically acceptable salt thereof, and a cyclodextrin.

Suitably the powder comprises particles that are of a respirable size. In certain embodiments the powder has an particle size (MMD) of less than 10 µm, for example less than 5 µm. For example, the MMD of the powder particles is from about 1 µm to about 5 µm. Suitably the particles administered to the subject (e.g. as an aerosol of the powder) have a GSD of less than about 2.2, for example less than 2.0, or less than 1.8.

Powders suitable for inhalation may be prepared using well-known methods, for example by micro-precipitation, lyophilisation or spray drying, or spray-freeze drying a solution of the invention comprising a halogenated salicylanilide (e.g. niclosamide), or a pharmaceutically acceptable salt thereof, and a cyclodextrin.

In certain embodiments respirable particles comprising the halogenated salicylanilide (e.g. niclosamide), or a pharmaceutically acceptable salt thereof, and the cyclodextrin may be prepared by precipitation, lyophilisation or spray drying, or spray-freeze drying a solution comprising the halogenated salicylanilide, the cyclodextrin and a suitable carrier to provide respirable powder particles comprising the halogenated salicylanilide, the cyclodextrin and the carrier as composite particles. Suitable carriers include inert carriers such as starch, sugars (e.g. mannitol, lactose or trehalose).

In certain embodiments powders comprising respirable particles of a halogenated salicylanilide (e.g. niclosamide), or a pharmaceutically acceptable salt thereof, and a cyclodextrin may be formulated with carrier particles. It may be that the carrier particles are larger than the particles of the halogenated salicylanilide and cyclodextrin, and the mixing of the carrier with the respirable halogenated salicylanilide/cyclodextrin powder forms an "ordered mixture". Such ordered mixtures can be useful in dry powder inhalers. The fine particles of halogenated salicylanilide/cyclodextrin powder may loosely associate with the larger carrier particles (e.g. approximately 100 µm) to facilitate the filling and storage of the powder in an inhaler reservoir of unit dosage (e.g. vial, capsule or blister pack). Upon administration from the inhaler the turbulence and/or mechanical impaction experienced by the powder releases the fine particles of drug from the larger carrier particles to provide a respirable fine particle fraction of drug which is inhaled into the respiratory tract of the subject. Carriers suitable for the preparation of ordered mixtures include, for example lactose, mannitol and microcrystalline cellulose.

Powders comprising a halogenated salicylanilide (e.g. niclosamide), or a pharmaceutically acceptable salt thereof, and a cyclodextrin may be administered to the subject using a suitable dry powder inhaler. Alternatively, a powder comprising a halogenated salicylanilide (e.g. niclosamide), or a pharmaceutically acceptable salt thereof, and a cyclodextrin, as described herein, may be dissolved or suspended in a suitable solvent (preferably water) prior to administration, e.g. via nebulization or application of droplets.

Other Components in Inhalable Pharmaceutical Compositions

The formulation described herein optionally further comprise one or more viscosity modifying agents, emulsifiers, surfactants, humectants, oils, waxes, polymer, preservatives, pH modifying agents (for example a suitable acid or base, for example an organic acid or organic amine base), buffers, stabilizers, electrolytes antioxidants (for example butylated hydroxyanisol or butylated hydroxytoluene), crystallisation inhibitors (for example a cellulose derivative such as hydroxypropylmethyl cellulose or polyvinylpyrrolidone), colorants, fragrances and taste-masking agents. Such excipients s are well-known, for example as listed in the Handbook of Pharmaceutical Excipients, 7$^{th}$ Edition, Rowe et al.

Systems and Devices

Inhalers

The formulation may be administered to the subject by inhalation. In some embodiments the formulation is suitably delivered to the subject in an inhalable form using a suitable inhaler. Inhalers are well-known and include dry powder inhalers (DPI), metered dose inhalers (MDI), pressurised metered dose inhalers (pMDI) and nebulizers.

Nebulizers

Nebulizers are suitable for forming an aerosol of the formulation. Nebulizers are particularly suitable for forming an aerosol of solution or suspension comprising a halogenated salicylanilide (e.g. niclosamide) or a pharmaceutically acceptable salt thereof, and a cyclodextrin, for example the liquid solutions and suspensions comprising niclosamide or a pharmaceutically acceptable salt thereof and a cyclodextrin as described herein. Suitable nebulizers generate a respirable aerosol of the inhalable pharmaceutical composition.

The nebulizer may comprise a reservoir containing the formulation (e.g. solution or suspension), wherein actuation of the nebulizer delivers a single dose of the formulation which is inhaled as an aerosol by the subject. Alternatively, the nebulizer may be a multiple-dose nebulizer wherein a unit dose of the formulation is loaded into the nebulizer (e.g. via a vial, syringe, capsule, blister-pack or other suitable container) and is administered to the subject as a unit dose of aerosol of the formulation.

In certain embodiments the nebulizer is selected from a jet nebulizer, a vibrating mesh nebulizer, an ultrasonic nebulizer. A jet nebulizer utilizes air pressure breakage of a solution or suspension into aerosol droplets. Ultrasonic nebulizers generate an aerosol using shearing of a solution or suspension by a piezoelectric crystal. Vibrating mesh nebulizers comprise a solution or suspension in fluid contact with a vibrating diaphragm mesh. The vibrations of the mesh are used to generate an aerosol of the and inhalation and exhalation valves Nebulizers are commercially available and include Respirgard II®, Aeroneb®, Aeroneb® Pro, and Aeroneb® Go produced by Aerogen; AERx® and AERx Essence™ produced by Aradigm; Porta-Neb®, Freeway Freedom™, Sidestream, Ventstream and 1-neb produced by Respironics, Inc.; and PARI LC-Plus®, PARI LC-Stare, and e-Flow™ produced by PARI, GmbH.

Preferably the nebulizer is a vibrating mesh nebulizer, for example an e-Flow™ nebulizer. Nebulizers are further disclosed in WO2001032246, WO 01/34232, WO2001056639, WO2001085241, WO2002013896, WO2002064265, WO2003035153, WO2003035152, WO2004004813, WO2004014569, WO2004020029, WO2004028606, WO2004039442, WO2004041336, WO2004041335, WO2004052436, WO2004098689, WO2005032630, WO2005037246, WO2005042075, WO2006108556, WO2006084543, WO2006084546, WO2006128567, WO2007020073, WO2007118557, WO2010097119, WO2016015889, WO2008113651, WO2009135871, WO2010066714, WO2010094767, WO2010097119, WO2010097119, WO2010139730, WO2011134940, WO2012069531, WO2013013852, WO2012168181, WO2014040947, WO2014082818, WO2015091356, WO2015128375, WO2015193432, WO2016026802, WO2016102308, WO2017021441, WO2018167278, WO2019115771 and WO2019202085; incorporated herein by reference thereto.

Meter Dose Inhalers (MDI)

A propellant driven or pressurised metered dose inhaler (pMDI) releases a metered dose of an aerosol of a solution or suspension upon actuation of the inhaler. Suitably the solution or suspension comprising a halogenated salicylanilide (e.g. niclosamide) or a pharmaceutically acceptable salt thereof, and a cyclodextrin is formulated as a suspension or solution comprising a suitable propellant such as a halogenated hydrocarbon.

The propellants for use with the MDIs may be any propellants known in the art. Examples of propellants include chlorofluorocarbons (CFCs) such as dichlorodifluoromethane, trichlorofluoromethane, or dichlorotetrafluoroethane; hydrofluoroalkanes (HFAs); nitrogen and carbon dioxide. Suitably the propellant is an HFA, for example hydrofluoroalkane 134a (HFA 134 a), HFA-152a, or hydrofluoroalkane 227ea (HFA 227ea).

The MDI may be actuated with a trigger to release the aerosol for inhalation. Alternatively the MDI may be breath actuated, wherein inhalation by the user triggers release of the aerosol as the user draws in breath.

Dry Powder Inhalers

Dry powder inhalers (DPI) are suitable for the inhalation of powders comprising niclosamide or a pharmaceutically acceptable salt thereof. The DPI may be a reservoir device wherein the drug is contained within a reservoir in the device and the device delivers a unit dose of the drug from the drug reservoir. Alternatively the DPI may be a metered device wherein a unit dosages of the drug is loaded into the device and inhaled as an aerosol of the powder. Examples of DPI's include those described in A. H. de Boer et al., Expert Opinion on Drug Delivery, 2017. 14:4, 499-512.

DPIs are commercially available and include Novolizer®, Easyhaler®, Puivinal®, Taifun®, Twisthaler®, Turbuhaler®, Clickhaler®, SkyeHaler®, Airmex®, Spiromax®, Diskhaler®, Diskus®, Spiros®, Taper DPI, Jethaler®, MAGhaler®, Breezhaler® and NEXThaler® inhalers.

Intranasal Delivery Devices

The intranasal delivery device may be adapted to deliver a solution or suspension to the nasal mucosa. The intranasal delivery device may be a dropper, a metered dose spray pump (e.g. a multi-dose, or a bi-directional multidose spray pump), a squeeze bottle, a single-dose or duo-dose spray device, a nasal pressurized metered-dose inhaler (pMDI), a pulsation membrane nebulizer, a nasal sonic/pulsating jet nebulizer, a vibrating mesh nebulizer, a nasal atomizer or a gas- or electrically-driven atomizer.

Squeeze bottles are generally used to deliver over-the-counter medicines, such as decongestants. By manually squeezing a deformable (e.g plastic) air-filled bottle, the solution is atomized when delivered through a jet outlet.

Metered-dose spray pumps are commonly used for nasal drug delivery. Traditional spray pumps use preservatives to prevent contamination when the emitted liquid is replaced with air. However, more recent devices avoid the need for preservatives by using a collapsible bag, a moveable piston or a compressed gas to replace the emitted liquid, or alternatively use a filter to decontaminate the air. Commercially available nasal spray pumps are sold by Aptar Group.

Single-dose or duo-dose spray devices are intended for one-off or sporadic use, and/or where accurate dosing is important, for example for the administration of expensive drugs and vaccines. Commercially available devices include the MAD Nasal™ Intranasal Mucosal Atomization Device, and the Accuspray™ sold by Becton Dickinson Technologies.

Nasal pressurized metered-dose inhalers (pMDIs) have been developed which use hydrofluoroalkanes (HFAs) as a propellant. Such devices have been approved for the treatment of allergic rhinitis.

Pulsation membrane nebulizers generate an aerosol via a perforated vibrating membrane. Commercially available devices include the VibrENT device sold by PARI Pharma GmbH. Other types of commercially available nebulizers and atomizers include the Atomisor NL11S® sonic (a nasal sonic/pulsating jet nebulizer, DTF-Medical, France) the Aeroneb Solo® (a mesh nebulizer, Aerogen), OptiNose® devices comprising Bi-Directional™ technology, the ViaNase™ electronic atomizer (Kurve Technology Inc.) and nitrogen-driven atomizers (e.g. as sold by Impel Inc.).

In some embodiments, the intranasal delivery device is adapted to deliver a powder to the nasal mucosa. The intranasal delivery device may be a nasal powder inhaler (e.g. which is adapted for nasal delivery), a nasal powder sprayer or a nasal powder insufflator. Commercially available devices include Rhinocort Turbuhaler®, Twin-lizer™, Fit-lizer™ (SNBL), Unidose™ Xtra (Bespak), Monopowder (Aptar group), and the powder Exhalation Delivery System (EDS) sold by OptiNose Container In some embodiments, liquid formulations as described herein are administered using a dropper bottle. In some embodiments, a dropper bottle comprising a squeezable container is provided with a tapered dispenser that terminates in a discharge aperture. In some embodiments, to administer the liquid formulation, the discharge aperture is aligned above a target eye and the bottle is squeezed to urge out a drop or dose of the fluid.

Alternatively, liquid dispensers have been developed in which the formulation is supplied from a storage bottle through a dropper, for example (dropper bottles or EDO-Ophthiols). The aqueous formulation, in some embodiments, flows out of the dropper opening as a result of manual pressure being applied to the compressible storage bottle.

In some embodiments, the formulations as described herein are stored in a plastic or glass bottle. In some embodiments, the plastic bottle is a low-density polyethylene bottle.

In some embodiments, the formulation described herein is stored in a glass bottle with or without a liquid dispenser. In some embodiments, the plastic or glass bottle is opaque.

Infectious Diseases

Suitably the formulation of the invention may be used to treat an infectious disease, such as a pulmonary infection. The infectious disease may be a viral, bacterial, or fungal infection. The viral infection can be any viral infection that responds to treatment or prevention with a halogenated salicylanilide, such as niclosamide.

Viral Infections

For example, the viral infection can be caused by or associated with a virus selected from the families Coronaviridae (e.g. Alphacoronavirus, Betacoronavirus, Gammacoronavirus and Deltacoronavirus), Picornaviridae (e.g. Enteroviruses, such as rhinoviruses, suitable Human rhinoviruses (HRVs)), Flaviviridae (e.g. Zika virus (ZIKV), dengue (e.g. DENV 1-4), West Nile virus (WNV), yellow fever virus (YFV), and Japanese encephalitis virus (JEV), Hepatitis C virus (HCV), Filoviridae (e.g. Ebolavirus)), Togaviridae (e.g. Alphaviruses such as Chikungunya virus (CHIKV)), and Adenoviridae (e.g. Human adenoviruses (HAdVs)).

Viruses which infect or which carry out at least one phase of their life cycle or are pathogenic in the respiratory tract are of most interest in the present invention. Such viruses can in some cases enter a subject via the respiratory tract (e.g. they are capable of transmission through inhalation, e.g. via airborne or droplet transmission), and/or they may carry out initial or further stages of replication in the respiratory tract (e.g. upper or lower respiratory tract). Some well-known examples of viruses that are transmitted through airborne or droplet transmission include coronaviruses, influenza virus, parainfluenza virus, adenoviruses, respiratory syncytial virus, human metapneumovirus. Other viruses not consider classical airborne or droplet transmitted virus can in some circumstances be transmitted through the air, e.g. is bodily fluids containing the virus are aerosolised. Furthermore, other viruses that are not transmitted through the air may replicate or be pathogenic in the respiratory tract, and thus can be treated using the inhalable composition of the invention.

Viruses that are transmitted through airborne or droplet transmission and/or which cause viral respiratory disease are of particular interest in the present invention.

The formulations of the invention may be administered by inhalation to provide the treatment or prevention of viral infection. In embodiments the viral infection is caused by or associated with a respiratory virus. Thus it may be that the viral infection is a respiratory tract infection. The viral infection may be an upper respiratory tract infection. The viral infection may be a lower respiratory tract infection, for example a viral infection affecting the lungs.

In some embodiments, the viral infection is caused by or associated with a virus selected from respiratory syncytial virus, influenza virus, parainfluenza virus, human metapneumovirus, coronavirus (e.g. severe acute respiratory syndrome coronavirus (SARS-CoV), severe acute respiratory syndrome coronavirus (SARS-CoV-2), Middle East respiratory syndrome coronavirus (MERS-CoV)), Ebola virus (EBOV), flavivirus, a human rhinovirus (HRVs), human adenovirus (HAdV), and Epstein-Barr virus (EBV).

In some embodiments, the viral infection is a respiratory tract infection (RTI). A respiratory tract infection (RTI) is an infectious diseases involving the respiratory tract. An infection of this type is normally further classified as an upper respiratory tract infection (URI or URTI) or a lower respiratory tract infection (LRI or LRTI). The RTI can be an upper or lower RTI. Lower respiratory infections, such as pneumonia, tend to be far more serious conditions than upper respiratory infections, such as the common cold. The upper respiratory tract is generally considered to be the airway above the glottis or vocal cords, sometimes it is taken as the tract above the cricoid cartilage. This part of the tract includes the nose, sinuses, pharynx, and larynx. Symptoms of URIs can include cough, sore throat, runny nose, nasal congestion, headache, low grade fever, facial pressure and sneezing. The lower respiratory tract consists of the trachea (wind pipe), bronchial tubes, the bronchioles, and the lungs. Lower respiratory tract infections are generally more serious than upper respiratory infections. LRIs are the leading cause of death among all infectious diseases. The two most common LRIs are bronchitis and pneumonia.

The virus can be a RNA virus or a DNA virus. In certain embodiments the viral infection is caused by or associated with an RNA virus. In certain embodiments the viral infection is caused by or associated with a DNA virus. In certain embodiments the viral infection is caused by or associated with a positive-sense strand RNA virus.

In certain embodiments the viral infection is caused by or associated with a virus selected from respiratory syncytial virus, influenza virus, parainfluenza virus, a pneumovirus (e.g. human metapneumovirus), a coronavirus (e.g. severe acute respiratory syndrome coronavirus (SARS-CoV), severe acute respiratory syndrome coronavirus (SARS-CoV-2), Middle East respiratory syndrome coronavirus (MERS-CoV)), human rhinovirus (HRVs), human adenovirus (HAdV).

In some embodiments the virus is an RNA virus that causes or is associated with a RTI.

In some embodiments the viral infection can cause or may be associated with acute respiratory syndrome, e.g. severe acute respiratory syndrome (SARS). Viruses which are known to cause severe acute respiratory syndrome (SARS) include coronaviruses such as a SARS viruses or MERS viruses, e.g. SARS-CoV, SARS-CoV-2 or MERS-CoV. In one embodiment the viral infection causes SARS.

The viruses of the Pneumoviridae family are negative sense, single-stranded, RNA viruses. Two genera within the Pneumoviridae family are Metapneumo virus and Orthopneumovirus. Particular species of Metapneumovirus are avian metapneumovirus (AMPV) and human metapneumovirus (HMPV). Particular species of Orthopneumovirus are Bovine respiratory syncytial virus (BRSV), Human respiratory syncytial virus (HRSV) and Murine pneumonia virus (MPV). Viruses in the Pneumoviridae family are typically transmitted through respiratory secretions and are often associated with respiratory infections. In certain embodiments the viral infection is caused by or associated with Human respiratory syncytial virus (HRSV). Thus it may be that the virus is caused by or associated with a virus selected from: HRSV-A2, HRSV-B1 and HRSV-S2.

Coronaviridae viruses are a family of enveloped, positive-stranded, single-stranded, spherical RNA viruses. The Coronaviridae family includes two sub-families, Coronavirus and Torovirus. The Coronavirus genus has a helical nucleocapsid, and Torovirus genus has a tubular nucleocapsid. Within the Coronavirus sub-family are the following genera: Alphacoronavirus, Betacoronavirus, Gammacoronavirus and Deltacoronavirus. Genera within the Torovirus subfamily are Bafinivirus and Torovirus. In certain embodiments the viral infection is caused by or associated with a coronavirus. Thus is may be that the viral infection is caused by or associated with a virus selected from Alphacoronavirus, Betacoronavirus, Gammacoronavirus and Deltacoronavirus. In a preferred embodiment the viral infection is caused by or associated with a Betacoronavirus.

Human coronaviruses usually cause mild to moderate upper-respiratory tract illnesses, like the common cold, that last for a short amount of time (although some coronaviruses can be deadly). Symptoms may include runny nose, cough, sore throat, and fever. These viruses can sometimes cause lower-respiratory tract illnesses, such as pneumonia. This is more common in people with cardiopulmonary disease or compromised immune systems, or the elderly.

In some embodiments, the viral infection is a common cold. The common cold may be caused by or associated with a virus selected from respiratory syncytial virus (RSV), parainfluenza virus, a pneumovirus (e.g. human metapneumovirus), a coronavirus, rhinovirus (e.g. human rhinovirus, HRVs), adenovirus (e.g. human adenovirus, HAdV), and enterovirus.

Middle East respiratory syndrome coronavirus (MERS-CoV) is a member of the Betacoronavirus genus, and causes Middle East Respiratory Syndrome (MERS). MERS is an acute respiratory illness. About half of the individuals confirmed to have been infected with MERS died. There is no current treatment or vaccine for MERS.

Another member of the Betacornavirus genus is SARS coronavirus (SARS-CoV). SARS-Co-V is the virus that causes severe acute respiratory syndrome (SARS). SARS was first reported in Asia in February 2003. SARS is an airborne virus, and can spread by the inhalation of small droplets of water that an infected individuals releases into the air (for example, by coughing and/or sneezing), touching a contaminated surface and/or by being in close proximity of an infected individual.

In certain embodiments the viral infection is caused by or associated with severe acute respiratory syndrome coronavirus (SARS-CoV), severe acute respiratory syndrome coronavirus 2 (SARS-CoV-2), Middle East respiratory syndrome coronavirus (MERS-CoV), HCoV-229E, HCoV-NL63, HCoV-0C43 and HKU1.

In certain embodiments the viral infection is caused by or associated with a coronavirus that causes severe acute respiratory syndrome (SARS), such as a SARS virus or MERS virus, e.g. SARS-CoV, SARS-CoV-2, or MERS-CoV. Preferably the viral infection is caused by or associated with SARS-CoV-2.

Pathogenic respiratory viral infections can cause disease and symptoms associated with the viral infection. In certain embodiments the inhalable pharmaceutical composition is for use in the prevention or treatment of a disease or condition associated with a respiratory viral infection. Thus is may be that the inhaled composition is for use in the treatment or prevention of a respiratory syndrome caused by or associated with a respiratory viral infection. For example the treatment or prevention of severe acute respiratory syndrome (SARS). Thus it may be that the inhaled composition of the invention is for use in the prevention or treatment of severe acute respiratory syndrome caused by SARS-CoV, SARS-CoV-2, or MERS-CoV, preferably the treatment or prevention of severe acute respiratory syndrome caused by SARS-CoV-2. In certain embodiments the inhaled composition of the invention is for use in the treatment of a respiratory syndrome selected from: pneumonia, influenza and croup. Thus it may be that the inhaled composition is for use in the treatment or prevention of pneumonia caused by a respiratory viral infection.

In a preferred embodiment the formulation is for use in the treatment of COVID-19. COVID-19 can be diagnosed by any method known to the skilled person. Samples (e.g., sputum, mucus, sera, nasal aspirate, throat swab, bronchoalveolar lavage or other types of body fluids) from subjects can be obtained and tested for the presence of SARS-CoV-2. Exemplary methods for diagnosing an infection with SARS-Cov-2 include, but are not limited to, detection of a nucleotide sequence of a SARS-CoV-2 virus (e.g. using PCR), detection of a SARS-Cov-2-associated coronavirus antigen, and antibodies or fragments thereof that immunospecifically bind to a SARS-CoV-2-associated coronavirus antigen.

An example of a nucleotide sequence of a SARS-CoV-2 virus is described by Wu et al. (Nature 579, 265-269 (2020) (Genbank accession no. MN908947.3, isolate Wuhan-Hu-1). The subject may be infected with a SARS-CoV-2 virus having a genome sequence which is at least 95%, at least 96%, at least 97%, at least 98%, at least 99%, at least 99.5%, at least 99.6%, at least 99.7%, at least 99.8%, at least 99.9%, at least 99.91%, at least 99.92%, at least 99.93%, at least 99.94%, at least 99.93%, at least 99.95%, at least 99.96%, at least 99.97%, at least 99.98%, or at least 99.99% identical to MN908947.3.

Subjects with viral infections can develop serious conditions associated with the viral infection. Treatment of a subject with a respiratory viral infection using the inhaled composition of the invention may prevent or treat a condition selected from: sepsis, pneumonia or organ failure associated with a respiratory viral infection. In some embodiments the inhaled composition is for use in the treatment or prevention of sepsis caused by or associated with the respiratory viral infection. In some embodiments the inhaled composition is for use in the treatment or prevention of pneumonia caused by or associated with the respiratory viral infection. The pneumonia may be viral pneumonia or bacterial pneumonia (e.g. bacterial pneumonia caused by or associated with secondary bacterial infection in the lung of a subject). Thus it may be that the inhaled composition of the invention is for use in the treatment or prevention of viral pneumonia.

In certain embodiments the viral infection is caused by or associated with influenza virus. The influenza virus may be type A; type B, type C or type D. Type A and B viruses cause seasonal epidemics in humans, while type A viruses have caused several pandemics. Type C viruses generally cause mild illness and are not generally associated with epidemics. Type D viruses primarily affect cattle. Type A viruses can be divided into subtypes based on their surface proteins hemagglutinin (H) and neuraminidase (N). There are 18 different hemagglutinin proteins (designated H1 to H18) and 11 different neuraminidase proteins (designated N1 to N11). This gives 198 potential influenza A type combinations, although only 131 subtypes have been detected to date. The viral infection may be caused by or associated with a Type A influenza virus selected from H1N1, H1N2, H2N2, H3N2, H5N1, H7N7, H9N2, H7N2, H7N3, H10N7, H7N9 and H6N1. Type B viruses are not classified into subtypes, but can be categorised into lineages. Type B viruses may belong to either the B/Yamagata or B/Victoria lineage.

In certain embodiments the formulation of the invention is for use in the treatment or prevention of bacterial pneumonia caused by or associated with a respiratory viral infection (i.e. the treatment of bacterial pneumonia secondary to the viral infection). Thus it may be that the inhaled composition of the invention is for use in the treatment or prevention of *Streptococcus pneumoniae*. In a particular embodiment the inhaled composition of the invention is for use in the treatment or prevention of Staphylococcal pneumonia.

The antibacterial effects of halogenated salicylanilides such as niclosamide may provide a particularly effective treatment secondary infections such as bacterial pneumonia. The formulations of the invention have both antiviral and antibacterial action, and accordingly can be used to treat both viral and bacterial pathogens in the lung. Accordingly, also provided is a formulation of the invention for use as an antibacterial agent to target a bacterial infection that is secondary to a respiratory viral infection (e.g. Gram-positive bacteria). Thus it may be that the formulation of the invention is for use in the treatment of secondary bacterial infection in a subject with a respiratory viral infection, wherein the secondary bacterial infection is caused by or associated with a Gram-positive bacteria, preferably a bacteria selected from one or more of: *S. aureus* (e.g. MRSA), *S. pneumoniae, H. influenzae* and *M. catarrhalis.*

Certain embodiments provide a formulation of the invention for use as an antibacterial agent to target one or more bacteria which can cause or contribute to pneumonia. In these embodiments it may be that the bacteria targeted are Gram-positive bacteria, for example one or more of *S. aureus* (e.g. MRSA), *S. pneumoniae, H. influenzae* and *M. catarrhalis*. Thus it may be that the inhaled composition eradicates or reduces the bacteria can cause or contribute to pneumonia.

In certain embodiments the formulation of the invention is for use in the treatment or prevention of a symptom of a viral infection (e.g. SARS-CoV-2) selected from fever (e.g. a fever above 38° C.), cough, sore throat, shortness of breath, respiratory distress, and pneumonia. Suitably the inhaled composition is used to treat severe acute respiratory syndrome (SARS).

In certain embodiments the formulation of the invention may for use in reducing mucus production and/or secretion caused by or associated with a respiratory viral infection.

In certain embodiments the formulation of the invention may for use in reducing bronchoconstriction caused by or associated with a respiratory viral infection.

Subjects with viral infections, particularly respiratory viral infections, are prone to developing pulmonary fungal infections. Niclosamide is known to have antifungal properties (Garcia et al., Sci Rep. 2018; 8(1):11559. Published 2018 Aug. 1. doi:10.1038/s41598-018-29973-8). Accordingly, the formulation of the invention may provide an effective treatment of opportunistic pulmonary fungal infections associated with a viral infection. In certain embodiments there is provided a formulation of the invention for use in the treatment of a pulmonary fungal infection caused by or associated with a viral infection (e.g. a respiratory viral infection). The fungal infection may be an opportunistic pulmonary fungal infection. In certain embodiments the pulmonary fungal infection is a *Candida* Spp. infection, for example a *Candida albicans*. In certain embodiments the formulation of the invention is for use in the treatment or prevention of pulmonary candidiasis. Particularly the formulation of the invention is for use in the treatment or prevention of pulmonary candidiasis in a subject with a viral infection, preferably a respiratory viral infection.

Halogenated salicylanilides such as niclosamide have anti inflammatory properties. Accordingly the formulation of the invention may be beneficial in reducing, ameliorating or treating pulmonary inflammation associated with respiratory viral infections, because halogenated salicylanilides such as niclosamide have both antiviral and anti inflammatory properties.

In certain embodiments there is provided a formulation of the invention for use in the treatment or prevention of pulmonary inflammation caused by or associated with respiratory viral infection. For example the inhaled composition may reduce or eliminate inflammation of tissues in the respiratory tract.

In certain embodiments the formulation is for use in preventing or repressing pro-inflammatory cytokines caused by or associated with the viral infection. Thus it may be that the inhaled pharmaceutical composition reduces one or more of CRP leukocytes, MB, IL-6, IL-10, IL-2, IFN$\gamma$, IP10, MCP1, GCSF, IP10, MCP1, MIP1A, and/or TNF$\alpha$, particularly reducing serum CRP. In some embodiments the formulation reduces levels of IL-6 in a subject with a respiratory viral infection.

Viral infections (including, but not limited to SARS CoV-2) can induce cytokine release syndrome (CRS) (also known as a cytokine storm syndrome (CSS)). CRS is a systemic inflammatory response triggered by the viral infection and results in the sudden release of large numbers of pro-inflammatory cytokines which can damage organs and in particular may lead to respiratory failure. Recent publications suggest that cytokine storm is observed in some patients with severe forms of COVID-19 (Zhang et al, International Journal of Antimicrobial Agents https://doi.org/10.1016/j.ijantimicag.2020.105954, available online 29 Mar. 2020). In some embodiments there is provided a formulation of the invention for use in the prevention, repression or treatment of cytokine release syndrome in a subject with a respiratory viral infection (e.g. a subject infected with SARS-CoV2, SARS or MERS).

In certain embodiments the formulation has an antiviral effect on the virus, for example by preventing or inhibiting viral replication. Without wishing to be bound by theory, it is believed that the formulation can act as an antiviral by to inhibiting or preventing viral replication in at least the respiratory tract of a patient. Accordingly, in some embodiments the formulation of the invention is for use in preventing or inhibiting viral replication in a subject with a viral infection (e.g. a respiratory viral infection) In some embodiments the formulation may reduce or eliminate the viral load in the subject.

It will be appreciated that the combined treatment of multiple conditions using the formulation of the present invention provides significant advantages over the use of multiple therapies.

In some embodiments of the invention the aerosol or solution is used as an anti-viral and as an anti-inflammatory and/or as an anti-bacterial. Thus, in some embodiments the aerosol or solution is used as at least a dual therapy or triple therapy. Thus, in some embodiments the aerosol or solution can be used to target viral infection and inflammation and/or bacterial infection for the treatment of an RTI, for example in a coronaviral infection such as SARS. In some embodiments the aerosol or solution is used as an anti-viral, as an anti-inflammatory and as an anti-bacterial for the treatment of an RTI, for example in a coronaviral infection such as SARS.

In some embodiments of the invention the formulation is used to treat a viral infection as an antiviral (e.g. to prevent viral replication) and to further provide one or more of the following additional therapeutic effects:
anti-bacterial;
anti-inflammatory;
reduction or prevention of bronchoconstriction/to cause bronchodilation; and/or reduction of mucus production and/or secretion.

The subject infected with a respiratory viral infection may be asymptomatic at the early stages of a viral infection. Treatment of asymptomatic subjects may prevent the viral infection becoming symptomatic and/or developing diseases or medical conditions associated with the respiratory viral infection. Accordingly also provided is a formulation of the invention for use in the treatment of an asymptomatic subject infected with a virus. In some embodiments the virus is a respiratory virus (e.g. a SARS virus such as SARS-CoV-2).

Some viral infections become contagious before symptoms emerge in a subject infected with the virus, for example as is the case with SARS-Cov-2. This can result in high rates of transmission of the virus in a population, because the infected host does not know that they are contagious and inadvertently spreads the virus through social contact etc. Transmission of a virus by asymptomatic subjects can be particularly dangerous after an initial infection is contained in a population, because asymptomatic, but contagious, subjects can trigger a resurgence of infections and a "second wave" of viral infection. Using the formulation of the invention to treat an asymptomatic subject with a viral infection may reduce the time that a subject is contagious by, for example reducing or eliminating the virus from the subject and/or to speed up seroconversion in the subject (i.e. the production of antibodies to the virus by the subject's immune system). Treatment using the formulation of the invention may reduce the viral shedding from the subject, thereby making the subject less contagious. Viral shedding refers to the number of virus leaving the body of the subject in for example mucous droplets resulting from coughing or sneezing, or present in other excreta.

Accordingly, in some embodiments there is provided a formulation of the invention for use in the treatment of a viral infection in an asymptomatic subject, wherein the treatment reduces or eliminates the viral load in the subject. In some embodiments there is provided a formulation of the invention for use in the treatment of a viral infection in an asymptomatic subject, wherein the treatment accelerates seroconversion in the subject. In some embodiments there is provided a formulation of the invention for use in the treatment of a viral infection in an asymptomatic subject, wherein the treatment reduces inter-subject transmission of the virus.

The detection of a viral infection in an asymptomatic subject may be achieved using known testing methods, for example tests which detect the presence of the virus in saliva samples such as real-time reverse transcription polymerase chain reaction (rRT-PCR) or PCR methods. In some embodiments there is provided a formulation of the invention for use in the treatment or prophylaxis of a subject who has received a positive diagnosis of a viral infection, such as COVID-19 (SARS-CoV-2). The subject may be suffering from mild, moderate or severe COVID-19, or they may be asymptomatic. Prophylactic treatment of subjects who have not received a positive test for the presence of SARS-CoV-2 infection, or who have not been tested, is also envisaged.

Symptoms of COVID-19 are non-specific and the disease presentation can range from no symptoms (asymptomatic) to severe pneumonia and death. The clinical progression of COVID-19 shows a biphasic pattern. The first phase is characterized by fever, cough, fatigue and other systemic symptoms like dizziness and headache, shortness of breath, rhinorrhoea, sore throat, diarrhoea and inappetence. Fever is seen in most of the patients with an estimated median duration of 10 days (95 confidential intervals after onset of symptoms (Chen et al. Clinical progression of patients with COVID-19 in Shanghai, China. J Infect. 2020; 80(5):e1-e6.).

As the disease progresses into the second phase, symptoms begin to relieve in most of the patients and radiological improvement occurs in parallel. In line with body temperature reduction, patients also become PCR negative with their upper respiratory tract samples (mean time to viral clearance is around 11 days). There is however a small sub-group of patients (~5%) which present with respiratory failure, septic shock, and multiorgan dysfunction, resulting in higher fatality rates. Persistent fever, lung damage and diseases progression can be partially explained by uncontrolled viral replication. The persistence of COVID-19 can also induce excessive but aberrant non-effective response which is associated with cytokine storm.

Patients with "mild" COVID-19, as used herein, are subjects with a score of 2, 3 or 4 on the modified WHO scale described below. Subjects may be ambulatory or hospitalized.

They show symptoms of COVID-19 that could include fever, cough, sore throat, malaise, headache, shortness of breath, muscle pain, loss of taste and/or smell, ocular symptoms (e.g. one or more of conjunctival hyperemia, chemosis, epiphora, or increased secretions) and/or gastrointestinal symptoms (e.g. diarrhoea) of variable intensity and they can either have no or mild signs of viral pneumonia. They may display a limitation of daily activities. They do not need oxygen treatment.

Patients with "moderate" COVID-19, as used herein, are subjects with a score of 5 on the modified WHO scale described below. Subjects are hospitalized with COVID-19 needing treatment with oxygen by mask or nasal prongs. They show symptoms that could include fever, cough, sore throat, malaise, headache, muscle pain and/or gastrointestinal symptoms of variable intensity. They have a moderate pneumonia.

Patients with "severe" COVID-19, as used herein, are subjects with a score of 6, 7 or 8 on the modified WHO scale described below. These subjects require intensive care and/or mechanical ventilation or extra-corporeal membrane oxygenation. Such patients may display hypoxemia, extrapulmonary hyper-inflammation, severe pneumonia, vasoplegia, respiratory failure, cardiopulmonary collapse and/or systemic organ involvement. Markers of systemic inflammation (e.g. IL-2, IL-6, IL-7, granulocyte colony-stimulating factor, macrophage inflammatory protein 1-α, tumor necrosis factor-α, C-reactive protein, ferritin, and/or D-dimer) may be elevated.

By targeting patients at a stage where viral replication is high but has not yet led to severe tissue damage, the treatment may reduce duration of symptoms, minimize contagiousness, and prevent progression of severity and poor outcome.

Accordingly, in some embodiments there is provided a formulation of the invention for use in the treatment of a viral infection in a subject suffering from mild or moderate COVID-19. In some embodiments, the subject is suffering from mild COVID-19 and the formulation is administered intranasally. In some embodiments, the subject is suffering from mild COVID-19 and the formulation is administered intranasally and ocularly (e.g. as eye drops). In some embodiments, the subject is suffering from moderate COVID-19 and the formulation is administered intranasally. In some embodiments, the subject is suffering from moderate COVID-19 and the formulation is administered intraorally by inhalation. In some embodiments, the subject is suffering from moderate COVID-19 and the formulation is administered intranasally and intraorally by inhalation. In some embodiments, the subject is suffering from moderate COVID-19 and the formulation is administered intranasally, intraorally by inhalation and ocularly (e.g. as eye drops).

In some embodiments, the subject is identified as being at risk of disease progression. For example, the subject may be identified as being at risk of progressing from mild to moderate, or from moderate to severe COVID-19. In some embodiments, the subject may be identified as being at risk of an increase in the subject's score on the modified WHO scale, as described below. A skilled doctor or nurse will be capable of identifying at-risk subjects. For example, a subject who is at risk of disease progression may be identified based on one or more factors, which may include clinical parameters (such as the subject's respiratory status, blood oxygen saturation, temperature, severity of flu-like symptoms, chest X-ray or other scans, inflammatory biomarker levels, viral load and the presence of underlying conditions) and, optionally, non-clinical parameters (such as subject's age and gender).

The treatment may reduce or eliminate the viral load in the subject (e.g. the viral load in sputum or blood), for example, it may be that the treatment reduces the viral load in the nasal cavity. It may be that the treatment reduces the viral load in the lungs of a subject. In some embodiments, the treatment reduces the time taken to cure the disease, relative to a patient not treated with the formulation of the invention. The treatment may avoid the need for hospitalization in patients with mild COVID-19, or reduce hospitalization time for patients with moderate COVID-19. The treatment may prevent the progression of the disease. For example, the treatment may prevent progression from mild to moderate, or from moderate to severe COVID-19. The treatment may prevent an increase in a subject's score on a modified WHO scale as described below. The treatment may reduce or eliminate the need for oxygen therapy. The treatment may increase blood oxygen levels. The treatment may prevent or reduce the risk of respiratory failure. The treatment may reduce the time for viral clearance from a subject. The treatment may reduce or eliminate viral colonization. For example the treatment may reduce or eliminate viral colonization in the nasal cavity. It may be that treatment reduces or eliminates viral colonization in the lungs.

In some embodiments, there is provided a formulation of the invention for use in the treatment of a viral infection in subject suffering from severe COVID-19.

The treatment may reduce the time the patient spends in intensive care, relative to a patient not treated with the formulation of the invention. In some embodiments, the treatment improves the efficacy of a co-administered drug, such as an anti-inflammatory agent. The treatment may reduce the severity of symptoms, the recovery time, and/or the long term effects of the disease.

In some embodiments, there is provided a formulation of the invention for use in the treatment of a viral infection (e.g. COVID-19), wherein said treatment includes one or more of the following: a reduction in the severity of flu-like signs and symptoms (e.g. temperature); an improvement in the respiratory status of the subject as assessed by oximetry (blood oxygen saturation); an improvement in the NEWS2 score; an improvement in the score on the modified WHO ordinal scale, as described herein; reduction or elimination of pulmonary inflammation and/or edema; an improvement in respiratory function; a reduction in shortness of breath; a reduction in the time to viral clearance; a reduction in the time to discharge from hospital; reduced viral load; a reduction in inflammatory serum markers (e.g. CRP, procalcitonin). In some embodiments, treatment results in subjects having an improvement in the score on the modified WHO ordinal scale by 1 to 6 grades, 2 to 5 grades, or 3 to 4 grades. In some embodiments, treatment results in subjects having an improvement in the NEWS2 score by from 1 to 6 points, from 2 to 5 points, or from 3 to 4 points.

Also provided is a prophylactic treatment wherein the formulation of the invention is administered to a subject to prevent or reduce the risk of contracting a viral infection. In certain embodiments there is provided a formulation of the invention for use in reducing the risk of, or preventing, a subject contracting a viral infection. Such prophylactic treatments may be particularly beneficial to subjects that may be exposed to high levels of a virus, for example doctors, nurses and healthcare workers that are caring for people with viral infections.

In some embodiments, the formulation of the invention is prophylactically administered to a subject who has been, or is suspected as having been, in close proximity with a person who is diagnosed as being infected with SARS-CoV-2. For example, family, co-workers and/or other close contacts of an infected individual, who are identified as having being at risk of exposure to the virus, may be administered the formulation of the invention as a prophylactic treatment. The close contacts of the infected individual may be identified via a tracking and tracing program, such as a government-operated program. Prophylactic treatment of subjects after suspected exposure to an infected person may be beneficial in preventing further spread of the virus. In some embodiments, the subject starts the prophylactic treatment no more than 7 days, no more than 6 days, no more than 5 days, no more than 4 days, no more than 3 days, no more than 2 days or no more than 24 hours after the exposure, or suspected exposure, to the infected individual. The close contacts may be subjects who are identified as having been in close proximity to the infected individual and include, for example, subjects who share a home, office, school or mode of transport with the infected individual, those who have taken part in a sport or other social activity with the infected individual, and those who may have come into close proximity with the infected individual in a public space such as a restaurant, bar, café, transport terminal, library, hospital or other medical facility, or shop. Suitably, prophylactic treatments may be administered intranasally. It may be that prophylactic treatment is administered to the general public, for example in the case of an epidemic.

The treatments and prophylactic treatments described herein may also be particularly beneficial to subjects who are at high or moderate risk from COVID-19. These subjects include: those with an existing disease or condition, such as diabetes (Type I or Type II diabetes mellitus), cancer, heart disease (such as heart failure, coronary artery disease and cardiomyopathy), hypertension, cerebrovascular disease, vasculitis, SCID, sickle cell disease (including sickle cell anaemia), cystic fibrosis, thalassemia, pulmonary fibrosis, interstitial lung disease, COPD, asthma, emphysema, bronchitis, kidney disease (including chronic kidney disease, diabetic nephropathy, membranous nephropathy and glomerular disease, such as glomerulonephritis, minimal change nephropathy, focal segmental glomerulosclerosis, IgA nephropathy, primary membranous nephropathy, membranoproliferative glomerulonephritis and lupus nephritis), chronic liver disease, hepatitis, autoimmune disease (including systemic lupus erythematosus (SLE), Anti-GBM, rheumatoid arthritis, psoriatic arthritis, connective tissue disease, spondyloarthritis, polymyalgia rheumatica, inflammatory bowel disease (including crohn's disease and ulcerative colitis), coeliac disease, aplastic anaemia, Addison's disease, Graves' disease, Hashimoto's thyroiditis, myasthenia gravis, autoimmune vasculitis, pernicious anaemia and Sjögren's syndrome) or a condition affecting the brain or nerves (such as Parkinson's disease, motor neurone disease, multiple sclerosis or cerebral palsy); subjects who have had an organ transplant (including kidney, liver, lung and/or heart transplant recipients); subjects who have had their spleen removed; subjects receiving chemotherapy, immunotherapy, antibody therapy or radiotherapy; subjects receiving protein kinase inhibitors or PARP inhibitors; subjects who have had a blood, bone marrow or stem cell transplant (e.g. in the last 6-12 months); subjects who are immunocompromised (including subjects taking immunosuppressants (e.g. ciclosporin, tacrolimus, azathioprine, mycophenolate mofetil or mycophenolic acid, belatacept, methotrexate, tocilizumab, abatacept, leflunomide, prednisolone, anti-TNF (e.g. infliximab, adalimumab, etanercept), cyclophosphamide, rituximab or alemtuzumab), or steroids, subjects with HIV or AIDS); subjects on dialysis (including haemodialysis and peritoneal dialysis); subjects who are very obese (with a BMI of at least 30, at least 40 or above); subjects who are pregnant; subjects who smoke; and subjects who are over 50, 60 or 70 years of age, in particular subjects over 75, 80, 85 or 90 years of age. Thus, in some embodiments there is provided a formulation of the invention for use in reducing the risk of, or preventing, a subject contracting a viral infection (e.g. COVID-19), wherein the subject is selected from the groups defined above. In certain embodiments there is provided a formulation of the invention for use in treating a viral infection in a subject (e.g. COVID-19), wherein the subject is selected from the groups defined above. In some embodiments the formulation is administered intranasally.

In some embodiments, said treatment comprises administering the formulation of the invention in combination with a further therapeutic or prophylactic agent. The further therapeutic or prophylactic agent may be an anti-viral agent (e.g. Remdesivir), an anti-inflammatory agent (e.g. a steroid, such as dexamethasone), an immunosuppressive agent, a neutralizing antibody or an anti-thrombotic agent. Combination therapy may be particularly beneficial for subjects with a severe viral infection (e.g. severe COVID-19).

Bacterial Infections

In some embodiments, the formulations and methods described herein are used in the treatment of bacterial infections, for example pulmonary bacterial infections. The bacterial infection may be a primary infection (i.e. the primary or only disease the subject is suffering from), or the bacterial infection may be secondary infection associated with another (primary) infection (e.g. a viral infection) or an inflammatory disease.

In some embodiments, the formulations and methods described herein are used for the treatment or prevention of a bacterial infection in the lungs of a subject having a chronic lung condition, such as cystic fibrosis (CF), non-cystic fibrosis bronchiectasis (non-CFBE), chronic obstructive pulmonary disorder (COPD), or non-tuberculous mycobacterial (NTM) pulmonary infection.

In some embodiments, the bacterial infection is caused by a gram-positive bacteria, such as: *Corynebacterium diphtheriae, Corynebacterium ulcerans, Streptococcus pneumoniae, Streptococcus agalactiae, Streptococcus pyogenes, Streptococcus milleri; Streptococcus* (Group G); *Streptococcus* (Group C/F); *Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, and *Staphylococcus saccharolyticus*. In some embodiments, the bacteria is a gram-positive anaerobic bacteria, by non-limiting example these include *Clostridium difficile, Clostridium perfringens, Clostridium tetini*, and *Clostridium botulinum*. In some embodiments, the bacterial infection is caused by an acid-fast bacteria, by non-limiting example these include *Mycobacterium tuberculosis, Mycobacterium avium, Mycobacterium intracellulare*, and *Mycobacterium leprae*. In some embodiments, the bacterial infection is caused by an atypical bacteria, by non-limiting example these include *Chlamydia pneumoniae* and *Mycoplasma pneumoniae*.

In some embodiments, the bacterial infection is caused by a bacterium selected from: *S. aureus, S. pneumoniae, H. influenzae, M. catarrhalis* and *S. pyogenes*.

Bacterial Skin Infections

In some embodiments there is provided a formulation of the invention for the treatment (preferably the topical treatment) of a skin infection caused by or associated with Gram-positive bacteria.

In some embodiments the formulation of the invention is for use in the treatment of from impetigo, sycosis barbae, superficial folliculitis, paronychia erythrasma, acne, secondary infected dermatoses, carbuncles, furonculosis, ecthyma, cellulitis, erysipelas, necrotising fasciitis and secondary bacterial skin infections of wounds, dermatitis, scabies, diabetic ulcer, rosacea or psoriasis. For example the composition of the invention may be for use in the topical treatment of an atopic dermatitis lesion, wherein said lesion is infected with Gram-positive bacteria.

In some embodiments the formulation of the Invention is for use in the topical prevention or treatment of an outer ear infection caused by or associated with a Gram-positive bacteria.

It may be that the Gram-positive bacteria is a *Staphylococcus* spp., *Streptococcus* spp. or *Propionibacterium* spp. The Gram-positive bacteria may be a *Staphylococcus* spp. or *Streptococcus* spp. The Gram-positive bacteria may be selected from *Staphylococcus aureus* or *Streptococcus pyogenes*. The Gram-positive bacteria may be *Propionibacterium* spp., for example *Propionibacterium acnes*. It may be that the Gram-positive bacteria is not a propionibacteria e.g. that it is not *Propionibacterium acnes*.

In some embodiments, the population of Gram-positive bacteria includes coccus Gram-positive bacteria. In some embodiments, the Gram-positive bacteria are from the *Streptococcus* or *Staphylococcus* genus.

In some embodiments, the Gram-positive bacteria are from the *Streptococcus* genus. It may be that the Gram-positive bacteria are *Streptococcus* selected from *Streptococcus pneumoniae, Streptococcus pyogenes, Streptococcus suis, Streptococcus agalactiae* or *Streptococcus viridans*.

In some embodiments, the Gram-positive bacteria are *Streptococcus pyogenes*.

In some embodiments, the Gram-positive bacteria are from the *Staphylococcus* genus. It may be that the Gram-positive bacteria are *Staphylococcus* selected from *Staphylococcus epidermidis, Staphylococcus aureus, Staphylococcus saprophyticus* or *Staphylococcus lugdunensis*. In some embodiments, the coccus Gram-positive bacteria are *Staphylococcus aureus* (e.g. methicillin-resistant *Staphylococcus aureus*).

It may be that the population of Gram-positive bacteria includes antibiotic-resistant Gram-positive bacteria. It may be that the Gram-positive bacteria is an antibiotic resistant strain. For example, the Gram-positive bacteria described herein may be resistant to an antibiotic other than a halogenated salicylanilide (for example the bacteria is resistance to a drug other than closantel, rafoxanide, oxyclozanide or niclosamide, or a pharmaceutically acceptable salt or solvate thereof).

It may be that the Gram-positive bacteria is resistant to a drug selected from fusidic acid, mupirocin, retapamulin, erythromycin, clindamycin and a tetracycline (for example tetracycline, minocycline or doxycycline).

It may be that the Gram-positive bacteria is resistant to a drug selected from erythromycin, clindamycin or a tetracycline (for example tetracycline, minocycline or doxycycline).

It may be that the Gram-positive bacteria is resistant to a drug selected from fusidic acid, mupirocin and retapamulin.

It may be that the bacteria is resistant to a drug selected from fusidic acid, mupirocin, retapamulin, erythromycin and clindamycin.

The formulation of the invention may be for use to decolonise a subject carrying a Gram-positive bacteria (including any of the Gram-positive bacteria described herein, for example MRSA). Such decolonisation may be effective in preventing or reducing the spread of infection to other subjects particularly in a hospital environment. Decolonisation may also prevent or reduce the risk of surgical site infections resulting from surgical or medical procedures carried out on the patient or at the site of medical devices such as catheters or IV lines or cannula. Accordingly the formulation of the invention may be for use in the decolonisation of a subject prior to carrying out a surgical procedure on the subject, wherein the formulation is applied topically to the subject. Such surgical procedures include, for example elective surgical procedures such as hip or knee replacement. In one embodiment the composition of the invention may be for use in the decolonisation of a subject prior to dialysis. Pre-dialysis decolonisation may prevent or reduce the risk of infection associated with dialysis such as vascular line infection or catheter related bloodstream infections (CRBSI) infections. Decolonisation may be achieved by topically administering the gel composition comprising the halogenated salicylanilide to sites on the subject which are colonised by the Gram-positive bacteria. It is known that a common site for bacterial colonisation such as MRSA is the nose. Accordingly, the formulation of the invention may be applied topically to the nose. Particularly the formulation of the invention may be applied to the anterior nares (the inner surface of the nostrils).

Fungal Infections

In certain embodiments a formulation of the invention is for use in the treatment of a pulmonary fungal infection. Suitably in this embodiment the formulation of the invention is administered by inhalation.

In certain embodiments a formulation of the invention is for use in the treatment of a pulmonary fungal skin infection. Suitably the formulation of the invention is topically applied.

Fungal lung and/or skin infections may be caused by *Candida* sp., *Aspergillus* sp., and/or *Pneumocystis jirovecii*. In some embodiments, the formulations and methods described herein are for treating a fungal infection caused by *Candida albicans, Candida tropicalis, Candida krusei, Candida glabrata, Aspergillus fumigatus, Aspergillus flavus, Aspergillus niger*, and/or *Pneumocystis jirovecii*.

Ocular Disease

Formulations of the invention also find utility in the treatment of one or more clinical signs or symptoms of an ocular disease and condition, including but not limited to ocular infection and inflammatory eye disease (also referred to herein as "inflammatory ocular condition").

In some embodiments, the ocular disease or condition is an inflammatory eye disease, such as dry eye disorder (DED), wherein the one or more clinical signs or symptoms are associated with an abnormal inflammatory response. The topical anti-inflammatory treatment may modulate (such as decreases/downregulates) expression of one or more immune effectors selected from proinflammatory mediators and ocular surface epithelial barrier molecules. The inflammatory ocular condition may be associated with a dysfunction of pre-corneal tear film and/or ocular surface epithelial barrier. The topical anti-inflammatory treatment may modulate (such as decrease/downregulate) expression of one or more immune effectors selected from proinflammatory mediators and ocular surface epithelial barrier molecules in ocular and ocular-associated tissue, such as adnexa, conjunctiva and cornea, and/or in pre-corneal tear film. The topical anti-inflammatory treatment may increase tear production in patients experiencing a dysfunction of pre-corneal tear film associated with an inflammatory ocular disease.

In embodiments, the inflammatory eye disease is selected from dry eye disorder (DED), ocular rosacea, uveitis (e.g. Birdshot retinochoroidopathy), severe conjunctivitis, diabetic retinopathy, multifocal choroiditis with panuveitis, serpiginous choroidopathy, scieritis, an eye inflammation associated with allergy (such as allergic conjunctivitis), and an eye inflammation associated with an autoimmune disorder (e.g. mucous membrane pempigold, eye inflammation associated with infection, retinitis pigmentosa, ankylosing spondylitis, Behcet's syndrome, dermatomyositis, Graves' disease, juvenite rheumatoid arthritis, multiple sclerosis, psoriatic arthritis, blepharitis, Reiter's syndrome, rheumatoid arthritis, Sjogren's syndrome, systemic lupus erythematosus, and Wegener's granulomatosis).

In embodiments, the topical anti-inflammatory treatment provides decreased expression in ocular and ocular-associated tissue (e.g. cornea) and/or in pre-corneal tear film of one or more proinflammatory mediators.

In embodiments, the topical anti-inflammatory treatment provides increased expression in ocular and ocular-associated tissue (e.g. cornea) of one or more ocular surface epithelial barrier molecules.

In embodiments, the one or more clinical signs or symptoms are associated with an abnormal (such as elevated) level of one or more proinflammatory mediators and the topical anti-inflammatory treatment reduces the abnormal level of said one or more proinflammatory mediators in ocular and ocular-associated tissue (e.g. cornea) and/or in pre-corneal tear film.

In embodiments, the one or more clinical signs or symptoms are associated with deficiency in one or more ocular surface epithelial barrier molecules and the topical anti-inflammatory treatment provides increased expression in ocular and ocular-associated tissue (e.g. cornea) of one or more ocular surface epithelial barrier molecules.

In embodiments, the inflammatory eye disease is dry eye disease (DED).

In embodiments, the one or more immune effectors are selected from proinflammatory mediators.

In embodiments, the proinflammatory mediators are selected from proinflammatory cytokines, proinflammatory enzymes, antibacterial proteins and peptides, and immune cells.

In embodiments, the proinflammatory mediators selected from proinflammatory cytokines, proinflammatory enzymes and immune cells.

In embodiments, the ocular surface epithelial barrier molecules are selected from structural ocular surface epithelial barrier proteins (e.g. LOR and FLG) and ocular surface epithelial barrier lipids. Structural ocular surface epithelial barrier proteins, such as LOR and FLG, are expressed by corneal epithelial cells (Tong et al, Invest Ophthalmol Vis Sci, 47(5): 1938-1946, 2006).

In embodiments, the abnormal inflammatory response involves a Th1, Th2, Th17 and/or Th22-type inflammatory response.

In embodiments, the expression in ocular and ocular-associated tissue (e.g. cornea) and/or pre-corneal tear film of said one or more immune effectors are associated with activation of Th1, Th2, Th17 and/or Th22 cells.

In embodiments, expression of said one or more immune effectors is modulated by attenuating one or more responses selected from Th1, Th2, Th17 and Th22-type inflammatory response.

In embodiments, the one or more immune effectors are selected from S100A12, S100A9, PI3, CXCL1, KRT16, MMP12, IL13, CCL17, CCL22, IL8, S100A8, S100A7, IL22, IL17A, IL19, CAMP, DEFB4A/DEFB4B, LOR, IL1B, IL6, IL17C, IL15, IL15RA, FOXP3, FLG, CXCL10, CCL20, CXCL2, IL12B, IL23A, CCL18, IL10, IL5, TSLPR, CD86, CCL19, IL24, ANXA6, SPTLC3, CCR7, CD2, CD28, CD3D, CD3G, CCL2, CCR1, CCR2, IFNGR2, IL12RB2, IL2RA, IRF1, CCR6, IL6R, LCN2, STAT3, IL37, TNFSF4, S100P, SERPINB1, SERPINB4, CCL13, CCR5, IL4R, IL7R, IL1F10, CDSN, CERS3, CLN8, ELOVL3, EREG, FA2H, FAR2, KRT79, PNPLA3, PPL, TJP3, ACER1, ANXA9, CLDN1, CLDN23, DGAT2, DHCR7, FAXDC2, KRT23, KRT77, SCEL, ACOX2 and ACSL1.

In embodiments, the one or more immune effectors are selected from S100A12, S100A9, PI3, CXCL1, S100A7, IL17C, CCL20, CCL18, IL10, SPTLC3, CCL2, CCR1, IFNGR2, CCR6, LCN2, STAT3, TNFSF4, CCL13, IL4R, IL1F10, ELOVL3, FA2H, FAR2, KRT79, PNPLA3, DGAT2, FAXDC2 and ACOX2.

In embodiments, the one or more immune effectors are selected from S100A12, S100A9, PI3, CXCL1, S100A7, IL17C, CCL20, CCL18, IL10, SPTLC3, CCL2, CCR1, IFNGR2, CCR6, LCN2, STAT3, TNFSF4, CCL13, IL4R and IL1F10.

In embodiments, the one or more immune effectors are selected from ELOVL3, FA2H, FAR2, KRT79, PNPLA3, DGAT2, FAXDC2 and ACOX2.

In embodiments, the one or more immune effectors are selected from LOR, FLG, KRT16, ANXA6, SPTLC3, CDSN, CERS3, CLN8, ELOVL3, EREG, FA2H, FAR2, KRT79, PNPLA3, PPL, TJP3, ACER1, ANXA9, CLDN1, CLDN23, DGAT2, DHCR7, FAXDC2, KRT23, KRT77 and SCEL.

In embodiments of the invention, the one or more immune effectors are selected from LOR, FLG, ELOVL3, FA2H, FAR2, KRT79, PNPLA3, DGAT2, FAXDC2 and ACOX2.

In embodiments of the invention, the one or more immune effectors are selected from ELOVL3, FA2H, FAR2, KRT79, PNPLA3, DGAT2, FAXDC2 and ACOX2.

In embodiments, the one or more immune effectors are selected from S100A12, S100A9, PI3, CXCL1, KRT16, MMP12, IL13, CCL17, CCL22, IL8, S100A8, S100A7, IL22, IL17A, IL19, CAMP, DEFB4A/DEFB4B, LOR, IL1B, IL6, IL17C, IL15, IL15RA, FOXP3, FLG, CXCL10, CCL20, CXCL2, IL12B, IL23A, CCL18, IL10, IL5 and TSLPR.

In embodiments, the one or more immune effectors are selected from S100A12, S100A9, S100A7, PI3 and CXCL1.

In embodiments of the invention, the one or more immune effectors are selected from S100A12, S100A9, S100A7, PI3 CXCL1, LOR, FLG, ELOVL3, FA2H, FAR2, KRT79, PNPLA3, DGAT2, FAXDC2 and ACOX2.

In embodiments, the one or more immune effectors are selected from S100A12, S100A9, S100A7, PI3 CXCL1, ELOVL3, FA2H, FAR2, KRT79, PNPLA3, DGAT2, FAXDC2 and ACOX2.

For example, S100A8 and S100A9 are considered biomarkers for dry eye disease (DED) (Enriquez-de-Salamanaca et al, "Molecular and cellular biomarkers in dry eye disease and ocular allergy", Current Opinion in Allergy and Clinical Immunology, 12(5):523-533, 2012).

In some embodiments, the ocular disease is an infectious disease. The infectious disease may be caused by a virus, a bacterium or a fungus. In some embodiments, the infectious ocular disease is selected from the group consisting of conjunctivitis (including bacterial, fungal and viral conjunctivitis), keratitis (including viral, bacterial, fungal and amoebic keratitis), endophthalmitis, blepharitis, sty, uveitis, cellulitis (e.g. bacterial cellulitis), ocular gonorrhoea and ocular herpes.

Viral ocular infections include, but are not limited to, an infection caused by herpes simplex virus (HSV), especially type 1 or type 2 HSV; human herpesvirus 6; adenovirus; molluscum contagiosum virus; varicella-zoster virus; Epstein-Barr virus; cytomegalovirus; picornavirus; hepatitis B virus; mumps virus; measles virus; and influenza virus; for example type 1 or type 2 HSV; most especially type 1 HSV.

Bacterial ocular infections include, but are not limited to, an infection caused by *Neisseria* species, such as *N. gonorrhoeae* and *N. meningitides*; *Staphylococcus* spp. Including *S. aureus, S. epidermidis* and *S. pyogenes*; *Streptococcus* spp, including *S. pneumoniae*; *Haemophilus influenza*; *Moraxella* species including *M. lacunata, M, nonliquefaciens, M. liquefaciens* and *M. catarrhalis*; *Chlamydia trachomatis*; *Pneumococcus* spp.; *Bacteroides* spp.; *Peptostreptococcus* spp.; *Propionibacterium acnes*; *Bacillus cereus*;

*Pseudomonas aeruginosa; Treponema pallidum; Mycobacterium tuberculosis; Mycobacterium leprae*; and *Borrelia burgdorferi*. In some embodiments the ocular infection (e.g. bacterial conjunctivitis) is caused by a bacteria selected from the group consisting of *S. aureus* (including MRSA), *S. pneumoniae, H. influenzae, P. aeruginosa, M. catarrhalis* and *N. gonorrhoeae*.

Fungal ocular infections include, but are not limited to, infections caused by *Candida* spp. including *C. albicans, C. famata, C. parapsilosis, C. lipolytica, C. humicola, C. guilliermondii* and *C. glabrata*; *Aspergillus* spp. including *A. flavus, A. niger, A. fumigatus, A. terreus, A. glaucus,* and *A. nidulans*; *Fusarium* spp. including *F. solani* and *F. moniliforme*; *Cryptococcus* spp. including *C. neoformans*; *Pneumocystis* spp. including *P. carinii*; *Histoplasma* spp. including *H. capsulatum*; *Bipolaris* spp.; *Zygomycetes* spp.; *Coccidioides immitis*; *Blastomyces dermatitidis*; *Lasiodiplodia theobromae*; *Alternaria* spp.; *Sporothrix schenckii*; *Paecilomyces lilacinus*; *Acremonium kiliense*; *Exophiala jeanselrnei*; *Pseudallescheria boydii*; *Scytalidium dimidiatum*; *Helminthosporium* spp.; *Penicillium chrysogenum*; *Absydia* spp.; *Rhizopus* spp.; *Curvularia* spp.; *Phialophora* spp.; *Paracoccidioides brasiliensis*; *Malassezia* spp. including *M. furfur* and *M. pachydermatis*; *Conidiobolus coronatus*; *Rhodotorula* spp.; *Drechslera* spp.; *Curvularia* spp.; *Mucor* spp,; and *Absidia* spp.

In some embodiments, the formulation is topically administered in the form an ophthalmic composition, such as an ophthalmic cream, ointment, gel, paste, lotion, foam, suspension or solution.

Inflammatory Disease

In certain embodiments the inflammatory disease is a pulmonary inflammatory disease. Pulmonary inflammatory diseases include, but are not limited to, pulmonary inflammatory disease is selected from the group consisting of: asthma, chronic obstructive pulmonary disease (COPD), pulmonary fibrosis, pneumonia, interstitial lung disease, sarcoidosis, bronchiolitis obliterans, pneumonitis, acute respiratory distress syndrome (ARDS), bronchiectasis, cystic fibrosis, idiopathic pulmonary fibrosis, radiation induced fibrosis, silicosis, asbestos induced pulmonary or pleural fibrosis, acute lung injury, usual interstitial pneumonia (UIP), Chronic lymphocytic leukemia (CLL)-associated fibrosis, Hamman-Rich syndrome, Caplan syndrome, coal worker's pneumoconiosis, cryptogenic fibrosing alveolitis, obliterative bronchiolitis, chronic bronchitis, emphysema, Wegner's granulamatosis, lung scleroderma, silicosis, asbestos induced pulmonary and/or pleural fibrosis.

The term "pulmonary fibrosis", includes all interstitial lung disease associated with fibrosis. In some embodiments, pulmonary fibrosis includes the term "idiopathic pulmonary fibrosis" or "IPF". In some embodiments, pulmonary fibrosis, by non-limiting example, may result from inhalation of inorganic and organic dusts, gases, fumes and vapours, use of medications, exposure to radiation or radiation therapy, and development of disorders such as hypersensitivity pneumonitis, coal worker's pneumoconiosis, chemotherapy, transplant rejection, silicosis, byssinosis and genetic factors. Exemplary pulmonary inflammatory diseases for the treatment or prevention using the formulations and methods described herein include, but are not limited, idiopathic pulmonary fibrosis, pulmonary fibrosis secondary to systemic inflammatory disease such as rheumatoid arthritis, scleroderma, lupus, cryptogenic fibrosing alveolitis, radiation induced fibrosis, chronic obstructive pulmonary disease (COPD), sarcoidosis, scleroderma, chronic asthma, silicosis, asbestos induced pulmonary or pleural fibrosis, acute lung injury and acute respiratory distress (including bacterial pneumonia induced, trauma induced, viral pneumonia induced, ventilator induced, non-pulmonary sepsis induced, and aspiration induced). In some embodiments the formulations and methods of the invention may be for use in the treatment or prevention of secondary bacterial or viral infections associated with a pulmonary inflammatory disease (e.g. a secondary bacterial infection associated with COPD).

In some embodiments, the formulations and methods described herein are used to treat or slow down the progression of or prevent asthma. Asthma may be associated with or caused by environmental and genetic factors. Asthma is a common chronic inflammatory disease of the airways characterized by variable and recurring symptoms, reversible airflow obstruction, and bronchospasm. Symptoms include wheezing, coughing, chest tightness, and shortness of breath. Non-limiting examples of asthma include, but are not limited to, allergic asthma, non-allergic asthma, acute severe asthma, chronic asthma, clinical asthma, nocturnal asthma, allergen-induced asthma, aspirin-sensitive asthma, exercise-induced asthma, child-onset asthma, adult-onset asthma, cough-variant asthma, occupational asthma, steroid-resistant asthma, or seasonal asthma.

In some embodiments, the formulations and methods described herein can treat or slow down the progression of or prevent lung inflammation. Lung inflammation may be associated with or contribute to the symptoms of bronchitis, asthma, lung fibrosis, chronic obstructive pulmonary disorder (COPD), and pneumonitis. The halogenated salicylanilide niclosamide has been shown to reduce mucus production and secretion, as well as bronchoconstriction, in a mouse model of asthma. In addition, niclosamide was found to be a potent inhibitor of the $Cl^-$ channels TMEM16A and TMEM 116F, which contribute to the release of mucus and inflammatory mediators. Niclosamide may therefore be suitable for the treatment of inflammatory airway diseases such as cystic fibrosis, asthma and COPD (Cabrita et al., JCI Insight 2019:4(15):e128414).

In some embodiments, the formulations and methods described herein are used to treat or prevent clinical signs and symptoms of, or infections associated with, cystic fibrosis. Cystic fibrosis (CF) is a genetic disorder that affects mostly the lungs, and involves frequent bacterial infections. Approximately 85% of CF patients have chronic, recurrent *P. aeruginosa* infection, which significantly contributes to lung function decline and mortality. Long-term issues include difficulty breathing and coughing up mucus as a result of these frequent lung infections. Thus, in some embodiments, the formulations and methods are used to treat a bacterial infection, such as a *P. aeruginosa* infection, associated with cystic fibrosis. In some embodiments, the formulations and methods are used to treat a bacterial infection associated with cystic fibrosis, wherein the bacterial infection is caused by or associated with a Gram-positive bacteria (e.g. bacteria selected from *S. aureus, S. pneumoniae, H. influenzae, M. catarrhalis* and *S. pyogenes*).

In preferred embodiments the pulmonary inflammatory disease is treated by inhaling a formulation of the invention (e.g. by inhalation of an aerosol of a formulation of the invention).

Inflammatory Skin Diseases

In some embodiments, the formulations and methods described herein can treat or slow down the progression of or prevent an inflammatory skin disease. Preferably in these embodiments the formulation of the invention is topically applied to the subject. For example the formulation of the invention may be topically applied in the form of a spray, lotion, cream, foam, or droplets. Suitably the formulation of the invention is topically applied to the skin at a site affected by the inflammatory skin disease, for example by topically applying the formulation directly to an atopic dermatitis lesion.

In certain embodiments the inflammatory skin disease is selected from: psoriasis, dermatitis (e.g. atopic dermatitis), scleroderma, disorders of hair follicles and sebaceous glands, acne, rosacea, rhinophyma, cutaneous lupus, inflammatory reactions (for example drug eruptions, erythema multiforme, erythema nodosum, and granuloma annulare), inflammation associated with fungal or yeast infections (e.g. dermatophytosis), urticaria, dermatitis herpetiformis, lichen planus, hidradenitis suppurativa, pitayriasis rosea, chronic sinusitis, chronic rhinosinusitis, lupus, vitiligo and keratosis pilaris.

In certain embodiments, the inflammatory skin condition is dermatitis, for example atopic dermatitis.

In certain embodiments the inflammatory skin condition is a dermatitis (or eczema) selected from contact dermatitis, allergic contact dermatitis, irritant contact dermatitis, atopic dermatitis, seborrhoeic dermatitis, actinic dermatitis, hand and foot dermatitis, pompholyx dermatitis, lichen simplex chronicus (neurodermatitis), exfoliative dermatitis (erythroderma), asteatotic dermatitis, carcinomatous dermatitis, nummular dermatitis, neonatal dermatitis, paediatric dermatitis, diaper dermatitis, stasis dermatitis, perioral dermatitis, dermatomyositis, eczematous dermatitis, photoallergic dermatitis, phototoxic dermatitis, phytophotodermatitis and radiation-induced dermatitis.

In certain embodiments the formulation of the invention is for use in the treatment of prevention of one or more symptoms of dermatitis, for example a symptom selected from erythema, excoriation, lichenification, edema, papulation and dryness, particularly erythema, lichenification, edema and papulation.

Nasal and Sinus Conditions

In some embodiments the formulation of the invention is for use in the treatment or prevention of rhinitis, rhinosinusitis or inflammation of nasal tissues and sinuses. Suitably the formulation of the invention is applied intranasally, for example in the form of a spray, droplets, powder or an aerosol.

In some embodiments the formulation of the invention is for use in the treatment or prevention of rhinitis. Thus it may be that the rhinitis is chronic rhinitis. It may be that the rhinitis is acute rhinitis.

In some embodiments the formulation of the invention is for use in the treatment or prevention of rhinosinusitis. Thus it may be that the rhinosinusitis is chronic rhinosinusitis. It may be that the rhinosinusitis is acute rhinosinusitis.

Otitis and Ear Infections

In some embodiments the formulation of the invention is for use in the treatment or prevention of otitis. In some embodiments the otitis is otitis externa. In some embodiments the otitis is otitis media. The otitis may be a chronic otitis. The otitis may be acute otitis.

In certain embodiments the otitis is caused by or associated with a bacterial infection, for example a Gram-positive bacterial infection.

It may be that the otitis is treated by topically applying the formulation of the invention. For example topical application in the form of droplet, a liquid or spray.

Anti-Inflammatory Effects

In some embodiments the formulation of the invention reduces the abnormal level of one or more proinflammatory mediators associated with an inflammatory disease (e.g. an of the inflammatory diseases and conditions described herein (e.g. a pulmonary inflammatory disease described herein). For example, by attenuating one or more responses selected from Th1, Th2, Th17 and Th22-type inflammatory response. The formulations of the invention may attenuate one or more of the proinflammatory mediators disclosed above in relation to the treatment of inflammatory ocular disease.

In some embodiments the formulation of the invention reduces one or more of CRP, leukocytes, IL1B, IL-6, IL-10, IL-2, IFNγ, IP10, MCP1, GCSF, IP10, MCP1, MIP1A, and/or TNFα associated with an inflammatory disease disclosed herein (e.g. an pulmonary inflammatory disease).

Scalp Conditions

The scalp is prone to a number of inflammatory, bacterial and/or fungal infections. However, the presence of hair can make the topical treatment of scalp conditions difficult, because the hair can inhibit access of the topical treatment to the scalp. The liquid formulations of the invention may be particularly suitable for the topical treatment of scalp conditions.

Accordingly there is provided a liquid formulation of the invention for use in the topical treatment or prevention of an inflammatory, fungal or bacterial scalp condition. In certain embodiments the scalp condition is selected from: seborrhoeic dermatitis (dandruff), tinea capitis, psoriasis of the scalp, pruritis of the scaly, erythema of the scalp, contact dermatitis of the scalp, lichen planus, discoid lupus erythematosus, alopecia areata and folliculitis.

Dosage and Dosage Regimens

The dosage and dosing regimen of the formulation of the invention will depend upon a number of factors that may readily be determined by a physician, for example the severity of the viral infection, the responsiveness to initial treatment, the mode of administration and the particular infection being treated. Examples of suitable doses, dosing volumes and frequencies are set out in the brief summary of the disclosure above.

Suitable modes of administration include oral, intranasal, parenteral (e.g. intravenous, intramuscular, intra-arterial, subcutaneous or intradermal), topical, inhalation (intraorally or intranasally), or a combination thereof.

The total daily dose of the halogenated salicylanilide administered to the subject may comprise one or more unit doses. The total daily dose may be from 5 to 1000 mg, from 6 to 800 mg, from 8 to 700 mg, from 10 to 500 mg, from 15 to 400 mg, from 30 to 300 mg, from 50 to 250 mg, from 100 to 200 mg or from 120 to 250 mg of the halogenated salicylanilide or salt thereof.

In some embodiments the total daily dose is from 1 to 50 mg, from 1.5 to 40 mg, from 2 to 30 mg, from 2.5 to 20 mg, from 3 to 15 mg, from 3.5 to 12 mg, from 4 to 10 mg, from 4.5 to 9 mg, from 5 to 8.5 mg, from 5.5 to 8 mg, from 6 to 7.5 mg or from 6.5 to 7 mg of the halogenated salicylanilide or salt thereof (e.g. niclosamide or niclosamide ethanolamine). In some embodiments the total daily dose is 5.6 mg niclosamide ethanolamine, corresponding to 4.7 mg niclosamide free base.

When the formulation of the invention is administered to the subject using an inhaler (e.g. a nebulizer) not all of the dose loaded into the inhaler will reach the lungs because, for example some drug will be entrained in the device, some of the drug may not enter the mouth or nose of the subject and some mat become entrained in the oral or nasal cavity and not penetrate into the airways (e.g. the lung). Reference to the doses of the inhalable compositions described herein refer to the dose of halogenated salicylanilide (e.g. niclosamide) or pharmaceutically acceptable salt thereof which is loaded into the inhaler, or is metered by the inhaler before the inhaler is actuated. The dose inhaled by the subject may be for example 10%, 15%, 20% or 25% lower that the pre-actuation dose.

The dose may be delivered to the subject via multiple modes of administration. In some embodiments, a first dose may be administered intranasally (e.g. using a nasal spray device) and a second dose may be administered intraorally (e.g. using a nebulizer). It will be appreciated that the first dose may be administered after the second dose, or vice versa. For example, in embodiments wherein the formulation is in the form of a solution, a volume of from 50 to 250 µl, or from 100 to 200 µl (e.g. 130-150 µl) per nostril may be administered intranasally, and a volume of from 1 to 10 ml, from 2 to 8 ml or from 3 to 7 ml (e.g. 4-6 ml) may be administered intraorally (e.g. via a nebulizer).

The formulation may be administered once per day, or multiple times (e.g. 2, 3 or 4 times) per day. In some embodiments the formulation is administered twice daily.

The total daily volume administered to the subject may be from 200 µl to 20 ml, from 300 µl to 19 ml, from 500 µl to 18 ml, from 1 ml to 17 ml, from 2 ml to 16 ml, from 3 to 15 ml, from 4 to 14 ml, from 5 ml to 12 ml or from 8 ml to 10 ml of a solution of the invention. In some embodiments, the formulation is a solution containing from 0.1 to 5%, from 0.5 to 5%, from 1 to 4%, from 1.5 to 3% (e.g. from about 1 to 2%) of the halogenated salicylanilide, or a pharmaceutically acceptable salt thereof.

The formulation may be administered to the subject over a number of consecutive days or weeks. For example, the formulation may be administered one or more times daily over a period of from 3 days to 6 weeks, from 7 days to 4 weeks from 10 days to 3 weeks or from 14 to 18 days. In some embodiments, the formulation is administered to the subject twice daily for up to 10, 14 or 28 days. It will be appreciated that the dosing period will be determined by the type and severity of the disease being treated, or whether the formulation is being administered prophylactically. For example, for the treatment of chronic conditions (e.g. COPD, asthma, and infections associated with cystic fibrosis), or moderate or severe cases of COVID-19, the treatment duration may be longer (e.g. at least 4 weeks, at least 6 weeks, at least 8 weeks or at least 12 weeks). It may be that treatment is continued until the subject has recovered.

In some embodiments, the subject is intranasally administered 100-200 µl (e.g. 120-180 µl or 130-160 µl) per nostril of a 1% solution of niclosamide ethanolamine, twice per day. In a preferred embodiment, the subject is intranasally administered 140 µl per nostril of a 1% solution of niclosamide ethanolamine, twice per day. Additionally, or alternatively, the subject may be administered from 1 to 10 ml, from 2 to 8 ml, from 3 to 6 ml or from 4 to 5 ml of a nebulised solution of 1% niclosamide ethanolamine, twice per day.

It will be appreciated that the dose of the formulation and/or the dosage regime may be selected by the skilled person depending on a number of factors such as, but not limited to, the severity of the disease, the age of the subject and/or the presence of any underlying conditions.

In some embodiments, the formulation is administered to a subject for the treatment or prophylaxis of COVID-19. In some embodiments wherein the subject is suffering from mild COVID-19, the subject is asymptomatic, or the subject is being treated prophylactically (e.g. a subject in a high-risk group, or a close contact of an infected individual), the formulation may be administered one or more times daily for a period of no more than 21 days, no more than 18 days, no more than 16 days, no more than 14 days, no more than 12 days or no more than 10 days. In some embodiments wherein the subject is suffering from moderate or severe COVID-19, the formulation may be administered one or more times daily for a period of at least 7 days, at least 10 days, at least 14 days, at least 21 days or at least 28 days.

As will be appreciated the doses and dosage regimens set out in this section may be used with any of the formulations of the invention. In a preferred embodiment the formulation of the invention used in any of the doses and dosage regimens described herein and in this "dosage and dosage regimens" is a liquid formulation comprising:

about 1% niclosamide ethanolamine;
about 15% cyclodextrin, preferably a β-cyclodextrin, more preferably HP-β-CD;
about 2% PVP (e.g. PVP 30);
the balance being water,
wherein the percentages are by weight based on the weight of the liquid formulation; and optionally wherein the formulation has a pH of from 7.0 to 8.5, for example from 7.5 to 7.8, or from 7.6 to 8.0, preferably about 7.8.

Combination Therapies

The formulation of the invention may be used alone to provide a therapeutic effect. The formulation of the invention may also be used in combination with one or more additional therapeutic agents.

In some embodiments the additional therapeutic agent is selected from one or more of:
- an antiviral agent (e.g. remdesivir, a HIV protease inhibitor (e.g. lopinavir or ritonavir), or a 3CL protease inhibitor (e.g. PF-07304814);
- a vaccine (e.g. a COVID-19 vaccine), examples of vaccines include weakened or inactivated viral vaccines, replicating or non-replicating viral vector vaccines, nucleic acid vaccines (RNA or DNA vaccines), protein subunit vaccines or virus-like particle vaccines;
- bronchodilators, e.g. short acting beta agonists (e.g. albuterol, epinephrine or levalbuterol), or long acting beta agonists (e.g. formoterol, salmeterol or vilanterol);
- anticholinergics (e.g. ipratropium);

leukotriene modifiers (e.g. montelukast, zafirlukast, or zileuton);

long-acting bronchodilators (e.g. tiotropium);

anti-inflammatory agents (e.g. steroids, which may be intavennous, oral or inhaled steroids (e.g. dexamethasone, budesonide); non-steroidal anti-inflammatory agents (e.g. ibuprofen, naproxen, ketoprofen or carprofen, a COX-2 inhibitor such as celecoxib), an anti-inflammatory antibody (e.g. benralizumab, dupilumab, mepolizumab, omalizumab, reslizumab);

an antibacterial agent, for example a Gram-positive or Gram negative antibiotic;

an anti-viral antibody (e.g antibodies that act against the spike proteins of a corona virus such as SARS-CoV-2 (e.g. LY-CoV555, LY-CoV016, AZD7442, REGN10933, or REGN10987); and antibodies from subjects that have previously been infected with a virus (e.g. convalescent plasma therapies);

or a combination of any two or more thereof.

Such combination treatment may be achieved by way of the simultaneous, sequential or separate dosing of the individual components of the treatment. Such combination products employ the formulation of this invention within a therapeutically effective dosage range described hereinbefore and the other pharmaceutically-active agent within its approved dosage range.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

In some embodiments in which a combination treatment is used, the amount of the formulation of the invention and the amount of the other pharmaceutically active agent(s) are, when combined, therapeutically effective to treat a targeted disorder in the patient. In this context, the combined amounts are "therapeutically effective amount" if they are, when combined, sufficient to reduce or completely alleviate symptoms or other detrimental effects of the disorder; cure the disorder; reverse, completely stop, or slow the progress of the disorder; or reduce the risk of the disorder getting worse. Typically, such amounts may be determined by one skilled in the art by, for example, starting with the dosage range described in this specification for the halogenated salicylanilide (e.g. niclosamide or pharmaceutically acceptable salt thereof) present in the formulation of the invention and an approved or otherwise published dosage range(s) of the other pharmaceutically active agent(s).

Preparation of Formulations

Formulations according to the invention may be prepared by the following method:
adding cyclodextrin and/or a halogenated salicylanilide (e.g. niclosamide), or a pharmaceutically acceptable salt thereof, to a solvent to form a suspension;
heating the suspension for a period of time sufficient for the cyclodextrin and/or the a halogenated salicylanilide, or a pharmaceutically acceptable salt thereof, to dissolve in the solvent, thereby forming a solution;
cooling the solution.

In some embodiments, the method comprises adding both the cyclodextrin and the a halogenated salicylanilide, or a pharmaceutically acceptable salt thereof, to the solvent prior to heating.

In some embodiments, the method comprises:
adding one of a cyclodextrin and a halogenated salicylanilide, or a pharmaceutically acceptable salt thereof, to the solvent to form a suspension;
heating (or continuing to heat) the suspension for a period of time sufficient for the cyclodextrin or niclosamide, or a pharmaceutically acceptable salt thereof, to dissolve in the solvent, thereby forming a first solution;
adding the other of the cyclodextrin and the halogenated salicylanilide, or a pharmaceutically acceptable salt thereof, to the first solution in the form of a solid;
heating (or continuing to heat) the first solution for a period of time sufficient for the solid to dissolve, thereby forming a second solution; and
cooling the solution.

In some embodiments, the method comprises:
adding a cyclodextrin to a solvent to form a first suspension, and heating the first suspension for a period of time sufficient for the cyclodextrin to dissolve in the solvent, thereby forming a first solution;
adding a halogenated salicylanilide (e.g. niclosamide), or a pharmaceutically acceptable salt thereof, to a solvent to form a second suspension, and heating the second suspension to a temperature for a period of time sufficient for the halogenated salicylanilide, or a pharmaceutically acceptable salt thereof, to dissolve in the solvent, thereby forming a second solution;
adding the first solution to the second solution to form a mixture; and
cooling the mixture.

The method may comprises heating (or continuing to heat) the mixture, after adding the first solution to the second solution, prior to cooling.

The cyclodextrin and/or the halogenated salicylanilide may be added in the form of a solid (e.g. a powder), a dispersion, a suspension or a slurry.

In some embodiments, heating is carried out to a temperature of 120° C. or less, for example from 50 to 120° C., from 60 to 95 or from 70 to 80° C., e.g. about 65° C.

The solvent may be pre-heated prior to addition of the cyclodextrin and/or the halogenated salicylanilide. Thus, in some embodiments, "heating the suspension" will be understood as meaning that the temperature of the solvent/suspension is maintained after addition of the cyclodextrin and/or the halogenated salicylanilide.

In some embodiments, cooling is carried out to a temperature of from 10 to 40° C.

In some embodiments, the cyclodextrin and/or the halogenated salicylanilide is mixed with the solvent prior to and/or during the heating step. Mixing may be carried out by any suitable means, for example by stirring, shaking, rotating or by using a vortex mixer.

Mixing may be carried out for a period of from 30 seconds to 1 hour, from 1 minute to 30 minutes, or from 5 to 20 minutes, in total.

In some embodiments, the method further comprises sonicating the mixture of the cyclodextrin and/or a halogenated salicylanilide with the solvent. Sonication (e.g. ultrasonication) may be carried out prior to and/or after the mixing step.

For example, following addition of the cyclodextrin and/or a halogenated salicylanilide to the solvent to form a suspension, the suspension may be mixed by vortexing for 1-10 minutes. Optionally, the mixture is then sonicated while heating (e.g. at 65° C.). optionally, the mixture is then mixed by vortexing for a further 1-5 minutes. Optionally, Optionally, the mixture is then sonicated again while heating (e.g. at 65° C.). A final mixing step by vortexing may then be carried out for 30 seconds to 2 minutes.

In some embodiments, the method comprises raising the pH of the solvent, solution or suspension to a pH of about 7 or more. For example, the pH may be raised to a pH of 8 or more, e.g. a pH of 8-13, 9-12 or 10-11, e.g. pH 8-9.5. The pH of may be raised by the addition of a base, such as sodium hydroxide. The base may be added prior to, during or after mixing. The base may be added before or after addition of the halogenated salicylanilide, the cyclodextrin and/or the polymer.

In some embodiments the method comprises raising the pH to a pH of 7 or greater prior to the addition of the halogenated salicylanilide. For example raising the pH to 8 or greater.

In some embodiments, the method comprises lowering the pH of the solution to a pH of 4-8. The pH may be lowered by the addition of an acid, such as hydrochloric acid. The pH may be lowered after mixing and/or sonication is complete, i.e. when all of the solids are dissolved and the formulation is clear without any visible particles. The solution may be further mixed following addition of the acid, for example by vortexing for 1 minute.

In some embodiments the method comprises lowering the pH of the solution to a pH of 4-8 after the halogenated salicylanilide has dissolved in the solvent. In some embodiments, the pH is lowered after both the halogenated salicylanilide and the cyclodextrin have dissolved in the solvent.

In some embodiments, the method comprises adjusting the pH of the solution to a pH of 7-8, e.g. 7.5-7.8. The pH may be adjusted after cooling the solution. The pH may be adjusted by the addition of a base (e.g. NaOH) or an acid (e.g. HCl) as appropriate.

In some embodiments, the solvent is or comprises water. The solvent may further comprise a co-solvent, such as DMSO. The co-solvent may be added prior to or after any or all of the components of the formulation. For example, in some embodiments, the co-solvent is added during or after cooling.

In some embodiments, the method further comprises adding one or more polymers. The polymer may be any of the polymers described herein in relation to the formulation of the invention, preferably a water-soluble polymer, more preferably a PVP. The polymer may be added to the solvent before, after, or at the same time as the cyclodextrin and/or the halogenated salicylanilide. For example, in some embodiments, all of the dry components (i.e. the cyclodextrin, the halogenated salicylanilide (e.g. niclosamide), or salt thereof, and the polymer may be combined prior to adding to the solvent. Alternatively, each component may be added to the solvent separately and dissolved before adding the next component.

In some embodiments, the method comprises adding the polymer after the cyclodextrin and the halogenated salicylanilide have been dissolved in the solvent. In some embodiments, the polymer is added after the pH of the solution has been lowered to a pH of 4-8.

In some embodiments, the method further comprises the addition of one or more additional components to the solvent, such as one or more electrolytes, stabilisers, or preservatives.

In some embodiments, the method comprises:
adding a cyclodextrin (e.g. HP-β-CD), a halogenated salicylanilide (e.g. niclosamide), or a pharmaceutically acceptable salt thereof, and, optionally, a polymer (e.g. PVP) to a solvent comprising water and a co-solvent (e.g. DMSO) to form a suspension;
raising the pH of the suspension to a pH of 7-8 by adding a base (e.g. NaOH);
mixing the suspension;
heating the suspension to a temperature of less than 120° C. (e.g. 65° C.) for a period of time sufficient for the cyclodextrin, the halogenated salicylanilide, or a pharmaceutically acceptable salt thereof, and the polymer (if present) to dissolve in the solvent, thereby forming a solution;
lowering the pH of the solution to a pH of 4-8 by adding an acid (e.g. HCl);
cooling the solution (e.g. to room temperature);
adjusting the pH of the solution to a pH of 7-8.

In some embodiments, the method comprises:
optionally, pre-heating a solvent (e.g. water) to a desired temperature, such as 65-90° C.;
adding cyclodextrin to the solvent to form a first suspension;
heating the first suspension, or maintaining the temperature of the first suspension at the desired temperature, while mixing for a period of time sufficient for the cyclodextrin to dissolve in the solvent, thereby forming a first solution;
adding a polymer (e.g. PVP) to the first solution;
raising the pH of the first solution (e.g. to a pH of 9-10);
adding a halogenated salicylanilide (e.g. niclosamide), or a pharmaceutically acceptable salt thereof, to the first solution, to form a second suspension, optionally wherein the halogenated salicylanilide (e.g. niclosamide), or a pharmaceutically acceptable salt thereof, is added in the form of a slurry;
maintaining the temperature of the second suspension at the desired temperature, while mixing for a period of time sufficient for the halogenated salicylanilide (e.g. niclosamide), or a pharmaceutically acceptable salt thereof, to dissolve, thereby forming a second solution;
cooling the second solution (e.g. to a temperature of about 20 to about 30° C.)
optionally, adding a co-solvent (e.g. DMSO) to the second solution, during or after cooling; and
adjusting the pH of the second solution, e.g. to a pH of about 7.5 to about 8.5.

In some embodiments, the method comprises:
optionally, pre-heating a solvent (e.g. water) to a desired temperature, such as 65-90° C.;
adding cyclodextrin and a base to the solvent to form a first suspension;
heating the first suspension, or maintaining the temperature of the first suspension at the desired temperature, while mixing for a period of time sufficient for the cyclodextrin to dissolve in the solvent, thereby forming a first solution having a pH of at least 8;
adding a halogenated salicylanilide (e.g. niclosamide), or a pharmaceutically acceptable salt thereof, to the first solution, to form a second suspension, optionally wherein the halogenated salicylanilide (e.g. niclosamide), or a pharmaceutically acceptable salt thereof, is added in the form of a slurry;
maintaining the temperature of the second suspension at the desired temperature, while mixing for a period of time sufficient for the halogenated salicylanilide (e.g.

niclosamide), or a pharmaceutically acceptable salt thereof, to dissolve, thereby forming a second solution;

lowering the pH of the second solution to a pH of from 4 to 8 (e.g. by addition of an acid);

adding a polymer (e.g. PVP) to the second solution, and mixing for a period of time sufficient for the polymer to dissolve in the second solution;

cooling the second solution (e.g. to a temperature of about 20 to about 30° C.);

adjusting the pH of the second solution, e.g. to a pH of about 7.5 to about 8.5.

Optionally, the solution with the cyclodextrin and halogenated salicylanilide dissolved therein (e.g. the second solution) may be diluted (e.g. with the solvent, such as water) to achieve the desired concentration of halogenated salicylanilide. The solution may then be discharged into a suitable container for storage or administration.

The formulation may be prepared in any suitable reaction vessel. Conveniently, the vessel may be jacketed (e.g. with a water jacket) to maintain the temperature of the vessel during preparation of the formulation.

In some embodiments, the method further comprises forming a solid, e.g. a powder, from the solution. Solids may be prepared using well-known methods, for example by micro-precipitation, lyophilisation or spray drying, or spray-freeze drying the solution.

EXAMPLES

The invention is further illustrated by the following examples.

| Abbreviations | |
| --- | --- |
| CD | Cyclodextrin |
| DMSO | Dimethylsulfoxide |
| NEN | Niclosamide ethanolamine |
| OXY | Oxyclozanide |
| PVP | Polyvinyl pyrrolidone |

Example 1: Aqueous Formulation Comprising Niclosamide Ethanolamine

The formulation shown in Table 1 was prepared as described below:

TABLE 1

| Component (trade name) | Composition Formulation A % (w/v) |
| --- | --- |
| Niclosamide ethanolamine | 1.0 |
| Polyvinylpyrrolidone (PVP K30) | 2.0 |
| Hydroxypropyl Beta-cyclodextrin (Kleptose ® HPB) | 15.0 |
| DMSO | 1.0 |
| 1M NaOH/HCL | As required to adjust pH to 7.8 |
| Water (milliQ) | q.s. |

Niclosamide ethanolamine (100 mg), PVP K30 (200 mg) and hydroxypropyl beta-cyclodextrin (1500 mg) were weighed into a 20 mL glass vial.

To this powder mixture was added milliQ water (8.5 mL), 2 drops 5M NaOH, and 100 μL DMSO. The pH of the mixture was at least 8

The vial was placed in an ultrasonic bath at 65° C. and mixed according to the following schedule:

vortex for 1 to 10 minutes; ultrasonication at 65° C.; vortex for 1 to 5 minutes; ultrasonication at 65° C.; and vortex 1 min;

to provide a clear red composition without any visible particles.

2 drops 5M HCl were added to the composition followed by vortexing for 1 minute. The resulting formulation was cooled to room temperature and the pH adjusted to 7.80±0.1 using 1 M NaOH/HCl to give the title formulation. The Osmolarity of the title composition was 180 mOsm/kg.

Formulations B to E shown in Table 2 were prepared using an analogous method

TABLE 2

| Component (trade name) | Composition | | | |
| --- | --- | --- | --- | --- |
| | B % (w/v) | C % (w/v) | D % (w/v) | E % (w/v) |
| Niclosamide ethanolamine | 1 | 1 | 1 | 2 |
| Polyvinylpyrrolidone (PVP K30) | — | 2 | 2 | 2 |
| Polyvinylpyrrolidone (PVP K17) | 2 | — | — | — |
| Hydroxypropyl Beta-cyclodextrin (Kleptose ® HPB) | 15 | 15 | 50 | 50 |
| DMSO | — | — | — | — |
| 1M NaOH/HCL | As required to adjust pH to 7.5-7.8 | As required to adjust pH to 7.5-7.8 | As required to adjust pH to 7.5-7.8 | As required to adjust pH to 7.5-7.8 |
| Water (milliQ) | q.s. | q.s. | q.s. | q.s. |

Example 2: Aqueous Formulation Comprising Oxyclozanide

The formulations shown in Table 3 was prepared using an analogous method to that described in Example 1:

TABLE 3

| Component (trade name) | Composition | |
| --- | --- | --- |
| | Formulation F % (w/v) | Formulation G % (w/v) |
| Oxyclozanide | 1 | 1 |
| Polyvinylpyrrolidone (PVP K30) | 2 | 2 |
| Hydroxypropyl Beta-cyclodextrin (Kleptose ® HPB) | 15 | 50 |
| DMSO | 1 | — |
| 1M NaOH/HCL | As required to adjust pH to 7.5-7.8 | As required to adjust pH to 7.5-7.8 |
| Water (milliQ) | q.s. | q.s. |

Example 3: Storage Stability of Aqueous Niclosamide Ethanolamine Formulations A sample of Formulation A described in Example 1 was stored under refrigerated conditions at 5° C. in darkness. Another sample was stored at room temperature exposed to ambient light. After 74 days storage both samples were analysed for degradation of the niclosamide using the following HPLC-UV method:

Column: Kinetex C18 100 Å LC column (4.6×100 mm, 5 µm) from Phenomenex
Mobile phase A: 0.1 M acetate buffer adjusted to pH 4.0
Mobile phase B: methanol
Injection volume: 5 µL
Flow rate: 1.0 mL/min
Detection wavelength: 310 nm
Measurement time: 10 min

| Time | % A | % B |
|------|-----|-----|
| 0.00 | 70  | 30  |
| 5.00 | 20  | 80  |
| 7.50 | 20  | 80  |
| 7.60 | 70  | 30  |

Results

The sample stored under refrigerated conditions in darkness showed 0.6% degradation of niclosamide. The sample stored at room temperature showed 0.7% degradation of niclosamide.

Example 4: Antibacterial Effects of Niclosamide Against Bacteria Associated with Pulmonary Bacterial Infections Such as Pneumonia Microorganisms Bacterial strains were chosen for their relevance regarding lung infections, such as pneumonia: *Staphylococcus aureus*, methicillin-resistant *Staphylococcus aureus* (MRSA), *Streptococcus pneumoniae*, *Haemophilus influenzae*, *Moraxella catarrhalis* and *Streptococcus pyogenes*. *S. aureus* and *S. pyogenes* strains are as defined in WO 2016/038035.

Strains were conserved in Luria Bertani (LB) Broth (*S. aureus*) or Brain Heart Infusion (BHI) (*S. pyogenes*) supplemented with glycerol 15% (v/v) at −80° C., and reactivated by isolation on LB (*S. aureus*) or BHI (*S. pyogenes*) agar plates. Strains were cultivated in Mueller Hinton (MH) Broth-cation adjusted (*S. aureus*) or BHI (*S. pyogenes*). All strains were cultivated aerobically (microaerobically for *S. pyogenes* strains) at 37° C.

The following tests were performed to assess the antibacterial activity of niclosamide in vitro:

Minimum Inhibitory Concentration (MIC) Assay

The MIC was determined according to the method described in WO 2016/038035.

Results

TABLE 4

MIC values in µg/mL for niclosamide using the above described assay.

| Species | MIC (µg/mL) |
|---------|-------------|
| Multi-drug resistant strains of *S. aureus* (including MRSA) (226 isolates) | 0.06-0.5 |
| *S. pneumoniae* | 0.25 |
| *H. influenzae* | 0.5 |
| *M. catarrhalis* | 0.12 |
| *S. pyogenes* | 0.125 |

The MIC of niclosamide was ≤0.5 µg/mL against all targeted strains.

The results in Table 4 show that niclosamide is effective against a range of bacteria, including bacteria commonly associated with lung infections. Accordingly, the inhalable compositions comprising niclosamide may be effective in the treatment or prevention of bacterial lung infections, including secondary bacterial lung infections associated with cystic fibrosis, COPD and respiratory viral infections.

Example 5: Antibacterial Effects of Cyclodextrin Formulations Comprising Niclosamide or Oxyclozanide Approximately five to ten colonies of the strains ATCC 29213 (A), MRSA 434844 (B) and *S. aureus* Newman (C) were picked from a LB agar plate, suspended in PBS and set to an OD600 of ~0.1. 10 µL of each bacterial suspension were pipetted on a LB agar plate and dried at RT. 10 µL of each formulation was pipetted at the same spot as the bacterial suspension (marked in the bottom of the plate) and dried prior to incubation at 37° C. over night. Following incubation, each spot was replated on a LB agar plate and incubated over night. Following incubation, the formed colonies were counted. If the colonies were not countable (>QL) the count was report as estimate (~). If a smear was detected, bacterial load was recorded as +++. Duplicates were performed.

The positive control was the API solved in DMSO, in a concentration equivalent to its MIC for the respective strain.

Coding of Formulations

| Formulation | Code # |
|-------------|--------|
| Formulation C: 1% NEN 15% CD 2% PVP | 1 |
| Formulation D: 1% NEN 50% CD 2% PVP | 2 |
| Formulation E: 2% NEN 50% CD 2% PVP | 3 |
| Formulation G: 1% OXY 50% CD 2% PVP | 4 |
| Control: Vehicle: 15% CD 2% PVP | 5 |
| Control: Vehicle: 50% CD 2% PVP | 6 |
| Control: Inoculum | 7 |
| Positive control: Niclosamide in DMSO (0.25 µg/mL) | 8 |
| Positive control Oxycozanide in DMSO (0.5 µg/mL) | 9 |

Results

1. OD Measurement—Bacterial Load Inoculum

| A | B | C |
|---|---|---|
| 0.1005 | 0.114 | 0.1035 |

2. Average CFU Counts

| 1 | 2 | 3 | 4 | |
|---|---|---|---|---|
| ~131 | 54 | 23 | 0 | A (ATCC 29213) |
| >~180 | ~>54 | 64.5 | 21 | B (MRSA 434844) |
| ~114 | 8 | 73 | 0 | C (Newman) |

All controls (5 to 9) were +++ (i.e. smear detected).

As both positive controls were negative further the experiment was repeated using different concentrations in a spot test using the same methodology described above.

Niclosamide in DMSO was tested at concentrations of 100 µg/mL, 10 µg/mL and 1 µg/mL; Oxyclozanide in DMSO was tested at 40 µg/mL, 4 µg/mL and 0.4 µg/mL with each of the respective strains. In this experiment the negative control was the bacterial suspension only.

Only the highest concentrations of niclosamide and oxyclozanide substantially decreased the bacterial load (200×-400× MIC of Niclo, 180× MIC Oxy).

Conclusion

All formulations tested comprising niclosamide or oxyclozanide and cyclodextrin reduced the bacterial load compared to the vehicle.

Oxyclozanide had the highest efficiency in reducing bacterial load of *S. aureus*.

The antibacterial data in Examples 4 and 5, together with the data showing that niclosamide is active against viruses such as SARS CoV-2 (Wu et al. 2004 and Xu et al. 2020 infra) and the inflammatory biomarker data in WO 2020/039073 demonstrate that niclosamide has anti-bacterial, anti-inflammatory and anti-viral properties. Taken together these data make it plausible that the inhalable formulations described herein may be effective in the treatment or prevention of respiratory viral infections such as SARS CoV-2 and diseases associated with respiratory viral infections such as COVID-19.

Example 6: Batch Manufacturing of Niclosamide Ethanolamine Nebuliser Solution The formulation shown in Table 5 was prepared as described below:

TABLE 5

| Composition Component (trade name) | Formulation F % (w/w) |
|---|---|
| Niclosamide ethanolamine | 1.0 |
| Polyvinylpyrrolidone (PVP K30) | 2.0 |
| Hydroxypropyl Beta-cyclodextrin (Kleptose ® HPB) | 15.00 |
| NaOH | ca. 0.2* |
| 2N HCl | ca. 2.0* |
| Water for injection | q.s. up to |
| Total | 100.00 |

*as required to provide a pH of about 7.8

The nebuliser solution 1% is an isotonic and euhydric aqueous formulation. The solution was filled into 10 mL clear type I moulded glass vials, each vial containing 7 mL of the solution. The nebuliser solution 1% contains 10 mg/mL niclosamide ethanolamine, equivalent to 8.4 mg/mL of niclosamide free base.

The batch formula for 10 kg nebuliser solution 1% is shown in Table 6:

TABLE 6

| Ingredient | Quantity (kg) |
|---|---|
| Niclosamide ethanolamine | 0.10 |
| Polyvinylpyrrolidone (PVP K30) | 0.20 |
| Hydroxypropyl Beta-cyclodextrin (Kleptose ® HPB) | 1.50 |
| NaOH | ca. 0.02* |
| 2N HCl | ca. 0.20* |
| Water for injection | q.s. up to |
| Total | 10.00 |

*as required to provide a final pH of about 7.8

The Bulk Solution was Prepared in a Class C Environment According to the Following Protocol:

1. A tank was charged with hot water (e.g. 65-90° C.) for injection (80% of the total quantity) and stirring was started;
2. The tank was charged with cyclodextrin and NaOH and the mixture stirred until the solid components were completely dissolved to provide a solution of about pH 12;
3. Solid niclosamide ethanolamine was added to the tank and stirring was continued until the niclosamide ethanolamine was completely dissolved to give a solution of approximately pH 8-9;
4. 75% of the total of 2N HCl was added;
5. PVP was added and stirring continued until the PVP was completely dissolved;
6. The solution was cooled to about room temperature;
7. The pH of the solution was adjusted to 7.8 by addition of the remaining 2N HCl, and the pH was recorded;
8. Water for injection was added to the final weight;
9. The solution was discharged into 10 mL glass vials (7 mL solution per vial);
10. The vials were closed with a rubber stopper and sealed with an aluminium cap.

The results of analysis of batches manufactured according to the above protocol are shown below in Table 7:

TABLE 7

| Test | Limit | Batch 1 | Batch 2 |
|---|---|---|---|
| Appearance | Clear red-orange solution essentially free of visible particles | Complies | Complies |
| Identity Niclosamide Ethanolamine | positive (HPLC, conforms with retention time of reference) | positive | positive |
| Assay Niclosamide Ethanolamine | 0.90-1.10 (w/w) | 0.97% | 0.98% |
| Related substances Specified identified: | | | |
| 5-chlorosalicylic acid | <0.3% (w/w) of DS | n.d. | <0.15% |
| 2-chloro-4-nitroaniline | <0.5% (w/w) of DS | n.d. | <0.25% |
| Single unknown impurity | <0.5% (rel. area %) of DS | n.d. | <0.25% |
| Total Impurities | <2.0% (rel. area %) of DS | n.d. | <1.0% |
| Minimum Fill Volume | 7.0 mL | 7.0 mL | 6.7 mL |
| pH | 7.6-8.0 | 7.9 | 8.0 |
| Osmolality | 290-320 mosm | NA | 315 |
| Microbial Quality | TAMC < 102 cfu/g | <100 | <100 |
| | TYMC < 101 cfu/g | <10 | <10 |
| | *S. aureus*: absent | Complies | Complies |
| | *P. aeruginosa*: absent | Complies | Complies |
| | Bile-tolerant gram-negative bacteria: absent | Complies | Complies |

Example 7: Physical Stability of Niclosamide Ethanolamine Aqueous Solution

The stability of different formulations comprising niclosamide ethanolamine, cyclodextrin and polymer was evaluated.

Materials Used

| Trade name | Supplier | Quality |
|---|---|---|
| Niclosamide ethanolamine (NEN) | — | GMP |
| Kollidon 17PF (PVP K17) | BASF | Ph.Eur. |
| Kollidon 30 (PVP K30) | BASF | Ph.Eur. |

-continued

| Trade name | Supplier | Quality |
|---|---|---|
| Kollidon VA64 (PVP/VA 64) | BASF | Ph.Eur. |
| AQOAT AS-MF (HPCMAS) | Shin-Etsu | Ph.Eur. |
| Kleptose HPB (HP-β-CD) | Roquette | GMP |
| Captisol (SBE-β-CD) | Ligand | — |

Methods

Sample Preparation

Table 8 shows the compositions of 18 different formulations which were prepared. The cyclodextrin, polymer and NEN were weighed into a 20 mL glass vial. To this, 100 µL of 5 M NaOH was added along with water for injection (WFI) to yield 10 g of formulation, and the mixture was vortexed for 1 min. The suspension was then ultrasonicated at 70° C. for 5 min and vortexed for 1 min. This procedure was repeated two times or until a clear solution was achieved. The resulting solution was then cooled to room temperature and the pH is adjusted to 7.8-8.0 using 1 M or 5 M HCl. After pH adjustment, the formulation was vortexed for 1 min.

Stability Study

After preparation, the formulations were divided into three 4 mL black capped brown glass vials and stored at 5° C. (dark), 25° C. (light) and 40° C. (dark) at ambient humidity. The samples were evaluated visually for precipitation after 1, 2, 7, 14 and 28 days of storage.

TABLE 8

Composition of the different formulations. The remaining fraction constitutes WFI.

| Formulation | NEN | Kleptose | Captisol | PVP 17 | PVP 30 | PVP/VA | HPMCAS |
|---|---|---|---|---|---|---|---|
| 1 | 2% | 10% | — | 2% | — | — | — |
| 2 | 2% | 10% | — | — | 2% | — | — |
| 3 | 2% | 10% | — | — | — | 2% | — |
| 4 | 2% | 10% | — | — | — | — | 2% |
| 5 | 2% | 15% | — | 2% | — | — | — |
| 6 | 2% | 15% | — | — | 2% | — | — |
| 7 | 2% | 15% | — | — | — | 2% | — |
| 8 | 2% | 15% | — | — | — | — | 2% |
| 9 | 1% | 10% | — | — | 2% | — | — |
| 10 | 1% | 15% | — | — | 2% | — | — |
| 11 | 2% | — | 10% | 2% | — | — | — |
| 12 | 2% | — | 10% | — | 2% | — | — |
| 13 | 2% | — | 10% | — | — | 2% | — |
| 14 | 2% | — | 10% | — | — | — | 2% |
| 15 | 2% | — | 15% | 2% | — | — | — |
| 16 | 2% | — | 15% | — | 2% | — | — |
| 17 | 2% | — | 15% | — | — | 2% | — |
| 18 | 2% | — | 15% | — | — | — | 2% |

Results

Formulations 12, 13, 14, 16, 17 and 18 never formed a clear solution upon preparation. Formulations 4 and 15 precipitated upon the final pH adjustment. The remaining samples were stored at 5° C. (dark), 25° C. (light) and 40° C. (dark).

| Precipitation observed after storage at 5° C. (dark) |
|---|
| Day 1: None |
| Day 2: Formulations 1, 7, 11 |
| Day 7: Formulations 1, 7, 11 |
| Day 14: Formulations 1, 3, 7, 11 |
| Day 28: Formulations 1, 3, 7, 11 |

| Precipitation observed after storage at 25° C. (light) |
|---|
| Day 1: Formulations 1, 7, 11 |
| Day 2: Formulations 1, 3, 7, 11 |
| Day 7: Formulations 1, 3, 7, 11 |
| Day 14: Formulations 1, 2, 3, 6, 7, 11 |
| Day 28: Formulations 1, 2, 3, 6, 7, 11 |

| Precipitation observed after storage at 40° C. (dark) |
|---|
| Day 1: Formulations 1, 3, 7, 11 |
| Day 2: Formulations 1, 2, 3, 6, 7, 11 |
| Day 7: Formulations 1, 2, 3, 5, 6, 7, 11 |
| Day 14: Formulations 1, 2, 3, 5, 6, 7, 8, 11 |
| Day 28: Formulations 1, 2, 3, 5, 6, 7, 8, 9, 11 |

Conclusion

The formulations containing Kleptose were significantly more stable than formulations containing Captisol. Furthermore, the formulations containing 15% Kleptose (Formulations 5-8) were generally more stable than the formulations containing 10% Kleptose (Formulations 1-4) and the formulations containing 1% NEN and PVP K30 (Formulations 9 and 10) were generally more stable than the formulations containing 2% NEN and PVP K30 (Formulations 2 and 6). Storage at lower temperatures increased the physical stability. Formulation 10 (1% NEN, 2% PVP K30 and 15% Kleptose) did not show any sign of precipitation after 12 weeks storage at 5° C. and 25° C. Furthermore, it precipitated later than Formulation 5 after storage at 40° C. and therefore, Formulation 10 displayed the best physical stability of the 18 different formulations tested in this study Example 8: Nebulisation of Aqueous Niclosamide Ethanolamine Formulations The niclosamide ethanolamine (NEN) formulations of Examples 1 and 2 may be nebulised by an electronic nebuliser (for example, an eFlow® electronic nebuliser (ex PARI GmbH)), to provide an aerosol which could be administered to a patient via inhalation. The drug delivery efficiency of the nebulised formulations of Example 1 may be assessed by breath simulation, and the droplet size and distribution pattern may be determined by laser diffraction (as described in US 2009/0304604 A1).

Example 9: Test of Nasal Atomization Device with Niclosamide Solution

Tests were carried out to determine the suitability of a nasal applicator device for the administration of formulation 10 of Example 7. The device tested was the MAD Nasal™ Intranasal Mucosal Atomization Device (catalogue no. MAD130), with a 1.0 mL syringe.

Methods

Differential weighting with a 4 digit balance.

SprayTec from Malvern at 15 L/min (LALLS, Low-Angle Laser Light Scattering).

Test Descriptions and Results

Initial Test: The formulation was taken into the syringe by inserting the blue plastic needle into the vial with active formulation. The blue needle was then removed and the MAD Nasal device was attached. Not much hand force was needed.

Spray with water: About 0.5 mL was sucked up into a fresh syringe. The blue needle was then removed and a MAD Nasal device attached. Two alternative spray direction was then applied, MAD Nasal device down and MAD Nasal device up.

TABLE 9

Remaining amount of formulation in the syringe after use

|  | Remaining amount of water (mL) |
|---|---|
| MAD Nasal device down | 0.08 |
| MAD Nasal device up | 0.19 |

LALLS testing: Droplet size distribution was assessed twice with similar results, as shown in Table 10.

TABLE 10

D10, D50 and D90 for two LALLS tests (in μm).

|  | D10 | D50 | D90 |
|---|---|---|---|
| Test 1 | 33 | 65 | 159 |
| Test 2 | 30 | 62 | 209 |

Dose variability testing: Six new (directly taken from the pouch) MAD Nasal devices were tested with the formulation using the following procedure:

1) The syringe was removed from the plastic pouch and weighed.
2) The syringe was filled with formulation up to 0.35 mL on the syringe and weighed.
3) The needle was exchanged with the MAD Nasal device and weighed.
4) The syringe was emptied with the tip down and weighed.

The Results are shown in Table 11 below.

TABLE 11

Results of differential weighing for six devices.

| | Nr 1 | Nr 2 | Nr 3 | Nr 4 | Nr 5 | Nr 6 | average (g) | sd (g) | RSD (%) |
|---|---|---|---|---|---|---|---|---|---|
| Liquid in syringe (g) | 0.3324 | 0.3197 | 0.3189 | 0.3627 | 0.3475 | 0.3549 | 0.339 | 0.018 | 5.4 |
| Delivered mass (g) | 0.1494 | 0.1643 | 0.2027 | 0.2177 | 0.1794 | 0.2193 | 0.189 | 0.029 | 15.4 |

Conclusions

The MAD Nasal device was found to work well with the formulation of the invention. Filling the device to 0.35 mL resulted in a dose of approximately 0.15 mL with some variability due to manual handling.

Example 10: Non-Clinical Studies

Study A: Dose Range Finding and 2 Week GLP Inhalation Toxicity Study in the Rat

The objectives of this study were to determine the potential toxicity of the formulation shown in Table 5 of Example 6 (1% niclosamide ethanolamine, 2% PVP K30 and 15% Kleptose HPB), when given by inhalation administration to rats at escalating dose level to determine a maximum tolerated dose (MTD Phase) followed by a 2 week repeat dose phase (Fixed Dose Phase) and to evaluate the potential reversibility of any findings. In addition, the toxicokinetic characteristics of Formulation A were determined.

The pivotal 2-week safety study in rats was assessed using daily dose levels of 15 (5-fold higher [systemic mg/kg] and 18-fold higher [local mg/g] compared to a human 30 mg, qd dose) and 50 mg/kg (15-fold higher [systemic mg/kg] and 52-fold higher [local mg/g] compared to a human 30 mg, qd dose) (10 rats/sex/group for main study evaluation); both vehicle and air control groups were also included. This pivotal phase was preceded by a range finding phase which selected a high dose level of 50 mg/kg for use in the pivotal 2-week phase. Microscopic evaluation of the nasal cavity in rats after 2 weeks of daily dosing revealed a non-adverse minimal hypertrophy of goblet (mucin-secreting) cells in the nasal septum/nasopharynx at 15 and 50 mg/kg which was not dose related; these changes were not observed in the vehicle or air control groups and were considered an adaptive change to repeated administration of niclosamide ethanolamine. In the lungs, minimal to mild increase in alveolar macrophages were observed after 2 weeks of dosing in the vehicle and 15 and 50 mg/kg dose groups; these changes were not considered adverse but instead an adaptive to response to clearance of the vehicle. No other noteworthy histopathological findings have been reported to date.

Study B: Dose Range Finding and 2 Week GLP Inhalation Toxicity Study in the Beagle Dog The objectives of this study were to determine the potential toxicity of the formulation shown in Table 5 of Example 6, when given by inhalation administration to dogs at escalating dose level to determine a maximum tolerated dose (MTD Phase) followed by a 2 week repeat dose phase (Fixed Dose Phase) and to evaluate the potential reversibility of any findings. In addition, the toxicokinetic characteristics of the formulation were determined.

The pivotal 2-week safety study in dogs was assessed using daily dose levels of 2.5 (2-fold [systemic mg/kg] and 4-fold higher [local mg/g] to a human 30 mg, qd dose) and 4.37/4.14 mg/kg (3-fold higher [systemic mg/kg] and 6-fold higher [local mg/g] compared to a human 30 mg, qd dose) (3/sex/group for main study evaluation); both vehicle and air control groups were also included. After 2 weeks of daily dosing, microscopic evaluation in male and female dogs administered vehicle or 2.5 mg/kg and in females dosed at 4.14 mg/kg revealed no changes to the nasal cavity and only minimal changes in the lungs including minimal increased alveolar macrophages and mixed/mononuclear cell infiltration, minimal bronchial exudate, and mild neutrophilic infiltration or mild increased cellularity in tracheobronchial lymph node secondary to the minimal lung findings. The histological changes seen after 2 weeks of dosing were minor and not considered adverse.

Study C: Pulmonary Pharmacokinetics of Nebulized Niclosamide in Sheep Following Pulmonary Administration (Non-GLP)

The objectives of this study were to determine the pharmacokinetic profile of the formulation shown in Table 5 of Example 6, when given by pulmonary administration to sheep at escalating dose levels similar to the clinical escalation scheme coupled with a safety assessment using lung function tests.

The PK analysis in the sheep following treatment demonstrated substantial exposure of niclosamide in the epithelial lining fluid (ELF). Peak concentrations exceed 100-fold of the IC90 value of niclosamide against SARS-CoV-2. In spite of substantial clearance from the ELF, niclosamide concentrations above the IC90 are maintained for the 8-hour sampling period following a single administration Formulation A (FIG. 1A). These data support the twice daily administration of the formulation.

Additionally, the ELF concentrations of niclosamide in this study greatly exceed the published plasma pharmacokinetics published from studies using oral niclosamide and provide the pharmacological rationale for using formulations according to the invention for treatment of COVID-19 compared to oral dosage forms of niclosamide. As viral elimination is most likely driven by pulmonary rather than systemic exposure, the efficacy margin achieved with Formulation A following pulmonary administration is much greater (efficacy margin of mean Cmax in ELF to IC90 is >100 fold) in the relevant region of viral replication than the one with the oral route (efficacy margin mean systemic exposure of human oral dose to IC90 exists only for 2 g/day dose, which is 8-fold), although definite lung levels after oral administration of niclosamide remain unknown (FIG. 1B).

Niclosamide systemic exposure after administration was in the range of values reported in humans following oral exposure, with Cmax of 577 ng/mL (mean) [range: 217-803 ng/mL]. Additionally, the treatment was found to be well tolerated in the sheep as determined by lung function analysis pre and post dosing.

Example 11: Clinical Trials

The following clinical trial may be performed using a niclosamide ethanolamine or oxyclozanide formulation described herein, such as Formulation A described in Example 1.

Clinical Trial Protocol—Phase 1
Study Design

An ascending dose scaling study in adult healthy volunteers (HVs) to assess the safety of three increasing doses of a formulation of the invention.

27 healthy volunteers will be enrolled in three sequential cohorts:

Cohort 1: 9 healthy volunteers, 7 to receive a single dose of a 0.75% formulation of the invention (4 mL) and 2 to receive placebo.

Cohort 2: 9 healthy volunteers, 7 to receive a single dose of a 2.0% formulation of the invention (4 mL) and 2 to receive placebo.

Cohort 3: 9 healthy volunteers, 7 to receive a single dose of a 5.0% formulation of the invention (4 mL) and 2 to receive placebo.

Screening and enrolment for the cohorts will be initiated in parallel, while dosing will be done sequentially. Dosing will begin with Cohort 1. Once data from a minimum of 8 subjects (i.e., at least 6 subjects on active treatment) from Cohort 1 is available, the safety parameters will be assessed by a Safety Monitoring Committee (SMC) before initiating dosing of subjects in Cohort 2. Similarly, the SMC will review the data from a minimum of 8 subjects in Cohort 2 before opening for dosing in Cohort 3. Based on the results of this study, the SMC will make a recommendation concerning the dosing in a subsequent Phase 2 study in patients infected by COVID19 and hospitalised to be initiated immediately after this protocol (Phase 1). For all three cohorts, one subject will be dosed with a formulation of the invention (open label) the first day and followed for 24 hours, while admitted at the clinic to confirm the safety of the new dose before dosing the remaining subjects in the cohort. If safety concerns are observed, the SMC will be involved to adjudicate; if no safety concerns are observed or the SMC judges it is safe to continue dosing, the remaining 8 subjects in each cohort will be randomised and dosed (double-blinded) with an interval of at least one hour. Once safety and PK data are available from all cohorts, the SMC will assess the safety parameters and review the PK data to confirm safety of the three doses. Based on this, the SMC will recommend a dose for administration in COVID-19 patients in the next phase of development.

Should subjects experience coughing, discomfort and/or pain associated with inhalation of the nebulized investigational product (IP) (to such an extent that the investigator assesses it will be an issue for administration), the investigator may decide that inhaled lidocaine can be administered prior to inhalation of IP. The first subject in Cohort 1 should be dosed without lidocaine, if issues are observed in Cohort 1 or later cohorts, the investigator can decide to administer lidocaine for certain or all the remaining subjects at his/her discretion.

Screening may be performed up to 21 days before initiation of study treatment (an oropharyngeal swab will be collected between 1 to 3 days before dosing to confirm that HV subjects are not infected with COVID-19).

For subjects to qualify for enrolment in in the study, they cannot be smokers, should be in good general heath and have a normal medical history excluding any chronic disease as per the investigator's judgment, as well as minimum 80% of predicted lung function, including Forced Expiratory Volume in 1 second (FEV1) after beta2-agonist, Total Lung Capacity (TLC), Carbon Monoxide Diffusion capacity (DCO), Fractional Exhaled Nitric Oxide (FeNO), and a 6-Minute Walking Test (6-MWT) with pulse oximetry. Finally, vital signs, ECG and chest X-ray must not be clinically significantly abnormal (see Exclusion criteria for full details).

Investigational Product (IP) will be a single ascending dose or placebo administered by qualified study staff, after which the subject will be followed for 24 hours in the clinic and return for a final check 48 hours after dosing.

A general physical examination, serum chemistry and haematology sampling as well as urinalysis will be performed at screening, 24, and 48 hours after dosing. If the first screening visit is conducted more than 3 days before dosing, the subject must come to the clinic 1 to 3 days before dosing for an oropharyngeal swab (to confirm no infection with SARS-CoV2) and sampling for serum chemistry, haematology, and urinalysis. In terms of respiratory function, safety will be assessed on the basis of spirometry (vital capacity and FEV1) as well as pulse oximetry performed pre-dose as well as 1, 3, 6, 12, and 24 hours after dosing. FEV1 (including reversibility), TLC, DCO, and FeNO will be measured and a 6-MWT with pulse oximetry will be conducted during the screening period (between ICF signing and dosing) and on Day 2 after dosing (the day of dosing is designated as Day 0). ECGs will be captured at screening, pre-dose, 3, 6, and 24 hours after dosing, while vital signs (systemic blood pressure, pulse, respiratory rate (RR), and body temperature) will be measured at screening, pre-dose, 1, 3, 6, 12, 24, and 48 hours post dose. AEs will be collected through-out the study period. Finally, an oropharyngeal swab for detection of viruses and bacteria will be taken pre-dose and 48 hours after dosing for post hoc exploratory analysis of potential changes in the microbiome.

Blood samples for PK analysis will be collected pre-dose, ½, 1, 1%, 2, 3, 6, 12, and 24 hours after dosing.

Inclusion Criteria

Subjects are only eligible if they fulfil all criteria for inclusion:

(1) Signed Informed Consent Form (ICF).
(2) Male or nonpregnant and nonlactating female who is abstinent or agrees to use effective contraceptive methods throughout the course of the study. Females must have a negative urine beta-human chorionic gonadotropin hormone (hCG) pregnancy test prior to dosing (women who are postmenopausal (menopause is defined as the time when there have been no menstrual periods for 12 consecutive months and no other biological or physiological cause can be identified) or who had tubal ligation/hysterectomy do not need to have a pregnancy test done and do not need to agree to use contraception).
Acceptable birth control methods are the following:
Intrauterine device in place for at least 3 months.
Stable hormonal contraceptive for at least 3 months prior to dosing and continuing through study completion.
(3) ECG without clinically significant abnormalities (including QTcF <450 ms).
(4) Age ≥18 and <65 years at the time of signing ICF.
(5) Normally active and in good health by medical history and physical examination.
(6) Minimum 80% of predicted lung function, including FEV1 after beta2-agonist, TLC, DCO, FeNO, and 6-MWT with pulse oximetry.
(7) Chest X-ray without clinically significant abnormalities.

Exclusion Criteria

Subjects who meet any of the following criteria are not eligible to participate in this study:

(1) Enrolment in a niclosamide study in the previous 6 months.
(2) Clinically significant allergy (as judged by the investigator) or history of significant adverse reaction to niclosamide or related compounds, to any of the excipients used, or to lidocaine.
(3) Underlying condition that may interfere with inhalation of the IP.
(4) Current acute or chronic condition (including COPD, asthma, or other severe respiratory disease, CV disease, diabetes mellitus, obesity, malignant and autoimmune diseases) unless considered clinically irrelevant and stable by the investigator.
(5) Renal impairment (eGFR (eGFR estimated by CPK-EPI)<60 ml/min/1.73 m$^2$) or hepatic impairment (as judged by the investigator).
(6) The presence of a condition which renders the subject "vulnerable" as defined by GCP or of a condition the investigator believes would interfere with the ability to provide informed consent, or comply with study procedures/instructions, or that might confound the interpretation of the study results or put the subject at undue risk.
(7) Smoke or regular use of any form of nicotine product including e-cigarette, snuff, chewing tobacco, nicotine gum, etc., for the previous 6 months.
(8) Known difficulty undergoing venipuncture or poor venous access.
(9) Whole blood donation or loss (>400 mL) within 90 days before the dosing of IP.
(10) History of any malignancy except subjects with adequately treated basal cell/squamous carcinomas of the skin.
(11) Consumed alcohol in the 24 hours prior to dosing.

Prior or Concomitant Therapy

(12) Any systemic and inhaled therapies 5 half-lives prior to dosing (hormone replacement therapy for postmenopausal women and hormonal anticonception are allowed).
(13) Participation in any clinical trial 90 days prior to dosing of a formulation of the invention or placebo.

Administration

Qualified staff will administer 4 mL 0.75%, 2.0% or 5.0% of a formulation of the invention, or placebo once daily.

Inhalation is performed by using an EN 13544-1 certified nebulizer.

Duration of Study Subject participation in the study (excluding the screening period) is approximately 3 days, not including potential follow-up of ongoing (S)AEs or pregnancies.

Endpoints and Criteria for Evaluation

Primary Endpoint

Safety assessment of subjects treated with a single dose of a formulation of the invention.

Exploratory End Points (to be Analysed Post Hoc):

Oropharyngeal microbiome changes.

Key PK Parameters:

Maximum quantity of active drug molecules in blood ($C_{max}$).

Time to reach maximum level ($T_{max}$).

Area Under the Curve of drug level in blood versus time (AUC).

Clinical Trial Protocol—Phase 2

Study Design

A clinical study to assess safety and explore efficacy of QID (final dosing frequency can be adjusted by the SMC based on Cohort 1 data) treatment with the selected dose (to be determined in the preceding Phase 1 study in healthy volunteers described above) of a formulation of the invention in adult patients with moderate COVID-19.

44 subjects with COVID-19 will be enrolled in two sequential cohorts:

Cohort 1: 4 COVID-19 patients to be treated with a formulation of the invention in the selected concentration BID (2 subjects) or QID (2 subjects) for 15 days.
Cohort 2: 40 COVID-19 patients, 20 to be treated with a formulation of the invention in the selected concentration, and 20 to receive placebo, QID for 15 days.

This is an adaptive study design with a Safety Monitoring Committee (SMC) responsible for adjudicating safety signals and responsible for assessing safety before opening for enrolment in Cohort 2.

The study will begin with screening and enrolment of patients in Cohort 1. The purpose of Cohort 1 is to confirm safety and tolerability of dosing in patients. For this purpose, all four subjects in this cohort will be treated with a formulation of the invention (open-label, no placebo) and enrolled in one centre to ensure experience is collected within this centre and the responsible investigator together with the SMC can assess safety across the cohort. Treatment will start with two patients treated BID, who shall be followed for 48 hours. In case safety concerns are observed with a possible, probable or definite relationship with Investigational Product (IP), the SMC will be convened to adjudicate. If no safety concerns are observed, or the SMC judges it is safe to continue, the last two subjects in the cohort can be initiated on QID treatment. Once safety data is available for 4 days of treatment for the subjects in Cohort 1, it will be assessed by the SMC to confirm the safety before initiating enrolment of subjects in Cohort 2. Subjects in Cohort 2 will be enrolled in multiple centres in a randomised, double-blind, parallel group cohort to ensure an unbiased assessment of safety and efficacy.

Should subjects in either cohort experience coughing, discomfort and/or pain associated with inhalation of the nebulized IP (to such an extent that the investigator assesses it will be an issue for administration), the investigator may decide that inhaled lidocaine can be administered prior to inhalation of IP. The first subject in Cohort 1 should be dosed without lidocaine (unless the preceding Phase 1 study of a formulation of the invention in healthy volunteers has determined that administering lidocaine before dosing should be adopted for all subjects), if issues are observed in Cohort 1 or later cohorts the investigator can decide to administer lidocaine for the remaining subjects in the cohort currently being dosed and the SMC shall subsequently make a decision on whether to implement this for all remaining IP administrations in the study.

For subjects to be eligible for the study, they must be hospitalised with COVID-19 confirmed by a positive SARS-CoV2 test (can be analysed according to standard at the local laboratory. A back-up sample should be collected for central analysis and semi-quantification of the viral load). Eligible patients will have moderate disease defined as need for hospitalisation but requiring no more than 5 L oxygen ($O_2$)/minute, not requiring ventilation, and not being admitted to an intensive care unit (ICU). Finally, eligible subjects cannot currently be treated with other exploratory anti-viral treatments or other investigational products.

IP or placebo will be administered by qualified staff in the hospital BID or QID for fifteen days.

A general physical examination, serum chemistry and haematology sampling as well as urinalysis will be performed at screening, pre-dose, Day 7 and Day 14 (the day of first dosing is designated Day 0). In addition, safety will be assessed on the basis of daily oximetry measurements and daily assessment of the clinical respiratory status. ECGs will be collected screening, pre-dose, 24, and 48 hours after dosing, and on Days 7, 14, and AEs will be collected through-out the study period. Finally, an oropharyngeal swab for detection of viruses and bacteria will be taken pre-dose and on Day 14 for post hoc exploratory analysis of potential changes in the microbiome.

Blood samples for PK analysis will be collected pre-dose, ½, 1, 1½, 2, 3, 6, 12, 24, and 48 hours after first dosing as well as on Days 7 and 14.

Efficacy will be explored based on daily assessment of clinical respiratory status, pulse oximetry (also collected for safety), and body temperature and other flu symptom descriptors. At pre-dose (if feasible), on Day 7 and Day 14 a 6-Minute Walking Test (6-MWT) with oxygen uptake measurement will be performed. In addition, nasopharyngeal swabs will be collected every other day (and analysed centrally by PT-PCR to achieve a semi-quantitative measure of viral load) and at pre-dose, Day 7 and Day 14 (to be analysed centrally by BioFire® to detect both virus and bacteria). Blood samples will be collected at pre-dose, Day 7, and Day 14 to analyse the time to seroconversion (IgM to IgG), and samples for serum inflammatory biomarker analysis (primary markers: CRP, leukocytes; exploratory markers for post hoc analysis: IL1B, IFNγ, IP10, MCP1, GCSF, MIP1A, TNFα (Huang et al., "Clinical features of patients infected with 2019 novel coronavirus in Wuhan, China", The Lancet, Vol. 395, Issue 102223, p 497-506, 15 Feb. 2020)) will be collected at pre-dose, 48 hours after dosing, and on Days 7 and 14. Finally, if a chest X-ray or CT scan has been collected during hospitalisation, a similar image should be captured on Day 14.

Subjects are considered cured of COVID-19 if the following criteria are met for 72 hours:
  Clinical respiratory status: normal (no symptoms, no need for oxygen therapy).
  No fever.
  Normal oxygen saturation.
  2 successive nasopharyngeal swaps tested negative for SARS-CoV-2.

If a patient is cured, treatment with IP (or placebo) should be stopped (and the subject may be discharged from the hospital if the investigator decides so). The subject should still come to the hospital for the Day 14 tests as outlined in the schedule of events (to avoid spreading the virus in case of a relapse, the subject must come for a nasopharyngeal swap to be tested for SARS-CoV2 on Day 13 and can only come for the Day 14 visit if confirmed negative).

Inclusion Criteria

Subjects are only eligible if they fulfil all criteria for inclusion:
1. Signed Informed Consent Form (ICF).
2. Male or nonpregnant and nonlactating female who is abstinent or agrees to use effective contraceptive methods throughout the course of the study. Females must have a negative urine beta-human chorionic gonadotropin hormone (hCG) pregnancy test prior to (first) dosing (women who are postmenopausal (menopause is defined as the time when there have been no menstrual periods for 12 consecutive months and no other biological or physiological cause can be identified) or who had tubal ligation/hysterectomy do not need to have a pregnancy test done and do not need to agree to use contraception).
    Acceptable birth control methods are the following:
        Intrauterine device in place for at least 3 months.
        Stable hormonal contraceptive for at least 3 months prior to (first) dosing and continuing through study completion.
3. ECG without clinically significant abnormalities (including QTcF <450 ms).
4. Age ≥18 and <80 years at the time of signing ICF.
5. Hospitalised with COVID-19 confirmed by a positive SARS-CoV2 test.
6. Moderate disease defined as requiring no more than 5 L oxygen ($O_2$)/minute, not requiring ventilation, and not being admitted to an intensive care unit (ICU).
7. Prior to infection with SARS-CoV-2, normally active and otherwise in good health by medical history and physical examination as determined by investigator's judgment.

Exclusion Criteria

Subjects who meet any of the following criteria are not eligible to participate in this study:
1. Enrollment in a NEN study in the previous 6 months.
2. Clinically significant allergy (as judged by the investigator) or history of significant adverse reaction to niclosamide or related compounds, to any of the excipients used, or to lidocaine.
3. Underlying condition that may interfere with inhalation of the IP.
4. Current acute or chronic condition (including COPD, asthma, or other severe respiratory disease, CV disease, diabetes mellitus, obesity, malignant and autoimmune diseases) unless considered clinically irrelevant and stable by the investigator.
5. Renal impairment (eGFR <60 mL/min/1.73 m$^2$) or hepatic impairment (as judged by the investigator).
6. The presence of a condition which renders the subject "vulnerable" as defined by GCP or of a condition the investigator believes would interfere with the ability to provide informed consent, or comply with study procedures/instructions, or that might confound the interpretation of the study results or put the subject at undue risk.
7. Active or acute viral infection (other than SARS-CoV-2), and/or bacterial infection in the nasal area.
8. Severe COVID-19, defined as requiring more than 5 L oxygen/minute, ventilation and/or admission in an ICU.

Prior or Concomitant Therapy
9. Current or prior (after COVID-19 diagnosis) exposure to exploratory anti-viral treatments or other IP.

Administration

Qualified staff will administer 4 mL of a formulation of the invention in the selected dose (to be determined in the preceding Phase 1 study in healthy volunteers) or placebo BID or QID (Cohort 1) and QID (Cohort 2) for 15 days.

Maximum dose to potentially be tested is 5% of a formulation of the invention QID.

In case coughing, discomfort or pain is experienced by subjects inhaling the IP, inhaled lidocaine may be administered before dosing the IP.

Inhalation is performed by using an EN 13544-1 certified nebulizer, and sufficient measures will be taken to prevent that dosing infected subjects with a nebulizer results in spread of SARS-CoV2, e.g., by using a nebulizer with spacer or other device to ensure that exhaled air and sputum from the subject cannot be aerosolized or by dosing the inhalation inside an airtight mask.

Duration of Study

Subject participation in the study (excluding the screening period) is up to 15 days (not including potential follow-up of ongoing (S)AEs or pregnancies).

Efficacy Variables

Efficacy will be assessed based on:
Change in clinical respiratory status (including need for oxygen therapy) (daily).
Eradication of SARS-CoV-2 (in the nasopharynx) (every other day).
Change in blood oxygen saturation (daily).
Change in body temperature and other flu symptoms (daily).
Oxygen uptake in 6-MWT (Day 7 and 14).
Chest X-ray or CT scans (optional) (Day 14).
Change in serum inflammatory biomarkers (primary marker: CRP, leukocytes; exploratory markers (for post hoc analysis): IL1B, IFNγ, IP10, MCP1, GCSF, MIP1A, and TNFα (Huang et al.)) (Day 2, 7, and 14).

Endpoints and Criteria for Evaluation

Primary Endpoint—Day 14:
Safety assessment of COVID-19 patients treated QID for 14 days.
Secondary Endpoints:
Safety assessment of COVID-19 patients treated QID based on daily observations and on Day 2, and Day 7.
Safety assessment of COVID-19 patients treated BID based on daily observations and on Day 2, Day 7, and Day 14.
Change in clinical respiratory status (on a scale from 0—no signs/symptoms, to 4—very severe, need for intubation) at end of treatment (daily).
Conversion rates between clinical respiratory statuses (daily).
Time to remission of respiratory symptoms (daily).
Time to independence from oxygen therapy (daily).
Change in resting blood oxygen saturation (daily).
Sequential Organ Failure Assessment (SOFA) score (from 0 to 24) (daily).
Share of subjects admitted to ICU (daily).
Time to reduction in fever or other flu symptoms (daily).
SARS-Cov-2 eradication time (measured in the nasopharynx) (every other day).
Change in SARS-Cov-2 viral load (measured in the nasopharynx) (every other day).
Reduction in pulmonary edema/inflammation as assessed by chest X-ray or CT scan (optional) (Day 15).
Inflammatory serum biomarker (CRP, leukocytes) normalisation (Day 2, 7, and 14).
Change in oxygen uptake in 6-MWT (Day 7 and 14).
Exploratory End Points (to be Analysed Post Hoc):
Oropharyngeal microbiome changes (Day 14).
Exploratory serum biomarkers of COVID-19 associated inflammation (IL1B, IFNγ, IP10, MCP1, GCSF, MIP1A, and TNFα).

PK Parameters:
Maximum quantity of active drug molecules in blood ($C_{max}$).
Time to reach maximum level ($T_{max}$).
Area Under the Curve of drug level in blood versus time (AUC).

Efficacy Analysis

The exploratory efficacy endpoints include change in clinical respiratory status, time to remission of respiratory symptoms, time to independence from oxygen therapy, SOFA score, reduction in fever or other flu symptoms, reduction in pulmonary edema/inflammation, SARS-Cov-2 eradication time, change in primary inflammatory serum biomarkers (CRP, leukocytes), change in blood oxygen saturation will be presented in tables as well as graphically over time from baseline to Day 14 with LOCF. In addition, shift tables will be provided between baseline and each time point for the categorical variables. The cumulative distribution function (CDF) of clinical respiratory status changes from baseline will be plotted to identify where the best separation between treatment and placebo occurs.

The same analyses as above will be repeated in the Per Protocol (PP) analysis set for all above primary and secondary endpoints using observed cases only. The PP Analysis Set will include data from Cohort 2 subjects who were randomised and had no important protocol deviations affecting efficacy assessment throughout the IP administration period (not including healthy volunteers.

Example 12: Phase 2 Clinical Trial

The following clinical trial may be performed using a niclosamide ethanolamine or oxyclozanide formulation described herein, such as Formulation A described in Example 1.

Clinical Trial Protocol

This study is to assess the safety and efficacy of a 1% formulation of the invention in subjects with mild to moderate COVID-19. Its primary endpoint is Time to clinical improvement (defined as at least 2 grades improvement in the modified WHO ordinal scale). This trial has an adaptative design and includes two intermediate analyses: 1. a safety analysis based on the data collected in the first 20 patients enrolled and hospitalized; 2. A proof of mechanism based on the antiviral activity measured by viral load in the first 80 subjects treated. These analyses will be conducted by a SMC which will recommend on two decisions: the authorization to treat patients at home and the decision to complete the study.

The phase II study will focus on the population that is likely to respond to a drug with a primary mode of action being to prevent viral replication: patients hospitalized with moderate COVID-19 and subjects with flu-like signs and symptoms not needing hospitalization (mild COVID-19).

All enrolled subjects will receive a 1% formulation of the invention or a placebo in a twice-daily procedure including a spray of 150 µL of the investigational product in each nostril followed by the nebulization of 6 mL of the investigational product. The treatment duration is 14 days for all subjects, even in case of clinical cure. In patients showing a worsening of the signs and symptoms of COVID-19, treatment should be pursued without change, unless an exclusion criterion would be met, for example need for mechanical ventilation or hospitalization in an intensive care unit.

For confirming the safety of a 1% formulation of the invention, the 20 first subjects included in this study will be hospitalized during the first days of treatment (hospitalization could be prolonged at investigator discretion and depending on the respiratory or medical status). A SMC would analyze all safety data generated in these subjects and recommend on the safety of administering the treatment at home by a nurse in subjects not needing hospitalization.

After 80 subjects will have completed the study (this number is subject to revision following Statistical input), a soft database lock will be performed for these subjects and an analysis will be conducted to provide proof of mechanism by confirming efficacy on the anti-viral end points of the 1% formulation of the invention, based on the time to viral clearance (measured via throat swabs or saliva sampling, the most sensitive and specific test being to be confirmed). The DMC will review the data of this analysis, and should they find no anti-viral effect, the DMC could recommend stopping the study for futility. While the proof of mechanism analysis is ongoing recruitment of the remaining subjects will continue.

Study Population

Eligible subjects for this study must have a positive test confirming infection with SARS-CoV-2 and present signs and symptoms of COVID-19. They cannot currently be treated with other anti-viral treatments or other investigational products. Standard of care treatments are allowed and should be recorded as concomitant treatments. Patients with severe and unstable concomitant pathologies, patients needing invasive mechanical ventilation or extracorporeal membrane oxygenation and patients hospitalized in intensive care units cannot be enrolled.

Product Administration

In this study, the investigational product will be administered by a qualified person at home or in the centre where the subject would have been admitted for isolation or at the hospital. The qualified person is either a physician, a medical student or a nurse specifically trained with the product and its potential risks.

Efficacy Assessments

The anti-viral efficacy will be assessed by the SARS-CoV-2 titers determined by PT-PCR from saliva or nasopharyngeal samples collected at baseline and every day until D14 (most sensitive and specific test still to be confirmed).

The Clinical efficacy in all subjects will be based on the assessment of flu-like symptoms scoring (by investigator and patient), oximetry, NEWS2 score and COVID-19 severity based on an ordinal scale.

The ordinal scale is derived from the scale for clinical improvement defined by the WHO committee and used in the remdesivir studies. This scale had however to be adapted to capture milder severities.

The NEWS2 score is based on a simple aggregate scoring system in which a score is allocated to physiological measurements, already recorded in routine practice, when patients present to, or are being monitored in hospital. Six simple physiological parameters form the basis of the scoring system: respiration rate, oxygen saturation, systolic blood pressure, pulse rate, level of consciousness, temperature (see below).

In addition, metrics defined in the FDA guidance will be used:

All-cause mortality

Respiratory failure (i.e., need for mechanical ventilation, ECMO, noninvasive ventilation, or high-flow nasal cannula oxygen delivery)

Need for intensive care unit (ICU) level care based on clear definitions and specific clinical criteria Need for hospitalization Sustained clinical recovery (e.g., resolution of symptoms)—Chest x-ray (or other imaging, e.g., CT scan) and serum inflammatory biomarkers (primary marker: CRP) will be considered exploratory measures.

Functional respiratory tests cannot be conducted acutely during the active phase of viral infection. These tests will however be conducted after viral clearance in a specialized respiratory unit, two weeks and one months after treatment discontinuation if the patient condition allows it.

Number of Subjects

This study will enroll approximately 350 subjects (the exact number may be determined following statistical input) to ensure a good representation of the different levels of disease severity of mild to moderate COVID-19. The recruitment of a sufficient number of subjects with either mild or moderate COVID-19 will be secured by a careful selection of study centres and involvement of hospital units.

The sample size needed for the interim analysis is based on the assumption that a clinically relevant and medically meaningful benefit is defined by at least 4-day difference in the meantime to viral clearance (defined as first day of 2 consecutive negative tests) when compared to placebo.

Inclusion Criteria Subjects are only eligible if they fulfil all criteria for inclusion:

1. Age ≥18 and <80 years
2. Male or nonpregnant and nonlactating female who is abstinent throughout the course of the study. Females must have a negative urine beta-human chorionic gonadotropin hormone (hCG) pregnancy test at Day 1. (Women who are postmenopausal or who had tubal ligation/hysterectomy do not need to have a urine or serum pregnancy test and do not need to agree to use contraception.)

3. Able to understand and provide signed informed consent.
4. With Nasopharyngeal swab or saliva test confirming infection with SARS-CoV-2 and mild to moderate signs and symptoms of COVID-19.

Exclusion Criteria

Subjects who meet any of the following criteria are not eligible to participate in this study:
1. Enrolment in a niclosamide study in the previous 6 months
2. Allergy to niclosamide or history of significant adverse reaction to niclosamide or related compounds, or to any of the excipients used.
3. Underlying condition that may interfere with inhalation of the IP.
4. Current acute or chronic unstable condition (incl. respiratory disease, CV disease, diabetes mellitus, obesity) unless considered clinically irrelevant by the investigator.
5. The presence of a condition the investigator believes would interfere with the ability to provide consent, or comply with study instructions, or that might confound the interpretation of the study results or put the subject at undue risk.
6. Active or acute infection other than SARS-CoV-2, including bacterial superinfection.
7. Severe COVID-19 requiring mechanical ventilation or admission in an intensive care unit.

Prior or Concomitant Therapy
8. Systemic anti-viral therapies or other investigational products the month prior Day 1.
9. Anti-cancer or immunosuppressive drugs three months prior to Day 1.

Test Product(s), Dose, Mode of Administration, and Duration of Treatment

A nurse, a dedicated medical student, or an investigator will administer 150 µL of a 1% formulation of the invention or placebo in each nostril followed by a nebulization of 6 mL of 1% formulation of the invention or placebo, twice daily for a maximum of 14 days.

Duration of Study

Subject participation in the study (excluding the screening period) is 14 days with an additional 14-day follow-up period to be extended to 28-days if respiratory function is still abnormal.

Efficacy Variables

Anti-viral Efficacy will be assessed based on:
Eradication of SARS-CoV-2 (in the nasopharynx)
Viral load
Clinical Efficacy will be assessed based on:
Changes in the modified WHO ordinal scale
Severity of Flu-like signs and symptoms (including fever)
Changes in Respiratory status assessed by oximetry (blood oxygen saturation)
Changes in NEWS2 score
Chest x-ray (or other imaging, e.g., CT scans) abnormalities
Change in serum inflammatory biomarkers (primary marker: CRP)
Respiratory function status at end of follow-up period
Shortness of breath questionnaire with St George Respiratory Questionnaire
Specific respiratory tests will be conducted to assess of the status pulmonary function.

PK Variables

A blood sample will be collected on Day 7 and at D14 for measure of trough levels before investigational product administration.

Endpoints and Criteria for Evaluation

Primary Endpoint

Time to clinical improvement (at least 2 grades in the modified WHO ordinal scale)

Secondary Endpoints

Based on modified WHO ordinal scale
Percentage of subject cleared (score 0) at D7 and D14
Percentage of live subjects discharged from hospital at D7, D14 and FU visits
Percentage of subjects with score 6 at D7, D14 and FU visits
Distribution within different scores at D7, D14 and FU visits
Percentage of subjects having worsened by 1, 2, 3 or more grades Based on viral sampling
Time to viral clearance defined as the time to the first of two consecutive negative tests for SARS-CoV-2
Percentage of subjects achieving viral clearance at each visit
Mean viral load (AUC of viral particle titers) during the 14-day period
Mean peak viral load during the 14-day period Based on the Flu-like scores
Mean and worst severity score of Flu-like signs and symptoms
Time to disappearance of Flu-like signs and symptoms Based on Oximetry
Percentage of subjects needing oxygen supply at D7 and D14
Mean and worst oximetry measure
Time to independence from oxygen therapy Based on NEWS2 score
Mean and worst NEWS2 score Based on SGRQ
Mean score and worst score Based respiratory tests (VO2max, DCO)
Share of subjects with normal function at FU visits
Mean reduction compared to predicted normal function at FU visits
Percentage of subjects with pulmonary edema/inflammation as assessed by chest x-ray (or other imaging, e.g., CT scan)
Mean change in Inflammatory serum biomarker (CRP, Procalcitonin)

These endpoints will be calculated for the overall population as well as for 2 subpopulations (Mild and Moderate COVID-19 as assessed at baseline).

Scales and Scores

Flu-Like Symptoms Scales

Physician or nurse assessment includes 14 cardinal signs and symptoms to be scored on a 4-point scale from 0 (none) to 3 (Severe) for a total score ranging from 0 to 42:
chills
fever
muscle pain
fatigue
cough
shortness of breath
sneezing
loss of appetite
headache
nasal congestion
ear pain
nausea, vomiting
loss of odor or taste
wheezing.

Patient self-assessment is done using FLU-PRO (Powers et al., *Performance of the inFLUenza Patient-Reported Outcome (FLU-PRO) diary in patients with influenza-like illness (ILI)*. PLoS One. 2018; 13(3):e0194180) or FLUIIQ (Osborne et al., *Development and validation of the Influenza Intensity and Impact Questionnaire (FluiiQ™)*. Value Health. 2011; 14(5):687-699).

| Modified WHO ordinal scale | | |
|---|---|---|
| Severity | Descriptor | Score |
| No disease | Uninfected, no clinical or virological evidence of infection | 0 |
| Healthy carriers | Positive testing by reverse transcription polymerase chain reaction (RT-PCR) assay or equivalent test for SARS-CoV-2, no symptoms | 1 |
| Very mild disease | Ambulatory. Virological evidence of SARS-CoV-2. Symptoms of mild illness with COVID-19 that could include fever, cough, sore throat, malaise, headache, muscle pain, gastrointestinal symptoms. No significant limitation of activities. No signs of viral pneumonia like shortness of breath of dyspnea. | 2 |
| Mild disease - ambulatory | Ambulatory. Virological evidence of SARS-CoV-2. Symptoms of mild illness with COVID-19 that could include fever, cough, sore throat, malaise, headache, muscle pain, gastrointestinal symptoms. Limitation of activities. No or minimal signs of viral pneumonia which do not require special medical care, supplemental oxygen or hospitalization. | 3 |
| Mild disease - hospitalized | Hospitalized. Virological evidence of SARS-CoV-2. Regardless the severity of the Flu-like syndrome, mild signs of pneumonia which require medical attention. No supplemental oxygen needed. | 4 |
| Moderate disease | Hospitalized. Virological evidence of SARS-CoV-2. Regardless the severity of the Flu-like syndrome, moderate viral pneumonia requiring oxygen by mask or nasal prongs. | 5 |
| Severe disease | Hospitalized. Virological evidence of SARS-CoV-2. Severe viral pneumonia requiring high-flow oxygen or non-invasive positive pressure ventilation. | 6 |
| Very severe disease | Hospitalized. Virological evidence of SARS-CoV-2. Very severe viral pneumonia requiring intubation and mechanical ventilation. | 7 |
| Critical disease | Virological evidence of SARS-CoV-2. Hospitalized with critical disease necessitating ventilation + additional organ support – pressors, RRT, ECMO. | 8 |
| Fatal disease | Virological evidence of SARS-CoV-2. Death. | 9 |

| NEWS2 score | | | | | | | |
|---|---|---|---|---|---|---|---|
| Physiological parameter | Score | | | | | | |
| | 3 | 2 | 1 | 0 | 1 | 2 | 3 |
| Respiration rate (per minute) | ≤8 | | 9-11 | 12-20 | | 21-24 | ≥25 |
| SpO$_2$ Scale 1 (%) | ≤91 | 92-93 | 94-95 | ≥96 | | | |
| SpO$_2$ Scale 2 (%) | ≤83 | 84-85 | 86-87 | 88-92 | 93-94 on oxygen | 95-96 on oxygen | 97 on oxygen |
| Air or oxygen | | Oxygen | | Air | | | |
| Systolic blood pressure (mmHg) | ≤90 | 91-100 | 101-110 | 111-219 | | | ≥220 |
| Pulse (per minute) | ≤40 | | 41-50 | 51-90 | 91-110 | 111-130 | ≥131 |
| Consciousness | | | | Alert | | | CVPU |
| Temperature (° C.) | ≤35.0 | | 35.1-36.0 | 36.1-38.0 | 38.1-39.0 | ≥39.1 | |

| NEWS thresholds and triggers | | |
|---|---|---|
| NEW score | Clinical risk | Response |
| Aggregate score 0-4 | Low | Ward-based response |
| Score of 3 in any individual parameter | Low-medium | urgent ward-based response |
| Aggregate score of 5-6 | Medium | Key threshold for urgent response |
| Aggregate score of 7 or more | High | Urgent or emergency response |

Example 13: Phase I Trial of Inhaled Niclosamide

A randomized, placebo-controlled, double-blind, multiple dosing Phase 1 trial was conducted to assess the safety of the formulation shown in Table 5 of Example 6 (or an equivalent formulation comprising 0.1% w/w niclosamide, the balance being water) in healthy volunteers.

Methods

Trial Design and Oversight

This was a single centre, interventional, double-blinded (open label for the first sentinel subject within each cohort), placebo-controlled, Phase 1 study to assess the safety and explore PK parameters of niclosamide ethanolamine in healthy volunteers (HV). The study consisted of five cohorts, which started one after the other, each after consultation of the Safety Monitoring Committee (SMC). Each cohort started only if the previously collected data did not give raise to safety concerns. 44 eligible HVs were enrolled in five sequential cohorts for dose finding, each cohort were screened generally followed by extended respiratory workout one or two days before dosing. If all inclusion and no exclusion criteria were met, dosing was fulfilled followed by 24 hours monitoring. After 48 hours, all participants had the same extensive respiratory work-out as prior to the study inclusion. 34 of these 44 healthy controls receive the investigational product (IP), and 10 the placebo. The study was partly conducted in an open-label design (first subject in cohort 1-4 as sentinel subject), and partly double blinded (subsequent subjects in cohorts 1-4 and all subjects in cohort 5). The doses of the different cohorts are displayed in Table 12.

TABLE 12

Summary of cohorts with its dose and duration of treatment

| Cohort | Dose |
|---|---|
| 1 | 9 healthy volunteers, 7 received a single dose of formulation (4 mL, 0.1%, equalling 3.4 mg niclosamide) and nasal spray (2 × 150 µL, 0.1%, i.e. once per nostril, totalling 0.25 mg niclosamide) and 2 received placebo |
| 2 | 9 healthy volunteers, 7 received a single dose of formulation (1 mL, 1%, equalling 8.4 mg niclosamide) and nasal spray (2 × 150 µL, 1%, totalling 0.25 mg niclosamide) and 2 received placebo. |
| 3 | 9 healthy volunteers, 7 received a single dose of formulation (3 mL, 1%, equalling 25.2 mg niclosamide) and nasal spray (2 × 150 µL, 1%, totalling 0.25 mg niclosamide) and 2 received placebo. |
| 4 | 9 healthy volunteers, 7 received a single dose of formulation (6 mL, 1%, equalling 50.4 mg niclosamide) and nasal spray (2 × 150 µL, 1%, totalling 0.25 mg niclosamide) and 2 received placebo. |
| 5 | 8 healthy volunteers, 6 received five doses of formulation (6 mL, 1%, equalling 50.4 mg niclosamide per dosing and 252 mg in total) and nasal spray (2 × 150 µL, 1%, totalling 2.5 mg niclosamide per dosing and 12.6 mg in total) dosed BID for 2.5 days and 2 received placebo. |

For cohorts 1-4, one subject was dosed with the IP the first day (Monday) and followed for 24 hours while admitted at the clinic to assess safety of the new dose. Safety visit with extended lung function measurements were performed the following Wednesday to Friday at CFAS. For cohort 5, patients received a total of 5 administrations and stayed at the trial site for 3 days (Monday or Tuesday onto Thursday or Friday), including overnight. In cohort 5, as the dose was the same as in cohort 4, all patients were blinded and randomized. Safety visit with extended lung function measurements were performed the following Thursday to Saturday at CFAS.

Throughout the study, both IP were administered by qualified study staff. Each treatment was assigned to a specific subject by randomization number. Screening and enrolment was done sequentially for one cohort after the other. A randomization number was assigned in ascending order to each eligible subject at Day 0 according to the randomization list by cohort. The first number of the cohorts 1, 2, 3 and 4 was always active (open label) and the remaining consisted of 6 active and 2 placebos (n=9). For cohort 5, the numbers consisted of 6 active and 2 placebos (n=8).

Eligibility

Subjects who signed Informed Consent Form (ICF), were male or nonpregnant and nonlactating female who was abstinent or agreed to use effective contraceptive methods throughout the course of the study, females who had a negative urine beta-human chorionic gonadotropin hormone (hCG) pregnancy test prior to and did not need to agree to use contraception, showed an electrocardiogram (ECG) without clinically significant abnormalities (including QTcF <450 ms), were 18 and <65 years at the time of signing ICF, were normally active and in good health by medical history with no current chronic diseases and normal physical examination, had minimum 80% of predicted lung function, including expiratory volume (FEV1) after β2-agonist, static volume (TLC), diffusion capacity (DCO), and normal cardiopulmonary exercise testing (CPET) with pulse oximetry as well as ECG with a fitness score of >20 mLO$_2$/kg*min for females and >25 mLO$_2$/kg*min and no clinical important arrythmia or desaturation during exercise and furthermore, showed a chest X-ray without clinically significant abnormalities were eligible to participate in this study. Subject that had clinically significant allergies, current acute or chronic condition, renal impairment, underlying condition that may interfere with inhalation of IP, and consumed alcohol in the 24 hours prior dosing were excluded.

Safety Assessment and Outcome Measures

Safety was assessed through the following parameters: adverse events (AEs) reporting, general safety assessments, general physical examination, vital signs, clinical laboratory analysis, including urinalysis, haematology, and serum chemistry, ECGs, vital capacity, TLC, DCO, FEV1, reversibility, fraction of expiratory nitric oxide (FeNO) tests, resting pulse oximetry and CPET with ECG and pulse oximetry.

The primary endpoint was defined as the AE frequency in each cohort and treatment group and the change from baseline for all safety variables measured and frequency of out of range values. Furthermore, the pharmacokinetics following administration was evaluated by determining the maximum concentration of active drug molecules in blood (Cmax), time to reach maximum level (Tmax), area under the curve of drug level in blood versus time (AUC) and the half-life (T½).

Primary Endpoints

AE frequency in each cohort and treatment group

Change from baseline for all safety variables measured and frequency of out of range values In addition to AEs/SAEs collection throughout the study duration, general safety will be assessed via clinical examination, vital sign assessments, ECGs, and laboratory analysis (serum chemistry, hematology, and urinalysis).

Pulmonary function monitored by measurement of vital capacity, expiratory volume (Forced Respiratory Volume in one second, FEV1), static volume (Total Lung Capacity, TLC), diffusion capacity (DCO), exhaled nitric oxide (FeNO) and resting pulse oximetry.

Secondary Endpoints—PK

Maximum concentration of active drug molecules in blood ($C_{max}$)

Time to reach maximum level ($T_{max}$)

Area Under the Curve of drug level in blood versus time (AUC)

Half life

Statistical Analysis

The sample size was considered sufficient to meet the study objectives and to assess treatment safety but was not based on statistical power considerations. Two sets of populations for analysis were distinguished, the Safety Set and the PK Set. The Safety Analysis Set includes data from all enrolled subjects receiving any amount of IP. Descriptive statistics are reported for continuous variables and metric values, including the number of subjects, mean (p), standard deviation (SD), median, minimum (Min), and maximum (Max). Categorical variables are reported as frequencies and percentages. For metric values, absolute change of since baseline are reported, except for FEV1 percentage change is shown. Significance of differences was tested in an exploratory fashion. No imputation for missing data was made. Data from patients receiving placebo were combined across cohorts. For all analyses, the statistical software Stata® (version 16) was used in the most recent sub-version available at data base lock.

The PK Analysis Set included data from subjects who were treated and have no missing data affecting the PK assessment. Subjects with at least one quantifiable drug concentration were included in the PK analysis. No imputation for missing data was made. All pharmacokinetic parameters were calculated using non-compartmental analysis (NCA) with a validated installation of the software Phoenix® WinNonlin® version 8.1.

Results

Trial Population

Forty-four subjects were randomized of which 34 were assigned to treatment and 10 to placebo.

Safety Outcomes

No serious AE nor early discontinuation was reported in this study. In total, 32 subjects experienced one or more AEs during the study. The majority of the AEs belonged to the "Respiratory, thoracic, and mediastinal disorders" category with "Upper respiratory tract irritation" being the most frequent AE descriptor (45 events in 26 subjects, 59%) and corresponding to throat irritation during and after nebulization. Furthermore, the nasal applications did not result in any finding with regards to local tolerability. For the nebulization procedure, there was a dose-dependent difference in terms of tolerability.

However, all AEs reported were mild and disappeared spontaneously and completely without treatment in one to two hours. For most subjects, symptoms were more pronounced during the first 5-10 minutes of the inhalation procedure. Of note, in the multiple administration group, most subjects reported that symptoms decreased over time with repeated dosing. During administration of the drug, some subjects showed an asymptomatic, but significant decrease in FEV1 (>200 mL and >12%), which was reversible with a beta2 agonist, whereas none of the subjects experienced decrease in FVC, nor in DCO.

Asymptomatic airway obstruction (decline in FEV1) was shown in 4 subjects, 3 out of 4 occurring in the highest dose (6 mL) group. These events were all responsive to inhaled β2-mimetic treatment.

In cohort 5, the mean (SD) oxygen uptake was unchanged 3401 (551) prior to drug administration and 3359 (516) (NS), and the mean workload was similar at the two measurements 309 (56) versus 300 (54), NS). Likewise, the FEV1 post beta2-agonist was 116 (16) pre-drug values, and post drug administration 111 (17) (NS), and FVC 117 (14) and 114 (13), respectively (NS) and TLC 104 (11) and 104 (10), respectively (NS). DCO was found to have a significant decrease 102 (10) versus 90 (6), p=0.01, however none showed a clinically significant change of more than 20%. Post drug safety lung function measurements showed asymptomatic decrease in post beta2-agonist FEV1 measurement 1 participants (from 124% pred to 108% pred), two developed significant reversibility (18% and 12%), and 4 had signs of increased airway inflammation (identified as a change in fractional nitric oxide concentration in exhaled breath [FENO]) (Change of 11 ppb, 37 ppb, 37 ppb, 28 ppb) of whom one had elevated FeNO prior to drug administration, all in Cohort 5. None showed clinically significant change in TLC, or VO$_2$max in cohort 1 to 5. One showed a decrease in DCO in cohort 3 (15%) and 3 in cohort 5 (19%, 18%, 16%), however KCO was in all cases unchanged within the clinical acceptable limit.

All but one of the AEs related to abnormal test values were reported with the highest dose in either cohort 4 or cohort 5 and all these events were reported in the active groups and considered by the investigator as being possibly, probably or definitely related to the test product or procedure.

Pharmacokinetics

Pharmacokinetic analyses demonstrated dose-proportional characteristics for niclosamide ethanolamine (FIG. 2). The maximum plasma concentration ($C_{max}$) and Area under the curve ($AUC_{0-8}$) levels following a single dose application were 238.9 ng/mL (mean) and 509.0 hr*ng/mL (mean). Following repeated dosing in Cohort 5, $C_{max}$ and $AUC_{0-8}$ levels of 337.3 ng/mL and 401.2 hr*ng/mL were reported, indicating no accumulation of niclosamide ethanolamine after repeated dosing.

Raw data indicated peak concentrations in blood of 337 ng/mL (mean) [range: 29-506 ng/mL] after repeated inhalation doses. The half-life was shown to be 2 hours (mean) in cohort 4 and 2.7 hours (mean) in cohort 5. This is in the range of systemic exposure reported after oral dosing of niclosamide (see FIG. 3). The systemic PK data from humans (including dose response) is in close agreement with the data from the sheep PK study (see FIG. 4).

As a preliminary conclusion, the formulation of the invention appears to provide systemic exposure within the range observed with the approved 2 g oral dosage form of niclosamide (Yomessan). Additionally, given the route of administration and the sheep ELF PK data, the concentration in the lungs is substantially higher than oral niclosamide and accordingly the formulation would represent a preferred treatment of COVID19 compared to oral dosage forms of niclosamide.

Example 14: Phase 3 Clinical Trial

This is a randomized, parallel-group, placebo-controlled, blinded, multi-center, phase 3 treatment study to assess the safety and efficacy of a 1% niclosamide ethanolamine solution (administered via a nebulizer and as a nasal spray) in hospitalized participants with mild and moderate COVID-19. The dose chosen for this study is twice daily inhalation of 3 mL, 1% niclosamide ethanolamine (equaling 27.4 mg niclosamide) and 150 µL nasal spray, 1%, once per nostril (totaling 2.6 mg niclosamide).

Study Population

In the context of this study, mild and moderate COVID-19 infection is defined by the FDA guidance as follows:

Mild:
Positive testing by standard RT-PCR assay or equivalent testing
Symptoms of mild illness could include fever, cough, sore throat, malaise, headache, muscle pain, GI symptoms, without shortness of breath or dyspnea
No clinical signs indicative of Moderate, Severe, or Critical severity Moderate:
Positive testing by standard RT-PCR assay or equivalent testing
Symptoms of moderate illness could include any symptom of mild illness or shortness of breath with exertion
Clinical signs suggestive of moderate illness with COVID-19, such as respiratory rate 20 breaths/minute, SpO$_2$ >93% on room air at sea level, heart rate 90 beats/minute
No clinical signs indicative of Severe or Critical severity Inclusion Criteria Participants are eligible to be included in the study only if all of the following criteria apply:

1. Participant must be years of age at the time of signing the informed consent form (ICF)

2. Fulfill the criteria for mild to moderate signs and symptoms of COVID-19 as defined by FDA guidance 3. Symptoms or signs of COVID-19 for no more than 4 days prior to enrolment 4. Have test confirming infection with SARS-CoV-2

5. Currently hospitalized

6. Male or nonpregnant and nonlactating female who is abstinent or using contraception throughout the study. Females must have a negative urine beta-human chorionic gonadotropin hormone pregnancy test at Day 1. (Women who are postmenopausal or who had tubal ligation/hysterectomy do not need to have a pregnancy test and do not need to agree to use contraception.)

7. Capable of giving signed informed consent and willing to comply with the requirements and restrictions listed in the informed consent form and in this protocol Exclusion Criteria Participants are excluded from the study if any of the following criteria apply:

1. Active or acute infection other than SARS-CoV-2, including secondary bacterial pneumonia 2. Presence of an acute or chronic condition that, as judged by the investigator, would jeopardize the safety of the participant 3. ALT or AST levels >5 times the upper level of normal 4. Severe or critical COVID-19 disease, i.e. requiring non-invasive or invasive mechanical ventilation, use of high-flow oxygen devices or ECMO 5. Underlying condition that may interfere with inhalation of the IMP 6. Allergy to niclosamide or history of significant adverse reaction to niclosamide or related compounds, or to any of the excipients used 7. Other investigational products within one month prior Day 1 and throughout the study 8. Enrolment in another study for the formulation in the previous 6 months 9. The presence of a condition the investigator believes would interfere with the ability to provide consent, or comply with study instructions, or that might confound the interpretation of the study results.

Administration

All enrolled participants will receive niclosamide ethanolamine Nebulizer Solution 1% or placebo and niclosamide ethanolamine Nasal Spray Solution 1% or placebo in a twice-daily procedure for up to 10 days, while hospitalized. This treatment includes administration of the Nasal Spray Solution 1% or placebo as one spray shot of 130 µL of the solution in each nostril followed by the nebulization of 3 mL of the solution 1% or placebo. Treatment is to discontinue at hospital discharge.

Efficacy Assessments

The modified ordinal scale for clinical improvement will be completed by the investigator. The scale is provided below. The $SpO_2$ value will be determined daily while hospitalized and by clinic staff on Day 28. Participants with an abnormal (<95%) $SpO_2$ on the day of discharge will be provided with a pulse oximeter with instructions. The participant will measure $SpO_2$ at home and report the value at the daily post-treatment visit. Sputum or nasopharyngeal swans for titer of SARS-CoV-2 will be collected daily while hospitalised and by clinic staff on Day 28. Samples will be collected for laboratory analysis of inflammatory biomarkers at the Screening, Day 10 (or day of discharge), and Day 28 visits.

| Participant status | COVID-19 severity | Descriptors integrating FDA guidance | Score |
|---|---|---|---|
| Asymptomatic | Clear | No symptoms | 0 |
| Ambulatory | Almost clear | Very mild symptoms of COVID-19 without limitations in daily activities [a]. Oxygen saturation is normal (≥95% on room air) or equivalent to pre-COVID-19 oxygen requirement | 1 |
| Ambulatory | Mild | Mild residual symptoms of COVID-19 with limitations in daily activities and no need for specific medical oversight [b]. Oxygen saturation is normal at rest (≥95% on room air) or equivalent to pre-COVID-19 oxygen requirement | 2 |
| Hospitalized | Mild | Mild active illness with COVID-19 without evidence of active viral pneumonia or hypoxia but where hospitalization and/or close medical monitoring is needed [c]. Oxygen saturation is normal (≥95% on room air) or equivalent to pre-COVID-19 oxygen requirement | 3 |
| Hospitalized | Moderate | Moderate illness with COVID-19 with clinical signs of pneumonia but no signs of severe pneumonia. Oxygen saturation is >93% on room air at sea level | 4 |
| Hospitalized | Severe | Severe illness with COVID-19 with clinical signs of respiratory distress such as respiratory rate ≥30/minute, heart rate ≥125/minute, $SpO_2$ ≤93% 6on room air at sea level or $PaO_2/FiO_2$ | 5 |
| Hospitalized | Critical | Critical illness, defined by at least one of the following: Respiratory failure [d]; Shock [e]; Multiorgan dysfunction/failure. | 6 |
| Dead | Fatal | Death | 7 |

[a] Persistent fatigue, dyspnea at effort, joint or chest pain, cough or persistent smell or taste dysfunction might be present.
[b] Fatigue or dyspnea at rest preventing some daily activities are present. If participant is discharged from the hospital, but still needs close medical monitoring or oxygen therapy at home, they should be categorized in score 3.
[c] Hospitalization required for medical supervision; can include participants at high risk of complication (eg, due to comorbidities) or those recovering from the disease but needing medical oversight before hospital discharge.
[d] Requiring at least one of the following: endotracheal intubation and mechanical ventilation, oxygen delivered by high-flow nasal cannula (heated, humidified, oxygen delivered via reinforced nasal cannula at flow rates >20 L/min with fraction of delivered oxygen ≥0.5), non-invasive positive pressure ventilation, ECMO, or clinical diagnosis of respiratory failure (i.e., clinical need for one of the preceding therapies, but preceding therapies not able to be administered in setting of resource limitation).
[e] Systolic blood pressure <90 mmHg or diastolic blood pressure <60 mmHg or requiring vasopressors.

Pharmacokinetics & Biomarkers

Plasma, serum or whole blood samples will be collected for measurement of niclosamide concentrations.

Samples will be tested for C-reactive protein and procalcitonin to evaluate their association with observed clinical responses.

Statistical Considerations

The null and alternative hypotheses for the primary efficacy outcome, time to clinical improvement, are the following:

$$H0: h1(t)=h2(t)$$

$$H1: h1(t) \neq h2(t)$$

Where:

h1(t) is the hazard function in the inhalation group h2(t) is the hazard function in the placebo group The remdesivir study of moderate and severe COVID-19 subjects found that the median time to recovery, defined as being a 1 (not hospitalized, no limitations of activity), 2 (not hospitalized, limitation of activities, home oxygen requirement or both) or 3 (hospitalized, not requiring supplemental oxygen and no longer requiring ongoing medical care) on the ordinal scale was 11 days versus 15 days for subjects receiving remdesivir and placebo, respectively, with a hazard ratio of 1.32. Since this study will enroll participants with mild and moderate COVID-19, the outcome is improvement rather than recovery, and some participants may be receiving concomitant remdesivir, it is expected that the time to clinical improvement will be shorter than in the remdesivir study. Assuming the median time to clinical improvement is 9.7 days in the inhalation 1% group and 13.55 days in the placebo group (hazard ratio of 1.40), 80% power, 2-sided alpha=0.05, and a 2:1 randomization ratio, a total of 328 events are required. Assuming an event rate of 90% and a 5% lost to follow-up rate, approximately 387 subjects need to be enrolled.

Primary Endpoints

The primary efficacy outcome is time to clinical improvement (at least 2 grades in the modified ordinal scale) in the ITT analysis set. The description of the estimand includes four attributes: the population, the variable (or endpoint) to be obtained for each participant, the specification of how to account for intercurrent events (ICE), and the population-level summary for the variable. The estimand attributes for time to clinical improvement will be provided in detail in the SAP.

Kaplan-Meier (KM) analysis will be used to assess time to clinical improvement in the inhalation and placebo groups. Participants who do not improve (including death) or are lost to follow-up will be censored at the date of last assessment or date of death. Participants who receive rescue therapy with remdesivir will be censored at the start date of remdesivir treatment. The 25th percentile, median and 75th percentile for time to clinical improvement and 95% confidence intervals (CIs) will be determined in each treatment group. The hazard ratio for clinical improvement and 95% CI will also be determined using a Cox regression model with covariates for treatment, COVID-19 severity (mild and moderate), country/geographic region, and age (<75 and ≥75 years). KM survival curves will be provided.

A log-rank test, stratified for the randomization factors of COVID-19 severity (mild and moderate), country/geographic region, and age (<75 and ≥75 years), will be performed to test for differences in survival curves between the two treatment groups. If the p-value is <0.05 (i.e., a 2-sided alpha level of 0.05), the null hypothesis will be rejected.

Analyses of the primary efficacy outcome, time to clinical improvement, will also be conducted in the subgroups defined by COVID-19 severity (mild and moderate), country/geographic region, age (<75 and ≥75 years), and receipt of concomitant remdesivir (yes and no), as well as in the m-ITT and PP analyses sets. Other subgroup analyses will be defined in the SAP.

Secondary Endpoint(s)

The following key secondary analyses will be completed in the ITT analysis set. To control for the inflation of the overall type I error rate, a hierarchical testing procedure will be used. If statistical significance is declared for the primary efficacy outcome, testing will be done for the key secondary efficacy outcomes in the order listed below. Testing will proceed to the next secondary outcome only if statistical significance (2-sided alpha=0.05) is declared for the preceding secondary outcome being tested.

A frequency distribution of the scores from the modified ordinal scale will be presented by treatment group at Day 14. Differences between treatment groups will be tested for statistical significance using a proportional-odds logistic regression with covariates for treatment and each of the randomization stratification factors. The odds ratio and 95% CI for treatment will be presented.

The number and percentage of participants with respiratory failure defined as the need for high-flow oxygen, mechanical ventilation, ECMO or non-invasive ventilation will be presented by treatment group. The Cochran-Mantel-Haenzsel test, stratified for the randomization stratification factors, will be used to determine statistical significance between the treatment groups.

KM methods will be utilized to analyze time to no need for oxygen therapy or return to the oxygen level needed before COVID-19 disease with participants who do not return to pre-COVID-19 oxygen level, deaths or who are lost to follow-up censored at the date last assessed or last date known to be alive. Participants who receive rescue therapy with remdesivir will be censored at the start date of remdesivir treatment. Kaplan-Meier curves will be provided. The 25th, 75th percentiles and the median time to no need for oxygen therapy or return to oxygen level needed before COVID-19 as well as 95% CIs will be determined. The hazard ratio and 95% CI will also be determined using a Cox regression model with covariates for treatment, COVID-19 severity (mild and moderate), country/geographic region, and age (<75 and ≥75 years). KM survival curves will be provided. Differences between survival curves will be tested for statistical significance using the log-rank test stratified by the randomization stratification factors.

Kaplan-Meier methods will be utilized to analyze survival time with participants who remain alive or are lost to follow-up censored at the last date known to be alive. Kaplan-Meier survival curves will be provided. The 25th, 75th percentiles and the median survival time as well as the probability of being alive at Day 28 will be determined by treatment group. Statistically significant differences between treatment groups in the probability of being alive at Day 28 will be determined using a Z-statistic and Greenwoods formula for the standard deviation.

Additional analyses of the key secondary endpoints will be conducted. These include analyses in the subpopulations defined by the randomization stratification factors and in the m-ITT and PP analysis sets. Summaries of additional secondary endpoints will also be conducted including:

Time to viral clearance defined as the time to the first of 2 consecutive negative tests for SARS-CoV-2 will be summarized using KM methods. Participants who do not have viral clearance (including deaths) or are lost to follow-up will be censored at the date of last viral test or date of death. Participants who receive rescue therapy with remdesivir will be censored at the start date of remdesivir treatment. The 25th percentile, median and 75th percentile for time to viral clearance and 95% CIs will be determined in each treatment group. The hazard ratio for viral clearance and 95% CI will also be determined using a Cox regression model with covariates for treatment, COVID-19 severity (mild and moderate), country/geographic region, and age (<75 and ≥75 years). KM survival curves will be provided.

The probability of having viral clearance at each time point it is measured will be determined from the KM analysis.

Descriptive statistics of the mean viral burden (AUC of viral particle titers) during the 10-day treatment period will be provided.

Descriptive statistics of the peak viral load during the 10-day treatment period will be provided.

Tertiary/Exploratory Endpoint(s)

Summaries of the additional efficacy outcomes by treatment group will be conducted in the ITT analysis set to support the findings of the primary and secondary efficacy outcomes as follows:

A frequency distribution of the scores from the modified ordinal scale at end of treatment/discharge and Day 28.

Number and percentage of participants cleared (modified ordinal scale=0) or almost cleared (modified ordinal scale=1) at Day 14, end of treatment/discharge and Day 28.

Time to clearance/almost clearance will be summarized using KM methods. Participants who do not have clearance/almost clearance (including death) or are lost to follow-up will be censored at the date of last assessment or date of death. Participants who receive rescue therapy with remdesivir will be censored at the start date of remdesivir treatment. The 25th percentile, median and 75th percentile for time to clearance/almost clearance and 95% CIs will be determined in each treatment group. The hazard ratio for clearance/almost clearance and 95% CI will also be determined using a Cox regression model with covariates for treatment, COVID-19 severity (mild and moderate), geographic region (US and non-US), and age (<75 and ≥75 years). KM survival curves will be provided.

Number and percentage of participants with an improvement in the modified ordinal scale of at least 1 grade lower than baseline=0) at Day 14 and Day 28.

Number and percentage of participants worsened (defined as a modified ordinal scale score higher than baseline) at Day 14 and Day 28.

Number and percentage of participants hospitalized in an ICU at any time during the hospitalization.

Number and percentage of participants needing oxygen therapy at any time during the hospitalization.

Number and percentage of participants receiving mechanical ventilation at any time during the hospitalization.

Number and percentage of participants discharged from the hospital with at least a 2-grade improvement in the modified ordinal scale.

Time to hospital discharge with at least a 2-grade improvement in the modified ordinal scale. Participants who are not discharged (including death) or are lost to follow-up will be censored at the date of last assessment or date of death. Participants who receive rescue therapy with remdesivir will be censored at the start date of remdesivir treatment. The 25th percentile, median and 75th percentile for time to hospital discharge and 95% CIs will be determined in each treatment group. The hazard ratio for hospital discharge and 95% CI will also be determined using a Cox regression model with covariates for treatment, COVID-19 severity (mild and moderate), geographic region (US and non-US), and age (<75 and ≥75 years). KM survival curves will be provided.

For participants who require oxygen therapy, descriptive statistics of the time to sustained return to basal oxygen requirement.

For participants who show a clinical improvement, the number and percentage with a relapse defined as rehospitalization for COVID-19 through Day 28.

Number and percentage of participants with a 402 value of ≤91%, 92-93%, 94-95%, and ≥95% at Day 14, end of treatment/discharge and Day 28.

Number and percentage of participants with a respiration rate (bpm) of ≤9-11, 12-20, 21-24, and ≥25 at Day 14, end of treatment/discharge and Day 28.

Mean change from baseline to each time point measured in C-reactive protein and procalcitonin.

The number and percentage of participants with viral clearance at each time point measured using the subgenomic RNA assay.

Clauses

Further embodiments are set out in the numbered clauses below:

1. A formulation comprising a halogenated salicylanilide, or a pharmaceutically acceptable salt thereof, and a cyclodextrin.

2. The formulation according to clause 1, wherein the halogenated salicylanilide is selected from the group consisting of niclosamide, closantel, oxyclozanide and rafoxanide, or a pharmaceutically acceptable salt thereof.

3. The formulation according to clause 1 or clause 2, wherein the halogenated salicylanilide is niclosamide, or a pharmaceutically acceptable salt thereof.

4. The formulation according to clause 3, wherein the formulation comprises niclosamide in the free-acid form.

5. The formulation according to clause 3, wherein the formulation comprises a pharmaceutically acceptable salt of niclosamide.

6. The formulation according to clause 5, wherein the pharmaceutically acceptable salt is niclosamide ethanolamine.

7. The formulation according to any one of clauses 1 to 6, wherein the formulation is in the form of a solid, optionally in the form of a powder.

8. The formulation according to any one of clauses 1 to 6, wherein the formulation is in the form of a solution, suspension (including a nanosuspension) or dispersion of the halogenated salicylanilide, or a pharmaceutically acceptable salt thereof, and the cyclodextrin in a pharmaceutically acceptable solvent.

9. The formulation according to clause 8, wherein the solvent comprises water.

10. The formulation according to clause 8 or clause 9, wherein the solvent further comprises a co-solvent, optionally wherein the co-solvent comprises DMSO, ethanol, propylene glycol, glycerol, a polyethylene glycol with an average molecular weight of 600 or less, or any combination thereof.

11. The formulation according to clause 10, wherein the co-solvent is present in an amount of from 0 to 20% by weight, for example from 0 to 10% by weight (e.g. 1 wt. %), based on the weight of the formulation.

12. The formulation according to any preceding clause, wherein the formulation is suitable for aerosol administration.

13. The formulation according to any preceding clause, wherein the cyclodextrin comprises β-cyclodextrin or a derivative thereof, optionally wherein the cyclodextrin is hydroxypropyl-β-cyclodextrin (HP-β-CD).

14. The formulation according to any preceding clause, wherein the halogenated salicylanilide, or the pharmaceutically acceptable salt thereof, is present in the formulation in an amount of from 0.05 to 10% by weight, based on the weight of the formulation.

15. The formulation according to clause 14, wherein the formulation is a liquid formulation and the halogenated salicylanilide, or the pharmaceutically acceptable salt thereof, is present in the formulation in an amount of from 0.1 to 5% by weight, e.g. from 0.5 to 2%, based on the weight of the liquid formulation, optionally wherein the halogenated salicylanilide, or the pharmaceutically acceptable salt thereof, is present in the formulation in an amount of about 1% by weight.

16. The formulation according to any preceding clause, wherein the halogenated salicylanilide, or the pharmaceutically acceptable salt thereof, is present in the formulation at a concentration of from 1 to 50 mg/ml.

17. The formulation according to any preceding clause, wherein the cyclodextrin is present in the formulation in an amount of from 1 to 90% by weight, based on the weight of the formulation.

18. The formulation according to clause 17, wherein the formulation is a liquid formulation and the cyclodextrin is present in the formulation in an amount of from 1 to 25% by weight, e.g. from 10 to 20% by weight, preferably 10 to 15% by weight, more preferably about 15% by weight, based on the weight of the formulation.

19. The formulation according to any preceding clause, wherein at least a portion of the halogenated salicylanilide, or the pharmaceutically acceptable salt thereof, forms a complex with the cyclodextrin, optionally wherein from about 20% to about 100% of the halogenated salicylanilide, or the pharmaceutically acceptable salt thereof, forms a complex with the cyclodextrin.

20. The formulation according to any preceding clause, wherein the ratio of the halogenated salicylanilide, or the pharmaceutically acceptable salt thereof, to cyclodextrin is from 1:250 to 5:1, such as from 1:50 to 1:5, preferably 1:20 to 1:10 e.g. about 1:10, or e.g. about 1:15.

21. The formulation according to any preceding clause, further comprising at least one polymer, optionally wherein the polymer is selected from the group consisting of polyvinylpyrrolidone (PVP), polyvinylalcohol (PVA), polyvinylpyrrolidone/vinyl acetate copolymer (PVP/VA), hydroxypropylcellulose (HPC), poloxamers, hydroxypropylmethylcellulose (HPMC), hydroxypropylmethylcellulose acetate succinate (HPMC-AS), and any combination thereof, optionally wherein the polymer comprises PVP.

22. The formulation according to clause 21, wherein the polymer is present in the formulation in an amount of from 0.05 to 20% by weight, for example from 0.1 to 15% by weight (e.g. about 2 wt. %), based on the weight of the formulation.

23. The formulation according to any preceding clause, further comprising a preservative, optionally wherein the preservative comprises benzalkonium chloride.

24. The formulation according to clause 23, wherein the preservative is present in an amount of from 0 to 0.2% by weight, for example from 0 to 0.1% by weight (e.g. 0.01 wt. %), based on the weight of the formulation.

25. The formulation according to any preceding clause, further comprising a stabilising agent, optionally wherein the stabilising agent comprises disodium edetate, disodium phosphate, polysorbate 80, sodium dihydrogen phosphate, sodium citrate, sodium phosphate, sodium acetate, acetic acid, histidine lactic acid, aspartic acid, tartaric acid, glutamic acid, succinic acid, malic acid, tromethamine, lactic acid, histidine, fumaric acid, citric acid, or any combination thereof.

26. The formulation according to clause 25, wherein the stabilising agent is present in an amount of from 0 to 2% by weight, for example from 0.05 to 1% by weight (e.g. 0.1 wt. %), based on the weight of the formulation.

27. The formulation according to any preceding clause, further comprising an electrolyte, optionally wherein the electrolyte comprises sodium chloride, potassium chloride, sodium dihydrogen phosphate, potassium dihydrogen phosphate, or any combination thereof.

28. The formulation according to clause 27, wherein the electrolyte is present in an amount of from 0 to 10% by weight, for example from 0.1 to 0.9% by weight (e.g. 0.5 wt. %), based on the weight of the formulation.

29. The formulation according to any preceding clause, wherein the formulation has a viscosity of from 1 to 150 cP, optionally from 1.5 to 100, from 2 to 50 or from 5 to 25 cP.

30. The formulation according to any preceding clause, wherein the formulation has a pH of from 4 to 9, from 6 to 8, or from 7.6-8.0 (e.g. about 7.8).

31. A liquid formulation according to clause 1 comprising:
  0.5-1.5% niclosamide ethanolamine;
  5-20% cyclodextrin, preferably a β-cyclodextrin, more preferably HP-β-CD;
  0.5-5% PVP (e.g. PVP 30);
  the balance being water,
  wherein the percentages are by weight based on the weight of the liquid formulation; and
  wherein the formulation has a pH of from 7.0 to 8.5, for example from 7.5 to 7.8, or from 7.6 to 8.0, preferably about 7.8.

32. A liquid formulation according to clause 1 comprising:
  about 1% niclosamide ethanolamine;
  about 15% cyclodextrin, preferably a β-cyclodextrin, more preferably HP-β-CD;
  about 2% PVP (e.g. PVP 30);
  the balance being water,
  wherein the percentages are by weight based on the weight of the liquid formulation; and wherein the formulation has a pH of from 7.0 to 8.5, for example from 7.5 to 7.8, or from 7.6 to 8.0, preferably about 7.8.

33. The formulation according to any preceding clause, wherein the formulation has an osmolarity of from 100 to 500 mOsmol/L, for example from 150 to 350 mOsmol/L, preferably from 290 to 320 mOsmol/L.

34. A formulation comprising a halogenated salicylanilide, or a pharmaceutically acceptable salt thereof, and a cyclodextrin, for use as a medicament.

35. A formulation comprising a halogenated salicylanilide, or a pharmaceutically acceptable salt thereof, and a cyclodextrin, for use in the treatment or prevention of an infectious disease or an inflammatory disease in a subject in need thereof.

36. A method of treating or preventing an infectious disease or an inflammatory disease in a subject, the method comprising administering to the subject a therapeutically effective amount of a formulation comprising a halogenated salicylanilide, or a pharmaceutically acceptable salt thereof, and a cyclodextrin.

37. The formulation for use or method according to clause 35 or clause 36, wherein the formulation is as defined by any one of clauses 1 to 33.

38. The formulation for use or method according to any one of clauses 35 to 37, wherein the infectious disease is a pulmonary infection.

39. The formulation for use or method according to any one of clauses 35 to 38, wherein the infectious disease is a viral, bacterial, or fungal infection.

40. The formulation for use or method according to any one of clauses 35 to 39, wherein the infectious disease is a viral infection.

41. The formulation for use or method according to any one of clauses 35 to 40, wherein the viral infection is caused by or associated with a virus selected from respiratory syncytial virus, influenza virus, parainfluenza virus, human metapneumovirus, severe acute respiratory syndrome coronavirus (SARS-CoV), severe acute respiratory syndrome coronavirus (SARS-CoV-2), Middle East respiratory syndrome coronavirus (MERS-CoV), a human rhinovirus (HRVs) and human adenovirus (HAdV).

42. The formulation for use or method according to any one of clauses 35 to 41, wherein the viral infection is caused by or is associated with a Pneumoviridae virus, for example a Human respiratory syncytial virus (HRSV) (e.g. HRSV-A2, HRSV-B1 or HRSV-S2).

43. The formulation for use or method according to clause 41, wherein the viral infection is caused by or associated with a Coronaviridae virus.

44. The formulation for use or method according to clause 43, wherein the virus is selected from Alphacoronavirus, Betacoronavirus, Gammacoronavirus and Deltacoronavirus.

45. The formulation for use according to clause 44, wherein the virus is a Betacoronavirus.

46. The formulation for use or method according to clause 45, wherein the virus is selected from severe acute respiratory syndrome coronavirus (SARS-CoV), severe acute respiratory syndrome coronavirus 2 (SARS-CoV-2), Middle East respiratory syndrome coronavirus (MERS-CoV), HCoV-229E, HCoV-NL63, HCoV-0C43 and HKU1.

47. The formulation for use or method according to clause 45, wherein the viral infection is caused by or associated with SARS-CoV-2.

48. The formulation for use or method according to any one of clauses 41-46, wherein the viral infection is COVID-19; optionally wherein the viral infection is moderate or mild COVID-19.

49. The formulation for use or method according to clause 41, wherein the viral infection is caused by or associated with influenza virus.

50. The formulation for use or method according to clause 35 or 36, wherein the inflammatory disease is a pulmonary inflammatory disease, optionally wherein the pulmonary inflammatory disease is selected from the group consisting of: asthma, chronic obstructive pulmonary disease (COPD), pulmonary fibrosis, pneumonia, interstitial lung disease, sarcoidosis, bronchiolitis obliterans, pneumonitis, acute respiratory distress syndrome (ARDS), bronchiectasis, cystic fibrosis, idiopathic pulmonary fibrosis, radiation induced fibrosis, silicosis, asbestos induced pulmonary or pleural fibrosis, acute lung injury, usual interstitial pneumonia (UIP), Chronic lymphocytic leukemia (CLL)-associated fibrosis, Hamman-Rich syndrome, Caplan syndrome, coal worker's pneumoconiosis, cryptogenic fibrosing alveolitis, obliterative bronchiolitis, chronic bronchitis, emphysema, Wegner's granulamatosis, lung scleroderma, silicosis, asbestos induced pulmonary and/or pleural fibrosis.

51. The formulation for use or method according to any one of clauses 35 to 50, wherein said use comprises administering the formulation by inhalation intraorally and/or intranasally, optionally wherein the formulation is administered by inhalation intraorally; optionally wherein optionally wherein the formulation is administered by intranasally and by inhalation intraorally.

52. The formulation for use or method according to any one of clauses 35 to 50, wherein said use comprises administering the formulation intranasally.

53. The formulation for use or method according to clause 51 or 52, wherein said use comprises administering from 50 to 500 µl, from 100 to 200 µl or from 130 to 150 µl of a liquid formulation per nostril.

54. The formulation for use or method according to any one of clauses 51 to 53, wherein said use comprises administering from 1 to 10 ml, from 2 to 8 ml or from 3 to 6 ml of a liquid formulation intraorally (e.g. via a nebuliser).

55. The formulation for use or method according to any one of clauses 35 to 54, wherein said use comprises administering the formulation in the form of an aerosol.

56. The formulation for use or method according to any one clauses 35 to 55, wherein the a halogenated salicylanilide, or a pharmaceutically acceptable salt thereof, is administered to the subject in a unit dosage of from about 10 mg to about 1000 mg based on the weight of niclosamide (for example from about 100 mg to about 600 mg, preferably about 150 mg to about 500 mg, based on the weight of niclosamide).

57. The formulation for use or method according to any one clauses 35 to 56, wherein the liquid formulation is administered to the subject one to five times per day, for example from 1 to 4 times per day, e.g. 2 or 3 times per day.

58. The formulation for use or method according to any one of clauses 35 to 57, wherein said use further comprises administering an antitussive agent prior to or concurrently with the formulation.

59. The formulation for use or method according to clause 58, wherein the antitussive agent is selected from codeine, dextromethorphan, hydrocodone, methadone, butorphanol, benzonatate, ethylmorphine, oxeladin, pipazethate, pholcodine, noscapine, butamirate and a local anaesthetic.

60. The formulation for use or method according to clause 58, wherein the antitussive agent is a local anaesthetic, optionally lidocaine.

61. The formulation for use or method according to any one of clauses 39 to 49 or 51 to 60, wherein the viral infection is associated with inflammation.

62. The formulation for use or method according to any one of clauses 35 to 61, wherein the treatment results in a decrease in mucus production and/or secretion, a decrease in bronchoconstriction, repression of pro-inflammatory cytokines, modulation of the activity of dendritic cells, and/or inhibition of STAT3.

63. The formulation for use or method according to any one of clauses 39 to 49 or 51 to 62, wherein the viral infection is associated with a secondary bacterial infection.

64. The formulation for use or method according to clause 63, wherein the secondary bacterial infection is caused by a bacterium selected from the group consisting of S. aureus, S. pneumoniae, H. influenzae, M. catarrhalis and S. pyogenes.

65. A formulation comprising a halogenated salicylanilide, or a pharmaceutically acceptable salt thereof, and a cyclodextrin, for use in the treatment or prevention of an ocular condition or disease in a subject.

66. A method of treating or preventing an ocular condition or disease in a subject, the method comprising administering to the subject a therapeutically effective amount of a formulation comprising a halogenated salicylanilide, or a pharmaceutically acceptable salt thereof, and a cyclodextrin.

67. The formulation for use or method according to clause 65 or clause 66, wherein the ocular condition or disease is an infectious ocular disease or an inflammatory eye disease.

68. The formulation for use or method according to clause 67, wherein the infectious ocular disease is selected from the group consisting of conjunctivitis (including bacterial, fungal and viral conjunctivitis), keratitis (including viral, bacterial, fungal and amoebic keratitis), endophthalmitis, blepharitis, sty, uveitis, cellulitis (e.g. bacterial cellulitis), ocular gonorrhoea and ocular herpes.

69. The formulation for use of method according to clause 68, wherein the inflammatory eye disease is elected from dry eye disorder (DED), ocular rosacea, uveitis (e.g. Birdshot retinochoroidopathy), severe conjunctivitis, diabetic retinopathy, multifocal choroiditis with panuveitis, serpiginous choroidopathy, scleritis, an eye inflammation associated with allergy (such as allergic conjunctivitis), and an eye inflammation associated with an autoimmune disorder (e.g. mucous membrane pempigold, eye inflammation associated with infection, retinitis pigmentosa, ankylosing spondylitis, Behcet's syndrome, dermatomyositis, Graves' disease, juvenile rheumatoid arthritis, multiple sclerosis, psoriatic arthritis, blepharitis, Reiter's syndrome, rheumatoid arthritis, Sjogren's syndrome, systemic lupus erythematosus, and Wegener's granulatomatosis).

70. The formulation for use or method according to clause 67, wherein the ocular condition or disease is bacterial conjunctivitis, optionally wherein the bacterial conjunctivitis is caused by a bacteria selected from the group consisting of S. aureus (including MRSA), S. pneumoniae, H. influenzae, P. aeruginosa, M. catarrhalis and N. gonorrhoeae.

71. The formulation for use or method according to clause 67, wherein the ocular condition or disease is viral conjunctivitis, optionally wherein the viral conjunctivitis is caused by herpes simplex virus (HSV), especially type 1 or type 2 HSV; human herpesvirus 6; adenovirus; molluscum contagiosum virus; varicella-zoster virus; Epstein-Barr virus; cytomegalovirus; picornavirus; hepatitis B virus; mumps virus; measles virus; and influenza virus; for example type 1 or type 2 HSV.

72. The formulation for use or method according to any one of clauses 65 to 71, wherein the formulation is a liquid formulation and is administered topically to one or both eyes.

73. The formulation for use or method according to any one of clauses 65 to 72, wherein the formulation is a liquid formulation and comprises an ophthamically acceptable carrier.

74. The formulation for use or method according to any one of clauses 65 to 73, wherein the formulation is as defined by any one of clauses 1 to 33.

75. The formulation for use or method according to any one of clauses 65 to 74, wherein liquid formulation is administered to one or both eyes of the subject one to five times per day, for example from 1 to 4 times per day, e.g. 2 times per day.

75. An aerosol of a solution comprising a halogenated salicylanilide, or a pharmaceutically acceptable salt thereof, and cyclodextrin.

77. An aerosol according to clause 76, wherein the solution comprises niclosamide ethanolamine.

78. The aerosol according to clause 76 or clause 77, wherein solution comprises a solvent, optionally wherein the solvent comprises water.

79. The aerosol according to clause 78, wherein the solvent further comprises a co-solvent, optionally wherein the co-solvent comprises DMSO.

80. The aerosol according to any one of clauses 76 to 79, wherein the cyclodextrin is β-cyclodextrin or a derivative thereof, optionally wherein the cyclodextrin comprises hydroxypropyl-β-cyclodextrin (HP-β-CD).

81. The aerosol according to any one of clauses 76 to 80, wherein the halogenated salicylanilide, or the pharmaceutically acceptable salt thereof, is present in an amount of from 0.1 to 5.0% by weight, based on the weight of the solution.

82. The aerosol according to any one of clauses 76 to 81, wherein the cyclodextrin is present in an amount of from 1 to 25% by weight, based on the weight of the solution.

83. The aerosol according to any one of clauses 76 to 82, wherein at least a portion of the halogenated salicylanilide, or the pharmaceutically acceptable salt thereof, forms a complex with the cyclodextrin, optionally wherein from 20 to 100 wt. % of the halogenated salicylanilide, or the pharmaceutically acceptable salt thereof, is complexed with the cyclodextrin.

84. The aerosol according to any one of clauses 76 to 83, wherein the solution further comprises at least one polymer, optionally wherein the polymer is selected from the group consisting of polyvinylpyrrolidone (PVP), polyvinylalcohol (PVA), polyvinylpyrrolidone/vinyl acetate copolymer (PVP/VA), hydroxypropylcellulose (HPC), poloxamers, hydroxypropylmethylcellulose (HPMC), hydroxypropylmethylcellulose acetate succinate (HPMC-AS), and any combination thereof, optionally wherein the polymer comprises PVP.

85. The aerosol according to clause 81, wherein the at least one polymer is present in the solution in an amount of from 0.05 to 50% by weight of the solution, for example from 0.01 to 10% by weight of the solution (e.g. 2 wt. %).

86. The aerosol according to any one of clauses 76 to 85, wherein the solution further comprises a preservative, optionally wherein the preservative comprises benzalkonium chloride, optionally wherein the preservative is present in an amount of from 0 to 0.05% by weight of the solution, for example from 0 to 0.02% by weight (e.g. 0.01 wt. %).

87. The aerosol according to any one of clauses 76 to 86, wherein the solution further comprises a stabilising agent, optionally wherein the stabilising agent comprises disodium edetate, optionally wherein the stabilising agent is present in an amount of from 0 to 0.5% by weight of the solution, for example from 0 to 0.2% by weight (e.g. 0.1 wt. %).

88. The aerosol according to any one of clauses 76 to 87, wherein the solution further comprises an electrolyte, optionally wherein the electrolyte comprises sodium chloride, optionally wherein the electrolyte is present in an amount of from 0 to 1.5% by weight of the solution, for example from 0 to 0.9% by weight (e.g. 0.5 wt. %).

89. The aerosol according to any one of clauses 76 to 88, wherein the mass median diameter (MMD) of the aerosol is less than about 5 μm.

90. The aerosol according to any one of clauses 76 to 88, wherein the mass median diameter (MMD) of the aerosol is from about 10 to about 150 μm, from about 20 to about 100 μm, from about 40 μm to about 80 μm, or from about 50 μm to about 70 μm.

91. The aerosol according to any one of clauses 76 to 90, for use in the treatment or prevention of an infectious disease or an inflammatory disease in a subject, optionally a pulmonary infectious or inflammatory disease, wherein said use comprises administration of the aerosol to the subject by inhalation.

92. The aerosol for use according to clause 91, wherein the infectious disease is a viral infection.

93. A unit dosage comprising a solution of a halogenated salicylanilide, or a pharmaceutically acceptable salt thereof, and cyclodextrin, wherein the a halogenated salicylanilide is present in an amount of from 0.1 to 200 mg, for example from 0.5 to 100 mg/ml or from 1 to 50 mg/ml.

94. The unit dosage according to clause 93, wherein the unit dosage is present in a container, for example a vial, blister pack, bottle, syringe or drug reservoir within an inhaler device (e.g. a nebulizer).

95. A system comprising:
a formulation comprising a halogenated salicylanilide, or a pharmaceutically acceptable salt thereof, and a cyclodextrin; and
an inhaler device and/or an intranasal delivery device.

96. The system according to clause 95, wherein the formulation is as defined by any one of clauses 1 to 33.

97. A system according to clause 95 or clause 96, wherein the inhaler device is adapted to aerosolize the formulation.

98. A container containing a formulation comprising a halogenated salicylanilide, or a pharmaceutically acceptable salt thereof, and a cyclodextrin.

99. A system or a container according to any one of clauses 95 to 98, wherein the formulation is as defined by any one of clauses 1 to 33.

100. A container according to clause 98 or clause 99, wherein the formulation is in the form of a liquid and the container is configured to dispense droplets of the formulation to the eye.

101. A container according to any one of clauses 98 to 100, wherein the formulation comprises an ophthamically acceptable carrier.

102. A method of preparing a formulation, the method comprising:
adding cyclodextrin and/or a halogenated salicylanilide, or a pharmaceutically acceptable salt thereof, to a solvent to form a suspension;
heating the suspension for a period of time sufficient for the cyclodextrin and/or a halogenated salicylanilide, or a pharmaceutically acceptable salt thereof, to dissolve in the solvent, thereby forming a solution;
cooling the solution.

103. The method of clause 102, wherein the method comprises adding both the cyclodextrin and the halogenated salicylanilide, or a pharmaceutically acceptable salt thereof, to the solvent prior to heating.

104. The method of clause 102, wherein the method comprises pre-heating the solvent prior to the addition of the cyclodextrin and the halogenated salicylanilide, or a pharmaceutically acceptable salt thereof.

105. The method of clause 102, wherein the method comprises:
adding one of a cyclodextrin and a halogenated salicylanilide, or a pharmaceutically acceptable salt thereof, to the solvent to form a suspension;
heating the suspension for a period of time sufficient for the cyclodextrin or the halogenated salicylanilide, or a pharmaceutically acceptable salt thereof, to dissolve in the solvent, thereby forming a first solution;
adding the other of the cyclodextrin and the halogenated salicylanilide, or a pharmaceutically acceptable salt thereof, to the first solution in the form of a solid;
heating the first solution for a period of time sufficient for the solid to dissolve, thereby forming a second solution; and
cooling the solution.

106. The method of clause 102, wherein the method comprises:
adding a cyclodextrin to a solvent to form a first suspension, and heating the first suspension for a period of time sufficient for the cyclodextrin to dissolve in the solvent, thereby forming a first solution;
adding a halogenated salicylanilide, or a pharmaceutically acceptable salt thereof, to a solvent to form a second suspension, and heating the second suspension for a period of time sufficient for the halogenated salicylanilide, or a pharmaceutically acceptable salt thereof, to dissolve in the solvent, thereby forming a second solution;
adding the first solution to the second solution to form a mixture; and
cooling the mixture.

107. The method according to clause 106, wherein the method comprises heating (or continuing to heat) the solution to a temperature of less than 120° C., after adding the first solution to the second solution, prior to cooling.

108. The method according to any one of clauses 102 to 107, wherein heating is carried out to a temperature of less than 120° C., optionally to a temperature of from 50 to 120° C.

109. The method according to any one of clauses 102 to 108, wherein cooling is carried out to a temperature of from 10 to 40° C.

110. The method according to any one of clauses 102 to 109, wherein the cyclodextrin and/or the halogenated salicylanilide is mixed with the solvent prior to and/or during the heating step.

111. The method according to any one of clauses 102 to 110, further comprising raising the pH of the solvent, suspension or solution to a pH of at least 8, optionally wherein the pH is raised to a pH of 8-9.5.

112. The method according to clause 111, wherein the pH is raised prior to the addition of the halogenated salicylanilide, or a pharmaceutically acceptable salt thereof.

113. The method according to any one of clauses 102 to 112, further comprising lowering the pH of the solution, optionally wherein the pH is lowered to a pH of 4-8.

114. The method according to clause 113, wherein the pH of the solution is lowered after the halogenated salicylanilide, or a pharmaceutically acceptable salt thereof, has dissolved in the solvent.

115. The method according to any one of clauses 102 to 114, further comprising adjusting the pH of the solution, for example after cooling the solution, optionally wherein the pH is adjusted to a pH of 7-8.

116. The method according to any one of clauses 102 to 115, wherein the solvent comprises water, optionally wherein the solvent comprises a co-solvent (e.g. DMSO), preferably wherein the solvent is water.

117. The method according to any one of clauses 102 to 116, further comprising adding one or more polymers, optionally wherein the polymer comprises or is PVP.

118. The method according to clause 117, wherein the polymer is added after the cyclodextrin and the halogenated salicylanilide have been dissolved in the solvent.

119. The method according to clause 117 or clause 118, wherein the polymer is added after the pH of the solution has been lowered to a pH of 4-8.

120. The method according to clause 105, or any one of clauses 108-119 when dependent on clause 105, wherein the method comprises:
  optionally, pre-heating a solvent (e.g. water) to a desired temperature, such as 65-70° C.;
  adding cyclodextrin and a base to the solvent to form a first suspension;
  heating the first suspension, or maintaining the temperature of the first suspension at the desired temperature, while mixing for a period of time sufficient for the cyclodextrin to dissolve in the solvent, thereby forming a first solution having a pH of at least 8;
  adding a halogenated salicylanilide (e.g. niclosamide), or a pharmaceutically acceptable salt thereof, to the first solution, to form a second suspension, optionally wherein the halogenated salicylanilide (e.g. niclosamide), or a pharmaceutically acceptable salt thereof, is added in the form of a slurry;
  maintaining the temperature of the second suspension at the desired temperature, while mixing for a period of time sufficient for the halogenated salicylanilide (e.g. niclosamide), or a pharmaceutically acceptable salt thereof, to dissolve, thereby forming a second solution;
  lowering the pH of the second solution to a pH of from 4 to 8 (e.g. by addition of an acid);
  adding a polymer (e.g. PVP) to the second solution, and mixing for a period of time sufficient for the polymer to dissolve in the second solution;
  cooling the second solution (e.g. to a temperature of about 20 to about 30° C.);
  adjusting the pH of the second solution, e.g. to a pH of about 7.5 to about 8.5.

121. The method according to any one of clauses 102 to 120, further comprising adding one or more components to the solvent selected from: one or more electrolytes; one or more stabilisers; one or more preservatives; one or more buffers; or any combination thereof.

122. The method according to any one of clauses 112 to 121, further comprising forming a solid from the solution, optionally wherein the solid is formed by micro-precipitation, lyophilisation, spray drying or spray-freeze drying the solution.

123. The method according to any one of clauses 102 to 122, further comprising diluting the solution to achieve a desired concentration of the halogenated salicylanilide.

What is claimed is:

1. A liquid formulation comprising:
   about 1% niclosamide ethanolamine;
   about 15% hydroxypropyl β-cyclodextrin;
   about 2% polyvinylpyrrolidone;
   the balance being water,
   wherein the percentages are by weight based on the weight of the liquid formulation and wherein the formulation has a pH from 7.0 to 8.5.

2. The liquid formulation of claim 1, wherein the formulation is in the form of a solution, suspension or dispersion of the niclosamide ethanolamine.

3. The liquid formulation of claim 1, wherein the polyvinylpyrrolidone is PVP K30.

4. The liquid formulation of claim 1, wherein the formulation is a liquid formulation comprising:
   1% niclosamide ethanolamine;
   15% hydroxypropyl β-cyclodextrin;
   2% polyvinylpyrrolidone;
   the balance being water,
   wherein the percentages are by weight based on the weight of the liquid formulation; and
   wherein the formulation has a pH of from 7.0 to 8.5.

5. The liquid formulation of claim 4, wherein the polyvinylpyrrolidone is PVP K30.

6. The liquid formulation of claim 4, wherein the formulation has a pH of 7.8.

* * * * *